US010906964B2

(12) United States Patent
Barbour et al.

(10) Patent No.: US 10,906,964 B2
(45) Date of Patent: Feb. 2, 2021

(54) ANTIBODIES RECOGNIZING TAU

(71) Applicant: PROTHENA BIOSCIENCES LIMITED, Dublin (IE)

(72) Inventors: Robin Barbour, Walnut Creek, CA (US); Philip James Dolan, III, Foster City, CA (US); Yue Liu, Foster City, CA (US)

(73) Assignee: PROTHENA BIOSCIENCES LIMITED, Dublin (IE)

(*) Notice: Subject to any disclaimer, the term of this patent is extended or adjusted under 35 U.S.C. 154(b) by 5 days.

(21) Appl. No.: 16/097,445

(22) PCT Filed: May 2, 2017

(86) PCT No.: PCT/IB2017/052545
§ 371 (c)(1),
(2) Date: Oct. 29, 2018

(87) PCT Pub. No.: WO2017/191561
PCT Pub. Date: Nov. 9, 2017

(65) Prior Publication Data
US 2019/0330316 A1    Oct. 31, 2019

Related U.S. Application Data

(60) Provisional application No. 62/330,800, filed on May 2, 2016.

(51) Int. Cl.
*C07K 16/18* (2006.01)
*A61K 47/68* (2017.01)
(Continued)

(52) U.S. Cl.
CPC .......... *C07K 16/18* (2013.01); *A61K 47/6843* (2017.08); *A61P 25/28* (2018.01); *G01N 33/6896* (2013.01); *C07K 2317/14* (2013.01); *C07K 2317/24* (2013.01); *C07K 2317/33* (2013.01); *C07K 2317/34* (2013.01); *C07K 2317/52* (2013.01); *C07K 2317/55* (2013.01); *C07K 2317/565* (2013.01); *C07K 2317/567* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 8,012,936 B2 | 9/2011 | Sigurdsson et al. |
| 8,987,419 B2 | 3/2015 | Barghorn et al. |

(Continued)

FOREIGN PATENT DOCUMENTS

| JP | 2009-056790 A | 2/2009 |
| JP | 2010-511388 A | 4/2010 |

(Continued)

OTHER PUBLICATIONS

U.S. Appl. No. 14/776,724 Advisory Action dated Mar. 12, 2019.
(Continued)

*Primary Examiner* — Adam Weidner
(74) *Attorney, Agent, or Firm* — Alston & Bird LLP

(57) ABSTRACT

The invention provides antibodies that specifically bind tau. The antibodies inhibit or delay tau-associated pathologies and associated symptomatic deterioration.

65 Claims, 15 Drawing Sheets

Specification includes a Sequence Listing.

(51) Int. Cl.
*A61P 25/28* (2006.01)
*G01N 33/68* (2006.01)

(56) References Cited

U.S. PATENT DOCUMENTS

| | | | |
|---|---|---|---|
| 9,321,841 | B2 | 4/2016 | Jones et al. |
| 10,501,531 | B2 | 12/2019 | Seubert et al. |
| 10,752,679 | B2 | 8/2020 | Seubert et al. |
| 2007/0042359 | A1 | 2/2007 | Throsby et al. |
| 2008/0050383 | A1 | 2/2008 | Sigurdsson et al. |
| 2009/0028851 | A1 | 1/2009 | Stuhmer et al. |
| 2010/0022026 | A1 | 1/2010 | Rump et al. |
| 2010/0267927 | A1 | 10/2010 | Garrett et al. |
| 2010/0316564 | A1 | 12/2010 | Sigurdsson |
| 2011/0053264 | A1 | 3/2011 | Kashmiri et al. |
| 2011/0206702 | A1 | 5/2011 | Polakis et al. |
| 2012/0023911 | A1 | 2/2012 | Liu et al. |
| 2012/0100152 | A1 | 4/2012 | Roberts et al. |
| 2012/0142602 | A1 | 6/2012 | Brady et al. |
| 2012/0149880 | A1 | 6/2012 | Cheung et al. |
| 2012/0204275 | A1 | 8/2012 | Schenk et al. |
| 2012/0288507 | A1 | 11/2012 | Qian et al. |
| 2012/0301473 | A1 | 11/2012 | Binder et al. |
| 2012/0308480 | A1 | 12/2012 | Smith et al. |
| 2013/0189289 | A1 | 7/2013 | Inoue et al. |
| 2013/0295021 | A1 | 11/2013 | Chen et al. |
| 2014/0056901 | A1 | 2/2014 | Agadjanyan et al. |
| 2014/0086921 | A1 | 3/2014 | Griswold-Prenner et al. |
| 2014/0171373 | A1 | 6/2014 | Ashe et al. |
| 2014/0294731 | A1 | 10/2014 | Pfeifer et al. |
| 2015/0050215 | A1 | 2/2015 | Novak et al. |
| 2015/0050270 | A1 | 2/2015 | Sanofi |
| 2015/0056721 | A1 | 2/2015 | Siman |
| 2015/0166661 | A1 | 6/2015 | Chen et al. |
| 2015/0175682 | A1 | 6/2015 | Pfeifer et al. |
| 2015/0196663 | A1 | 7/2015 | Shusta et al. |
| 2015/0253341 | A1 | 9/2015 | McAvoy et al. |
| 2015/0266947 | A1 | 9/2015 | Sierks et al. |
| 2016/0031976 | A1 | 2/2016 | Seubert et al. |
| 2016/0376341 | A1 | 12/2016 | Adolfsson et al. |
| 2017/0355756 | A1 | 12/2017 | Julien et al. |
| 2019/0322728 | A1 | 10/2019 | Seubert et al. |
| 2019/0330314 | A1 | 10/2019 | Barbour et al. |
| 2020/0123239 | A1 | 4/2020 | Seubert et al. |

FOREIGN PATENT DOCUMENTS

| | | |
|---|---|---|
| JP | 2011-501655 A | 1/2011 |
| JP | 2012-500020 A | 1/2012 |
| JP | 2015520685 A | 7/2015 |
| JP | 2015-530971 | 10/2015 |
| WO | WO 1996/15452 A1 | 5/1996 |
| WO | WO 2011/154321 A1 | 12/2011 |
| WO | WO 2012/049570 A1 | 4/2012 |
| WO | WO 2013/004717 A1 | 1/2013 |
| WO | WO 2013/007839 A1 | 1/2013 |
| WO | WO 2013/028810 A1 | 2/2013 |
| WO | WO 2013/041962 A1 | 3/2013 |
| WO | WO 2014/008404 A1 | 1/2014 |
| WO | WO 2014/1006000 A2 | 6/2014 |
| WO | WO 2014/152157 A2 | 9/2014 |
| WO | WO 2014/165271 A2 | 10/2014 |
| WO | WO 2014/165271 A3 | 10/2014 |
| WO | WO 2016/079597 A1 | 5/2016 |
| WO | WO 2015/200806 A1 | 12/2016 |
| WO | WO 2017/062672 A2 | 4/2017 |
| WO | WO 2017/191559 A1 | 11/2017 |
| WO | WO 2017/191560 A1 | 11/2017 |
| WO | WO 2017/191561 A1 | 11/2017 |
| WO | WO 2018/156250 A1 | 8/2018 |
| WO | WO 2018/204546 A2 | 11/2018 |
| WO | WO 2020/096608 A1 | 5/2020 |
| WO | WO 2020/097561 A1 | 5/2020 |
| WO | WO 2020/163817 A1 | 8/2020 |
| WO | WO 2020/180819 A1 | 9/2020 |

OTHER PUBLICATIONS

U.S. Appl. No. 14/776,724 Notice of Allowance dated Apr. 10, 2019.
PCT/US2018/030739 International Search Report and Written Opinion dated Nov. 5, 2018.
PCT/US2018/059895 International Search Report and Written Opinion dated Apr. 12, 2019.
PCT/US2018/030739 International Search Report and Written Opinion dated Sep. 18, 2018.
Goedert, et al., "Cloning and sequencing of the cDNA encoding a core protein of the paired helical filament of Alzheimer disease: Identification as the microtubule-associated protein tau" *Proc. Natl. Acad. Sci. USA*, vol. 85, pp. 4051-4055, (Jun. 1998).
PCT/US2014/025044 International Search Report and Written Opinion dated Nov. 3, 2014.
Vigo-Pelfrey, et al., "Elevation of microtubule-associated protein tau in the cerebrospinal fluid of patients with Alzheimer's disease", *Neurology*, 45:788-793 (1995).
PCT/US2014/025044 Invitation to Pay Additional Fees and, Where Applicable, Protest Fee dated Aug. 15, 2014.
EP 14778358.2 European Supplementary Search Report completed Nov. 3, 2016.
Castillo-Carranza, et al., "Tau aggregates as immunotherapeutic targets," *Frontiers in Bioscience, Scholar*, 5, 426-438 (Jan. 1, 2013).
Ghoshal, et al., "Tau Conformational Changes Correspond to Impairments of Episodic Memory in Mild Cognitive Impairment and Alzheimer's Disease," *Experimental Neurology*, 177, 475-493, (2002).
Jicha, et al., "Sequence Requirements for Formation of Conformational Variants of Tau Similar to Those Found in Alzheimer's Disease," *Journal of Neuroscience Research*, 55:713-723 (1999).
Morris, "Epitope Mapping of Protein Antigens by Competition ELISA," *The Protein Protocols Handbook*, edited by J. M. Walker, Humana Press Inc., Totowa, NJ, pp. 595-600, (Jan. 1, 1996).
Dubel, "Molecular Engineering I: Humanization," *Handbook of Therapeutic Antibodies*, Chapter 6:119-144, (2007).
Yanamandra, et al., "Anti-Tau Antibodies that Block Tau Aggregate Seeding In Vitro Markedly Decrease Pathology and Improve Cognition in Vivo," *Neuron*, 80, 402-414 (Oct. 15, 2013).
PCT/US2014/025044 International Preliminary Report on Patentability completed Oct. 9, 2014.
U.S. Appl. No. 14/776,724 Restriction Requirement dated Jan. 19, 2017.
U.S. Appl. No. 14/776,724 Non-Final Office Action dated Jun. 1, 2017.
Chen, et al., "Enhancement and destruction of anitbody function by somatic mutation: unequal occurrence is controlled by V gene combinatorial associations," *the EMBO Journal*, vol. 14, No. 12, pp. 2784-2794 (1995).
Kussie, et al., "A Single Engineered Amino Acid Substitution Changes Antibody Fine Specificity," *J Immunol*, 152(1):146-52 (1994).
Oddo, et al., "Reduction of Soluble Aβ and Tau, but Not Soluble Aβ Alone, Ameliorates Cognitive Decline in Transgenic Mice with Plaques and Tangles," *The Journal of Biological Chemistry*, vol. 281, No. 51, pp. 39413-39423 (Dec. 22, 2016).
Hasegawa, et al., "Characterization of Two distinct Monoclonal Antibodies to Paired Helical Filaments: Further Evidence for Fetal-Type Phosphorylation of the τ in Paired Helical Filaments", Journal of Neurochemistry, vol. 60, No. 6, (1993).
Leger, et al., "Antibody Drug Discovery Chapter 1: Humanization of Antibodies", Molecular medicine and Medicinal Chemistry, pp. 1-23 XP055119233 (Jan. 1, 2011).
Almagro, et al., "Humanization of antibodies", *Frontiers in Bioscience*, 13, 1619-1653, (Jan. 1, 2008).
Lazar, et al., "A molecular immunology approach to antibody humanization and functional optimization", *Molecular Immunology*, 44:1986-1998 (2007).
Wu, et al., "Simultaneous Humanization and Affinity Optinization of Monoclonal Antibodies", *Methods of Molecular Biology*, vol. 207: Recombinant Antibodies for Cancer Therapy: Methods and

(56) References Cited

OTHER PUBLICATIONS

Protocols, Edited by M. Weischof and J. Krauss @ Humana Press Inc., Tolowa NJ, pp. 197-212 (Jan. 1, 2003).
PCT/IB2017/052544 Search Report and Written Opinion dated Jul. 31, 2017.
PCT/IB2017/052545 Search Report and Written Opinion dated Aug. 1, 2017.
Bacskai, et al., "Imaging of amyloid-β deposits in brains of living mice permits direct observation of clearance of plaques with immunotherapy," *Nature Medicine*, vol. 7, No. 3, pp. 369-372, (Mar. 2001).
PCT/IB2017/052544 Search Report and Written Opinion dated Jul. 19, 2017.
Agadjanyan, et al., "Humanized monoclonal antibody armanezumab specific to N-terminus of pathological tau: characterization and therapeutic potency," *Molecular Neurodegeneration*, 12:33, DOI 10.1186/s13024-017-0172-1, (2017).
Kontsekova, et al., "First-in-man tau vaccine targeting structural determinants essential for pathological tau-tau interaction reduces tau oligomerisation and neurofibrillary degeneration in an Alzheimer's disease model," *Alzheimer's Research & Therapy*, 6:44, (2014).
Rosseels, et al., "Tau Monoclonal Antibody Generation Based on Humanized Yeast Models," *Journal of Biological Chemistry*, vol. 290, No. 7, pp. 4059-4074, (Dec. 24, 2014).
PCT/IB2017/052543 International Report on Patentability dated Nov. 6, 2018.
PCT/IB2017/052544 International Report on Patentability dated Nov. 6, 2018.
PCT/IB2017/052545 International Report on Patentability dated Nov. 6, 2018.
U.S. Appl. No. 14/776,724 Notice of Allowance dated Jul. 29, 2019.
U.S. Appl. No. 16/091,060 Restriction Requirement dated Sep. 17, 2019.
U.S. Appl. No. 16/092,439 Notice of Allowance dated Oct. 16, 2019.
Pedersen, et al., "Tau immunotherapy for Alzheimer's disease," *Trends in Molecular Medicine*, vol. 21, No. 6, pp. 394-402, (Jun. 2015).
PCT/US2018/030739 International Preliminary Report on Patentability dated Nov. 5, 2019.
U.S. Appl. No. 16/091,060 Non-Final Office Action dated Feb. 21, 2020.
U.S. Appl. No. 16/092,439 Notice of Allowance and Interview Summary dated Apr. 10, 2020.
PCT/US2019/060616 International Search Report and Written Opinion dated Mar. 20, 2020.
PCT/US2020/017357 Invitation to Pay Additional Fees dated Apr. 23, 2020.
PCT/US2020/017357 International Search Report and Written Opinion dated Jun. 17, 2020.
Kawahara, et al., "The Novel Monoclonal Antibody 9F5 Reveals Expression of a Fragment of GPNMB/Osteoactivin Processed by Furin-like Protease(s) in a Subpopulation of Microglia in Neonatal Rat Brain," *GLIA*, vol. 64, No. 11, pp. 1938-1961, (Nov. 2016).
Strang, et al., "Generation and characterization of new monoclonal antibodies targeting the PHF1 and AT8 epitopes on human tau," *Acta Neuropathologica Communications*, 5:58, (2017).
Croft, et al., "Novel monoclonal antibodies targeting the microtubule-binding domain of human tau," *PLoS ONE*, 13(4): e0195211, (2018).
PCT/US2020/020704 Invitation to Pay Additional Fees dated Jun. 3, 2020.
EP 19213368 Extended European Search Report dated Jun. 24, 2020.
Florenzano, et al., "Extracellular truncated tau causes early presynaptic dysfunction associated with Alzheimer's disease and other tauopathies," *Oncotarget*, vol. 8, No. 29, pp. 64745-46778, (2017).
Gershoni, et al., "Epitope Mapping, The First Step in Developing Epitope-Based Vaccines," *Biodrugs*, 21:(3), p. 145-156. (2007).
PCT/US2020/020704 Search Report and Written Opinion dated Aug. 4, 2020.
U.S. Appl. No. 16/091,060 Notice of Allowance and Interview Summary dated Aug. 19, 2020.

Alignments of the 16G7 mouse/humanized VH:

```
                   10         20         30         40         50         60
Majority     EVQLXQXGAEXVKPGASVKXSCKASGYTFTSSWIHWVRQRPGQGLEWIGEIYPNSGNTNY 16G7 VH protein      EVQLQQPGSVLMPGASVKLSCKASGYTFTSSWIHWVRQRPGQGLEWIGEIYPNSGNTNY   60  SEQ ID NO:52
hu16G7VHv1 protein   EVQLQQPGSVLMPGASVKLSCKASGYTFTSSWIHWVRQRPGQGLEWIGEIYPNSGNTNY   60  SEQ ID NO:7
hu16G7VHv2 protein   EVQLQQSGAEVKKPGASVKLSCKASGYTFTSSWIHWVRQAPGQGLEWIGEIYPNSGNTNY  60  SEQ ID NO:15
h16G7VHv2a protein   EVQLMQSGAEVKKPGASVKVSCKASGYTFTSSWIHWVRQAPGQGLEWIGEIYPNSGNTNY  60  SEQ ID NO:16
h16G7VHv2aB7 protein EVQLMQSGAEVKKPGASVKVSCKASGYTFTSSWIHWVRQAPGQGLEWIGEIYPNSGNTNY  60  SEQ ID NO:17
h16G7VHv2b protein   EVQLMQSGAEVKKPGASVKVSCKASGYTFTSSWIHWVRQAPGQGLEWIGEIYPNSGNTNY  60  SEQ ID NO:18
h16G7VHv2bH7 protein EVQLMQSGAEVKKPGASVKVSCKASGYTFTSSWIHWVRQAPGQGLEWIGEIYPNSGNTNY  60  SEQ ID NO:19
h16G7VHv3 protein    EVQLQQPGSVLMPGASVKLSCKASGYTFTSSWIHWVRQRPGQGLEWIGEIYPNSGNTNY   60  SEQ ID NO:20
h16G7VHv4 protein    EVQLQQSGAELVKPGASVKLSCKASGYTFTSSWIHWVRQRPGQGLEWIGEIYPNSGNTNY  60  SEQ ID NO:21
h16G7VHv5V protein   EVQLQQPGSVLMPGASVKLSCKASGYTFTSSWIHWVRQAPGQGLEWIGEIYPNSGNTNY   60  SEQ ID NO:22
h16G7VHv5VR protein  EVQLQQPGSVLMPGASVKLSCKASGYTFTSSWIHWVRQRPGQGLEWIGEIYPNSGNTNY   60  SEQ ID NO:23
h16G7VHv6a protein   EVQLVQSGAEVKKPGASVKVSCKASGYTFTSSWIHWVRQAPGQGLEWMGEIYPNSGNTNY  60  SEQ ID NO:24
h16G7VHv6b protein   EVQLVQSGAEVKKPGASVKVSCKASGYTFTSSWIHWVRQAPGQGLEWMGEIYPNSGNTNY  60  SEQ ID NO:25
h16G7VHv7 protein    EVQLVQSGAEVKKPGASVKVSCKASGYTFTSSWIHWVRQAPGQGLEWMGEIYPNSGNTNY  60  SEQ ID NO:26
                                                                                  SEQ ID NO:27

70         80         90        100        110
Majority     NEKFKGXXTLTVDISISTAYMELKXLTSKDTAVYYCARLGWLIPLDYWGQGTTVTVSS 16G7 VH protein      NEKFKGKATLTVDISISTAYMELSSLTSEDTAVYYCARLGWLIPLDYWGQGTTVTVSS   118
hu16G7VHv1 protein   NEKFKGKATLTVDISISTAYMELSSLTSEDTAVYYCARLGWLIPLDYWGQGTTVTVSS   118
hu16G7VHv2 protein   NEKFKGRVTLTVDISISTAYMELSSLTSEDTAVYYCARLGWLIPLDYWGQGTTVTVSS   118
h16G7VHv2a protein   NEKFKGKATLTVDISISTAYMELSRLTSEDTAVYYCARLGWLIPLDYWGQGTTVTVSS   118
h16G7VHv2aB7 protein AEKFKGKATLTVDISISTAYMELSRLTSEDTAVYYCARLGWLIPLDYWGQGTTVTVSS   118
h16G7VHv2b protein   NEKFKGRVTLTRDISISTAYMELSRLTSEDTAVYYCARLGWLIPLDYWGQGTTVTVSS   118
h16G7VHv2bH7 protein AEKFKGRVTLTRDISISTAYMELSRLTSEDTAVYYCARLGWLIPLDYWGQGTTVTVSS   118
h16G7VHv3 protein    NEKFKGKATLTVDISISTAYMELSSLTSEDTAVYYCARLGWLIPLDYWGQGTTVTVSS   118
h16G7VHv4 protein    NEKFKGRVTLTVDISASTAYMELSSLTSEDTAVYYCARLGWLIPLDYWGQGTTVTVSS   118
h16G7VHv5V protein   NEKFKGRVTLTVDISISTAYMELSSLTSEDTAVYYCARLGWLIPLDYWGQGTTVTVSS   118
h16G7VHv5VR protein  NEKFKGKATLTVDISISTAYMELSSLTSEDTAVYYCARLGWLIPLDYWGQGTTVTVSS   118
h16G7VHv6a protein   NEKFKGRVTMTVDTSISTAYMELSLASRLRSEDTAVYYCARLGWLIPLDYWGQGTTVTVSS 118
h16G7VHv6b protein   NEKFKGRVTMTVDTSISTAYMELSRLRSEDTAVYYCARLGWLIPLDYWGQGTTVTVSS   118
h16G7VHv7 protein    NEKFKGRVTLTVDTSISTAYMELSRLRSEDTAVYYCARLGWLIPLDYWGQGTTVTVSS   118
```

FIG. 2

| 16G7 | $k_{assoc}$ | $k_{dissoc}$ | $K_d$ |
|---|---|---|---|
| Human tau | 1.64E6 | 5.63E-4 | 3.42E-10 |

| Name | $k_a (M^{-1}s^{-1})$ | $k_d (s^{-1})$ | $k_D (pM)$ |
|---|---|---|---|
| hu16G7VHv2a /hu16G7VLv2 | $3 \times 10^6$ | $8.33 \times 10^{-4}$ | 277 |
| hu16G7VHv2b/hu16G7VLv2 | $3.52 \times 10^6$ | $1.07 \times 10^{-3}$ | 303 |
| hu16G7VHv7/hu16G7VLv2 | $4.89 \times 10^6$ | $1.43 \times 10^{-3}$ | 293 |
| Chimeric | $2.9 \times 10^6$ | $5.4 \times 10^{-4}$ | 187 |

FIGURE 8A

| Kabat residue # | Linear residue # | FR or CDR | Murine 16G7 VL (SEQ ID NO: 11) | Hu VL Acceptor Fr Acc. # IMGT#IGKV4-1*01 (SEQ ID NO:36) | Hu16G7VLv1 (SEQ ID NO:28) | Hu16G7VLv2 (SEQ ID NO:29) | Hu16G7VLv3 (SEQ ID NO:30) |
|---|---|---|---|---|---|---|---|
| 1 | 1 | Fr1 | D | D | D | D | D |
| 2 | 2 | Fr1 | I | I | I | I | I |
| 3 | 3 | Fr1 | V | V | V | V | V |
| 4 | 4 | Fr1 | L | M | L | L | L |
| 5 | 5 | Fr1 | S | T | T | T | T |
| 6 | 6 | Fr1 | Q | Q | Q | Q | Q |
| 7 | 7 | Fr1 | S | S | S | S | S |
| 8 | 8 | Fr1 | P | P | P | P | P |
| 9 | 9 | Fr1 | S | D | S | S | S |
| 10 | 10 | Fr1 | S | S | S | S | S |
| 11 | 11 | Fr1 | L | L | L | L | L |
| 12 | 12 | Fr1 | A | A | A | A | A |
| 13 | 13 | Fr1 | V | V | V | V | V |
| 14 | 14 | Fr1 | S | S | S | S | S |
| 15 | 15 | Fr1 | V | L | V | V | V |
| 16 | 16 | Fr1 | G | G | G | G | G |
| 17 | 17 | Fr1 | E | E | E | E | E |
| 18 | 18 | Fr1 | K | R | K | R | K |
| 19 | 19 | Fr1 | V | A | V | A | V |
| 20 | 20 | Fr1 | T | T | T | T | T |
| 21 | 21 | Fr1 | M | I | M | I | M |
| 22 | 22 | Fr1 | S | N | S | S | S |
| 23 | 23 | Fr1 | C | C | C | C | C |
| 24 | 24 | CDR-L1 | K | K | K | K | K |
| 25 | 25 | CDR-L1 | S | S | S | S | S |
| 26 | 26 | CDR-L1 | S | S | S | S | S |
| 27 | 27 | CDR-L1 | Q | Q | Q | Q | Q |
| 27A | 28 | CDR-L1 | S | S | S | S | S |
| 27B | 29 | CDR-L1 | L | V | L | L | L |
| 27C | 30 | CDR-L1 | L | L | L | L | L |
| 27D | 31 | CDR-L1 | D | Y | D | D | D |
| 27E | 32 | CDR-L1 | G | S | G | G | G |

FIGURE 8B

| Kabat residue # | Linear residue # | FR or CDR | Murine 16G7 VL (SEQ ID NO: 11) | Hu VL Acceptor Fr Acc. # IMGT#IGKV4-1*01 (SEQ ID NO:36) | Hu16G7VLv1 (SEQ ID NO:28) | Hu16G7VLv2 (SEQ ID NO:29) | Hu16G7VLv3 (SEQ ID NO:30) |
|---|---|---|---|---|---|---|---|
| 27F | 33 | CDR-L1 | N | S | N | N | N |
| 28 | 34 | CDR-L1 | D | N | D | D | D |
| 29 | 35 | CDR-L1 | Q | N | Q | Q | Q |
| 30 | 36 | CDR-L1 | K | K | K | K | K |
| 31 | 37 | CDR-L1 | N | N | N | N | N |
| 32 | 38 | CDR-L1 | Y | Y | Y | Y | Y |
| 33 | 39 | CDR-L1 | L | L | L | L | L |
| 34 | 40 | CDR-L1 | A | A | A | A | A |
| 35 | 41 | Fr2 | W | W | W | W | W |
| 36 | 42 | Fr2 | Y | Y | Y | Y | Y |
| 37 | 43 | Fr2 | Q | Q | Q | Q | Q |
| 38 | 44 | Fr2 | Q | Q | Q | Q | Q |
| 39 | 45 | Fr2 | K | K | K | K | K |
| 40 | 46 | Fr2 | P | P | P | P | P |
| 41 | 47 | Fr2 | G | G | G | G | G |
| 42 | 48 | Fr2 | Q | Q | Q | Q | Q |
| 43 | 49 | Fr2 | S | P | S | S | S |
| 44 | 50 | Fr2 | P | P | P | P | P |
| 45 | 51 | Fr2 | K | K | K | K | K |
| 46 | 52 | Fr2 | L | L | L | L | L |
| 47 | 53 | Fr2 | L | L | L | L | L |
| 48 | 54 | Fr2 | M | I | M | I | I |
| 49 | 55 | Fr2 | Y | Y | Y | Y | Y |
| 50 | 56 | CDR-L2 | W | W | W | W | W |
| 51 | 57 | CDR-L2 | A | A | A | A | A |
| 52 | 58 | CDR-L2 | S | S | S | S | S |
| 53 | 59 | CDR-L2 | T | T | T | T | T |
| 54 | 60 | CDR-L2 | R | R | R | R | R |
| 55 | 61 | CDR-L2 | E | E | E | E | E |
| 56 | 62 | CDR-L2 | S | S | S | S | S |
| 57 | 63 | Fr3 | G | G | G | G | G |
| 58 | 64 | Fr3 | V | V | V | V | V |
| 59 | 65 | Fr3 | P | P | P | P | P |

FIGURE 8C

| Kabat residue # | Linear residue # | FR or CDR | Murine 16G7 VL (SEQ ID NO: 11) | Hu VL Acceptor Fr Acc. # IMGT#IGKV4-1*01 (SEQ ID NO:36) | Hu16G7VLv1 (SEQ ID NO:28) | Hu16G7VLv2 (SEQ ID NO:29) | Hu16G7VLv3 (SEQ ID NO:30) |
|---|---|---|---|---|---|---|---|
| 60 | 66 | Fr3 | D | D | D | D | D |
| 61 | 67 | Fr3 | R | R | R | R | R |
| 62 | 68 | Fr3 | F | F | F | F | F |
| 63 | 69 | Fr3 | T | S | S | S | S |
| 64 | 70 | Fr3 | G | G | G | G | G |
| 65 | 71 | Fr3 | S | S | S | S | S |
| 66 | 72 | Fr3 | G | G | G | G | G |
| 67 | 73 | Fr3 | S | S | S | S | S |
| 68 | 74 | Fr3 | G | G | G | G | G |
| 69 | 75 | Fr3 | T | T | T | T | T |
| 70 | 76 | Fr3 | D | D | D | D | D |
| 71 | 77 | Fr3 | F | F | F | F | F |
| 72 | 78 | Fr3 | T | T | T | T | T |
| 73 | 79 | Fr3 | L | L | L | L | L |
| 74 | 80 | Fr3 | T | T | T | T | T |
| 75 | 81 | Fr3 | I | I | I | I | I |
| 76 | 82 | Fr3 | S | S | S | S | S |
| 77 | 83 | Fr3 | S | S | S | S | S |
| 78 | 84 | Fr3 | L | L | L | L | L |
| 79 | 85 | Fr3 | K | Q | Q | Q | Q |
| 80 | 86 | Fr3 | A | A | A | A | A |
| 81 | 87 | Fr3 | E | E | E | E | E |
| 82 | 88 | Fr3 | D | D | D | D | D |
| 83 | 89 | Fr3 | L | V | V | V | V |
| 84 | 90 | Fr3 | A | A | A | A | A |
| 85 | 91 | Fr3 | V | V | V | V | V |
| 86 | 92 | Fr3 | Y | Y | Y | Y | Y |
| 87 | 93 | Fr3 | Y | Y | Y | Y | Y |
| 88 | 94 | Fr3 | C | C | C | C | C |
| 89 | 95 | CDR-L3 | Q | Q | Q | Q | Q |
| 90 | 96 | CDR-L3 | Q | Q | Q | Q | Q |
| 91 | 97 | CDR-L3 | F | Y | F | F | F |
| 92 | 98 | CDR-L3 | Y | Y | Y | Y | Y |

FIGURE 8D

| Kabat residue # | Linear residue # | FR or CDR | Murine 16G7 VL (SEQ ID NO: 11) | Hu VL Acceptor Fr Acc. # IMGT#IGKV4-1*01 (SEQ ID NO:36) | Hu16G7VLv1 (SEQ ID NO:28) | Hu16G7VLv2 (SEQ ID NO:29) | Hu16G7VLv3 (SEQ ID NO:30) |
|---|---|---|---|---|---|---|---|
| 93 | 99 | CDR-L3 | D | S | D | D | D |
| 94 | 100 | CDR-L3 | Y | T | Y | Y | Y |
| 95 | 101 | CDR-L3 | P | P | P | P | P |
| 95A | | CDR-L3 | | | | | |
| 95B | | CDR-L3 | | | | | |
| 95C | | CDR-L3 | | | | | |
| 95D | | CDR-L3 | | | | | |
| 95E | | CDR-L3 | | | | | |
| 95F | | CDR-L3 | | | | | |
| 96 | 102 | CDR-L3 | W | | W | W | W |
| 97 | 103 | CDR-L3 | T | | T | T | T |
| 98 | 104 | Fr4 | F | | F | F | F |
| 99 | 105 | Fr4 | G | | G | G | G |
| 100 | 106 | Fr4 | G | | G | G | G |
| 101 | 107 | Fr4 | G | | G | G | G |
| 102 | 108 | Fr4 | T | | T | T | T |
| 103 | 109 | Fr4 | K | | K | K | K |
| 104 | 110 | Fr4 | L | | L | L | L |
| 105 | 111 | Fr4 | E | | E | E | E |
| 106 | 112 | Fr4 | I | | I | I | I |
| 106A | 113 | Fr4 | K | | K | K | K |
| 107 | 114 | Fr4 | R | | R | R | R |

FIGURE 9A

| Kabat residue # | Linear residue # | FR or CDR | Murine 16G7 VH (SEQ ID NO: 7) | Hu VH Acceptor FR Acc. # IMGT# IGHV1-2*02 (SEQ ID NO: 33) | hu16G7VHv1 (SEQ ID NO:15) | hu16G7VHv2 (SEQ ID NO:16) | hu16G7VHv2a (SEQ ID NO:17) | 16G7VHv2aB7 (SEQ ID NO:18) | hu16G7VHv2b (SEQ ID NO:19) | hu16G7VHv2bH7 (SEQ ID NO: 20) | hu16G7VHv3 (SEQ ID NO:21) | hu16G7VHv4 (SEQ ID NO:22) | hu16G7VHv5V (SEQ ID NO:23) | hu16G7VHv5VR (SEQ ID NO:24) | hu16G7VHv6a (SEQ ID NO:25) | hu16G7VHv6b (SEQ ID NO:26) | hu16G7VHv7 (SEQ ID NO:27) |
|---|---|---|---|---|---|---|---|---|---|---|---|---|---|---|---|---|---|
| 1 | 1 | Fr1 | Q | Q | E | E | E | E | E | E | E | E | E | E | Q | Q | E |
| 2 | 2 | Fr1 | V | V | V | V | V | V | V | V | V | V | V | V | V | V | V |
| 3 | 3 | Fr1 | Q | Q | Q | Q | Q | Q | Q | Q | Q | Q | Q | Q | Q | Q | Q |
| 4 | 4 | Fr1 | L | L | L | L | L | L | L | L | L | L | L | L | L | L | L |
| 5 | 5 | Fr1 | Q | V | Q | Q | V | V | V | V | Q | Q | Q | Q | V | V | V |
| 6 | 6 | Fr1 | Q | Q | Q | Q | Q | Q | Q | Q | Q | Q | Q | Q | Q | Q | Q |
| 7 | 7 | Fr1 | P | S | P | S | S | S | S | S | P | S | P | P | P | S | P |
| 8 | 8 | Fr1 | G | G | G | G | G | G | G | G | G | G | G | G | G | G | G |
| 9 | 9 | Fr1 | S | A | S | A | A | A | A | S | A | S | S | S | A | A | A |
| 10 | 10 | Fr1 | V | E | V | E | E | E | E | E | V | E | V | V | E | E | E |
| 11 | 11 | Fr1 | L | V | L | L | V | V | V | V | L | L | L | L | V | V | V |
| 12 | 12 | Fr1 | V | K | V | V | V | V | V | V | V | V | V | V | K | K | K |
| 13 | 13 | Fr1 | R | K | R | K | K | K | K | K | R | K | R | R | K | K | K |
| 14 | 14 | Fr1 | P | P | P | P | P | P | P | P | P | P | P | P | P | P | P |
| 15 | 15 | Fr1 | G | G | G | G | G | G | G | G | G | G | G | G | G | G | G |
| 16 | 16 | Fr1 | A | A | A | A | A | A | A | A | A | A | A | A | A | A | A |
| 17 | 17 | Fr1 | S | S | S | S | S | S | S | S | S | S | S | S | S | S | S |
| 18 | 18 | Fr1 | V | V | V | V | V | V | V | V | V | V | V | V | V | V | V |
| 19 | 19 | Fr1 | K | K | K | K | K | K | K | K | K | K | K | K | K | K | K |
| 20 | 20 | Fr1 | L | V | L | L | V | V | V | V | L | L | L | L | V | V | V |
| 21 | 21 | Fr1 | S | S | S | S | S | S | S | S | S | S | S | S | S | S | S |
| 22 | 22 | Fr1 | C | C | C | C | C | C | C | C | C | C | C | C | C | C | C |
| 23 | 23 | Fr1 | K | K | K | K | K | K | K | K | K | K | K | K | K | K | K |
| 24 | 24 | Fr1 | A | A | A | A | A | A | A | A | A | A | A | A | A | A | A |
| 25 | 25 | Fr1 | S | S | S | S | S | S | S | S | S | S | S | S | S | S | S |
| 26 | 26 | Fr1 | G | G | G | G | G | G | G | G | G | G | G | G | G | G | G |
| 27 | 27 | Fr1 | Y | Y | Y | Y | Y | Y | Y | Y | Y | Y | Y | Y | Y | Y | Y |

FIGURE 9B

| Kabat residue # | Linear residue # | FR or CDR | Murine 16G7 VH (SEQ ID NO: 7) | Hu VH Acceptor FR Acc. # IMGT# IGHV1-2*02 (SEQ ID NO: 33) | hu16G7VHv1 (SEQ ID NO:15) | hu16G7VHv2 (SEQ ID NO:16) | hu16G7VHv2a (SEQ ID NO:17) | 16G7VHv2aB7 (SEQ ID NO:18) | hu16G7VHv2b (SEQ ID NO:19) | hu16G7VHv2bH7 (SEQ ID NO: 20) | hu16G7VHv3 (SEQ ID NO:21) | hu16G7VHv4 (SEQ ID NO:22) | hu16G7VHv5V (SEQ ID NO:23) | hu16G7VHv5VR (SEQ ID NO:24) | hu16G7VHv6a (SEQ ID NO:25) | hu16G7VHv6b (SEQ ID NO:26) | hu16G7VHv7 (SEQ ID NO:27) |
|---|---|---|---|---|---|---|---|---|---|---|---|---|---|---|---|---|---|
| 28 | 28 | Fr1 | T | T | T | T | T | T | T | T | T | T | T | T | T | T | T |
| 29 | 29 | Fr1 | F | F | F | F | F | F | F | F | F | F | F | F | F | F | F |
| 30 | 30 | Fr1 | T | T | T | T | T | T | T | T | T | T | T | T | T | T | T |
| 31 | 31 | CDR-H1 | S | G | S | S | S | G | S | G | S | S | S | S | S | S | S |
| 32 | 32 | CDR-H1 | S | Y | S | S | S | S | S | S | S | S | S | S | S | S | S |
| 33 | 33 | CDR-H1 | W | Y | W | W | W | W | W | W | W | W | W | W | W | W | W |
| 34 | 34 | CDR-H1 | I | M | I | I | I | I | I | I | I | I | I | I | I | I | I |
| 35 | 35 | CDR-H1 | H | H | H | H | H | H | H | H | H | H | H | H | H | H | H |
| 35A | | CDR-H1 | | | | | | | | | | | | | | | |
| 35B | | CDR-H1 | | | | | | | | | | | | | | | |
| 36 | 36 | Fr2 | W | W | W | W | W | W | W | W | W | W | W | W | W | W | W |
| 37 | 37 | Fr2 | A | V | A | V | V | V | V | V | V | V | V | V | V | V | V |
| 38 | 38 | Fr2 | K | R | K | R | R | R | R | R | R | R | K | R | R | R | R |
| 39 | 39 | Fr2 | Q | Q | Q | Q | Q | Q | Q | Q | Q | Q | Q | Q | Q | Q | Q |
| 40 | 40 | Fr2 | R | A | R | A | R | R | R | R | A | A | R | R | A | A | A |
| 41 | 41 | Fr2 | P | P | P | P | P | P | P | P | P | P | P | P | P | P | P |
| 42 | 42 | Fr2 | G | G | G | G | G | G | G | G | G | G | G | G | G | G | G |
| 43 | 43 | Fr2 | Q | Q | Q | Q | Q | Q | Q | Q | Q | Q | Q | Q | Q | Q | Q |
| 44 | 44 | Fr2 | G | G | G | G | G | G | G | G | G | G | G | G | G | G | G |
| 45 | 45 | Fr2 | L | L | L | L | L | L | L | L | L | L | L | L | L | L | L |
| 46 | 46 | Fr2 | E | E | E | E | E | E | E | E | E | E | E | E | E | E | E |
| 47 | 47 | Fr2 | W | W | W | W | W | W | W | W | W | W | W | W | W | W | W |
| 48 | 48 | Fr2 | I | M | I | I | I | I | I | I | I | I | I | I | M | M | M |
| 49 | 49 | Fr2 | G | G | G | G | G | G | G | G | G | G | G | G | G | G | G |
| 50 | 50 | CDR-H2 | E | W | E | E | E | E | E | E | E | E | E | E | E | E | E |
| 51 | 51 | CDR-H2 | I | I | I | I | I | I | I | I | I | I | I | I | I | I | I |
| 52 | 52 | CDR-H2 | Y | N | Y | Y | Y | Y | Y | Y | Y | Y | Y | Y | Y | Y | Y |

FIGURE 9C

| Kabat residue # | Linear residue # | FR or CDR | Murine 16G7 VH (SEQ ID NO: 7) | Hu VH Acceptor FR Acc. # IMGT# IGHV1-2*02 (SEQ ID NO: 33) | hu16G7VHv1 (SEQ ID NO:15) | hu16G7VHv2 (SEQ ID NO:16) | hu16G7VHv2a (SEQ ID NO:17) | 16G7VHv2aB7 (SEQ ID NO:18) | hu16G7VHv2b (SEQ ID NO:19) | hu16G7VHv2bH7 (SEQ ID NO: 20) | hu16G7VHv3 (SEQ ID NO:21) | hu16G7VHv4 (SEQ ID NO:22) | hu16G7VHv5V (SEQ ID NO:23) | hu16G7VHv5VR (SEQ ID NO:24) | hu16G7VHv6a (SEQ ID NO:25) | hu16G7VHv6b (SEQ ID NO:26) | hu16G7VHv7 (SEQ ID NO:27) |
|---|---|---|---|---|---|---|---|---|---|---|---|---|---|---|---|---|---|
| 52A | 53 | CDR-H2 | P | P | P | P | P | P | P | P | P | P | P | P | P | P | P |
| 52B | | | | | | | | | | | | | | | | | |
| 52C | | | | | | | | | | | | | | | | | |
| 53 | 54 | CDR-H2 | N | N | N | N | N | N | N | N | N | N | N | N | N | N | N |
| 54 | 55 | CDR-H2 | S | S | S | S | S | S | S | S | S | S | S | S | S | S | S |
| 55 | 56 | CDR-H2 | G | G | G | G | G | G | G | G | G | G | G | G | G | G | G |
| 56 | 57 | CDR-H2 | N | G | N | N | N | N | N | N | N | N | N | N | N | N | N |
| 57 | 58 | CDR-H2 | T | T | T | T | T | T | T | T | T | T | T | T | T | T | T |
| 58 | 59 | CDR-H2 | N | N | N | N | N | N | N | N | N | N | N | N | N | N | N |
| 59 | 60 | CDR-H2 | Y | Y | Y | Y | Y | Y | Y | Y | Y | Y | Y | Y | Y | Y | Y |
| 60 | 61 | CDR-H2 | N | A | N | N | N | A | N | A | N | N | N | N | N | N | N |
| 61 | 62 | CDR-H2 | E | Q | E | E | E | E | E | E | E | E | E | E | E | E | E |
| 62 | 63 | Fr3 | K | K | K | K | K | K | K | K | K | K | K | K | K | K | K |
| 63 | 64 | Fr3 | F | F | F | F | F | F | F | F | F | F | F | F | F | F | F |
| 64 | 65 | Fr3 | K | Q | K | K | K | K | K | Q | K | K | K | K | K | K | K |
| 65 | 66 | Fr3 | G | G | G | G | G | G | G | G | G | G | G | G | G | G | G |
| 66 | 67 | Fr3 | K | R | K | R | K | K | R | R | R | K | K | K | R | R | R |
| 67 | 68 | Fr3 | A | V | A | V | A | A | V | V | V | A | A | A | V | V | V |
| 68 | 69 | Fr3 | T | T | T | T | T | T | T | T | T | T | T | T | T | T | T |
| 69 | 70 | Fr3 | L | M | L | L | L | L | L | L | L | L | L | L | M | M | M |
| 70 | 71 | Fr3 | T | T | T | T | T | T | T | T | T | T | T | T | T | T | T |
| 71 | 72 | Fr3 | V | R | V | V | V | V | R | R | V | V | V | V | V | V | V |
| 72 | 73 | Fr3 | D | D | D | D | D | D | D | D | D | D | D | D | D | D | D |
| 73 | 74 | Fr3 | I | T | I | T | I | I | I | I | T | I | I | I | I | T | I |
| 74 | 75 | Fr3 | S | S | S | S | S | S | S | S | S | S | S | S | S | S | S |
| 75 | 76 | Fr3 | S | I | S | A | I | I | I | I | A | S | S | S | I | I | I |
| 76 | 77 | Fr3 | S | S | S | S | S | S | S | S | S | S | S | S | S | S | S |

FIGURE 9D

| Kabat residue # | Linear residue # | FR or CDR | Murine 16G7 VH (SEQ ID NO: 7) | Hu VH Acceptor FR Acc. # IMGT# IGHV1-2*02 (SEQ ID NO: 33) | hu16G7VHv1 (SEQ ID NO:15) | hu16G7VHv2 (SEQ ID NO:16) | hu16G7VHv2a (SEQ ID NO:17) | 16G7VHv2aB7 (SEQ ID NO:18) | hu16G7VHv2b (SEQ ID NO:19) | hu16G7VHv2bH7 (SEQ ID NO: 20) | hu16G7VHv3 (SEQ ID NO:21) | hu16G7VHv4 (SEQ ID NO:22) | hu16G7VHv5V (SEQ ID NO:23) | hu16G7VHv5VR (SEQ ID NO:24) | hu16G7VHv6a (SEQ ID NO:25) | hu16G7VHv6b (SEQ ID NO:26) | hu16G7VHv7 (SEQ ID NO:27) |
|---|---|---|---|---|---|---|---|---|---|---|---|---|---|---|---|---|---|
| 77 | 78 | Fr3 | T | T | T | T | T | T | T | T | T | T | T | T | T | T | T |
| 78 | 79 | Fr3 | A | A | A | A | A | A | A | A | A | A | A | A | A | A | A |
| 79 | 80 | Fr3 | Y | Y | Y | Y | Y | Y | Y | Y | Y | Y | Y | Y | Y | Y | Y |
| 80 | 81 | Fr3 | V | M | V | M | M | M | M | M | M | M | V | V | M | M | M |
| 81 | 82 | Fr3 | D | E | E | E | E | E | E | E | E | E | E | E | E | E | E |
| 82 | 83 | Fr3 | L | L | L | L | L | L | L | L | L | L | L | L | L | L | L |
| 82A | 84 | Fr3 | T | S | T | T | S | S | S | S | T | T | T | T | S | S | S |
| 82B | 85 | Fr3 | S | R | S | S | R | R | R | R | S | S | S | S | R | R | R |
| 82C | 86 | Fr3 | L | L | L | L | L | L | L | L | L | L | L | L | L | L | L |
| 83 | 87 | Fr3 | T | R | T | T | T | T | T | T | T | T | T | T | R | R | R |
| 84 | 88 | Fr3 | S | S | S | S | S | S | S | S | S | S | S | S | S | S | S |
| 85 | 89 | Fr3 | E | D | E | E | D | D | D | D | E | E | E | E | D | D | D |
| 86 | 90 | Fr3 | D | D | D | D | D | D | D | D | D | D | D | D | D | D | D |
| 87 | 91 | Fr3 | S | T | S | T | T | T | T | T | T | T | T | T | T | T | T |
| 88 | 92 | Fr3 | A | A | A | A | A | A | A | A | A | A | A | A | A | A | A |
| 89 | 93 | Fr3 | V | V | V | V | V | V | V | V | V | V | V | V | V | V | V |
| 90 | 94 | Fr3 | Y | Y | Y | Y | Y | Y | Y | Y | Y | Y | Y | Y | Y | Y | Y |
| 91 | 95 | Fr3 | Y | Y | Y | Y | Y | Y | Y | Y | Y | Y | Y | Y | Y | Y | Y |
| 92 | 96 | Fr3 | C | C | C | C | C | C | C | C | C | C | C | C | C | C | C |
| 93 | 97 | Fr3 | A |   | A | A | A | A | A | A | A | A | A | A | A | A | A |
| 94 | 98 | CDR-H3 | R |   | R | R | R | R | R | R | R | R | R | R | R | R | R |
| 95 | 99 | CDR-H3 | L |   | L | L | L | L | L | L | L | L | L | L | L | L | L |
| 96 | 100 | CDR-H3 | G |   | G | G | G | G | G | G | G | G | G | G | G | G | G |
| 97 | 101 | CDR-H3 | W |   | W | W | W | W | W | W | W | W | W | W | W | W | W |
| 98 | 102 | CDR-H3 | L |   | L | L | L | L | L | L | L | L | L | L | L | L | L |
| 99 | 103 | CDR-H3 | I |   | I | I | I | I | I | I | I | I | I | I | I | I | I |
| 100 | 104 | CDR-H3 | P |   | P | P | P | P | P | P | P | P | P | P | P | P | P |

FIGURE 9E

| Kabat residue # | Linear residue # | FR or CDR | Murine 16G7 VH (SEQ ID NO: 7) | Hu VH Acceptor FR Acc. # IMGT# IGHV1-2*02 (SEQ ID NO: 33) | hu16G7VHv1 (SEQ ID NO:15) | hu16G7VHv2 (SEQ ID NO:16) | hu16G7VHv2a (SEQ ID NO:17) | 16G7VHv2aB7 (SEQ ID NO:18) | hu16G7VHv2b (SEQ ID NO:19) | hu16G7VHv2bH7 (SEQ ID NO: 20) | hu16G7VHv3 (SEQ ID NO:21) | hu16G7VHv4 (SEQ ID NO:22) | hu16G7VHv5V (SEQ ID NO:23) | hu16G7VHv5VR (SEQ ID NO:24) | hu16G7VHv6a (SEQ ID NO:25) | hu16G7VHv6b (SEQ ID NO:26) | hu16G7VHv7 (SEQ ID NO:27) |
|---|---|---|---|---|---|---|---|---|---|---|---|---|---|---|---|---|---|
| 100A | 105 |  | L |  | L | L | L | L | L | L | L | L | L | L | L | L | L |
| 100B |  |  |  |  |  |  |  |  |  |  |  |  |  |  |  |  |  |
| 100C |  |  |  |  |  |  |  |  |  |  |  |  |  |  |  |  |  |
| 100D |  |  |  |  |  |  |  |  |  |  |  |  |  |  |  |  |  |
| 100E |  |  |  |  |  |  |  |  |  |  |  |  |  |  |  |  |  |
| 100F |  |  |  |  |  |  |  |  |  |  |  |  |  |  |  |  |  |
| 100G |  |  |  |  |  |  |  |  |  |  |  |  |  |  |  |  |  |
| 100H |  |  |  |  |  |  |  |  |  |  |  |  |  |  |  |  |  |
| 100I |  |  |  |  |  |  |  |  |  |  |  |  |  |  |  |  |  |
| 100J |  |  |  |  |  |  |  |  |  |  |  |  |  |  |  |  |  |
| 100K |  |  |  |  |  |  |  |  |  |  |  |  |  |  |  |  |  |
| 101 | 106 | CDR-H3 | D |  | D | D | D | D | D | D | D | D | D | D | D | D | D |
| 102 | 107 | CDR-H3 | Y |  | Y | Y | Y | Y | Y | Y | Y | Y | Y | Y | Y | Y | Y |
| 103 | 108 | Fr4 | W |  | W | W | W | W | W | W | W | W | W | W | W | W | W |
| 104 | 109 | Fr4 | G |  | G | G | G | G | G | G | G | G | G | G | G | G | G |
| 105 | 110 | Fr4 | Q |  | Q | Q | Q | Q | Q | Q | Q | Q | Q | Q | Q | Q | Q |
| 106 | 111 | Fr4 | G |  | G | G | G | G | G | G | G | G | G | G | G | G | G |
| 107 | 112 | Fr4 | T |  | T | T | T | T | T | T | T | T | T | T | T | T | T |
| 108 | 113 | Fr4 | T |  | T | T | T | T | T | T | T | T | T | T | T | T | T |
| 109 | 114 | Fr4 | L |  | V | V | V | V | V | V | V | V | V | V | V | V | V |
| 110 | 115 | Fr4 | I |  | T | T | T | T | T | T | T | T | T | T | T | T | T |
| 111 | 116 | Fr4 | V |  | V | V | V | V | V | V | V | V | V | V | V | V | V |
| 112 | 117 | Fr4 | S |  | S | S | S | S | S | S | S | S | S | S | S | S | S |
| 113 | 118 | Fr4 | S |  | S | S | S | S | S | S | S | S | S | S | S | S | S |

SEQUENCE LISTING

<160> NUMBER OF SEQ ID NOS: 55

<210> SEQ ID NO 1
<211> LENGTH: 441
<212> TYPE: PRT
<213> ORGANISM: Homo sapiens

<400> SEQUENCE: 1

Met Ala Glu Pro Arg Gln Glu Phe Glu Val Met Glu Asp His Ala Gly
1               5                   10                  15

```
Thr Tyr Gly Leu Gly Asp Arg Lys Asp Gln Gly Tyr Thr Met His
            20                  25                  30

Gln Asp Gln Glu Gly Asp Thr Asp Ala Gly Leu Lys Glu Ser Pro Leu
         35                  40                  45

Gln Thr Pro Thr Glu Asp Gly Ser Glu Glu Pro Gly Ser Glu Thr Ser
 50                  55                  60

Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Gln Pro His Thr Glu
             85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Lys Ala Lys Gly
            130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
            165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
            195                 200                 205

Arg Ser Arg Thr Pro Ser Leu Pro Thr Pro Pro Thr Arg Glu Pro Lys
210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
            245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
            275                 280                 285

Ser Lys Cys Gly Ser Lys Asp Asn Ile Lys His Val Pro Gly Gly Gly
            290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
            325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
            355                 360                 365

Lys Lys Ile Glu Thr His Lys Leu Thr Phe Arg Glu Asn Ala Lys Ala
            370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
            405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
```

```
              435                 440
```

<210> SEQ ID NO 2
<211> LENGTH: 412
<212> TYPE: PRT
<213> ORGANISM: Homo sapiens

<400> SEQUENCE: 2

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Pro Gly Ser Glu Thr Ser
    50                  55                  60

Asp Ala Lys Ser Thr Pro Thr Ala Glu Ala Glu Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Ile Asn Lys Lys Leu Asp Leu Ser
                245                 250                 255

Asn Val Gln Ser Lys Cys Gly Ser Lys Asp Asn Ile Lys His Val Pro
            260                 265                 270

Gly Gly Gly Ser Val Gln Ile Val Tyr Lys Pro Val Asp Leu Ser Lys
        275                 280                 285

Val Thr Ser Lys Cys Gly Ser Leu Gly Asn Ile His His Lys Pro Gly
    290                 295                 300

Gly Gly Gln Val Glu Val Lys Ser Glu Lys Leu Asp Phe Lys Asp Arg
305                 310                 315                 320

Val Gln Ser Lys Ile Gly Ser Leu Asp Asn Ile Thr His Val Pro Gly
                325                 330                 335

Gly Gly Asn Lys Lys Ile Glu Thr His Lys Leu Thr Phe Arg Glu Asn
            340                 345                 350

Ala Lys Ala Lys Thr Asp His Gly Ala Glu Ile Val Tyr Lys Ser Pro
        355                 360                 365
```

-continued

```
Val Val Ser Gly Asp Thr Ser Pro Arg His Leu Ser Asn Val Ser Ser
370                 375                 380

Thr Gly Ser Ile Asp Met Val Asp Ser Pro Gln Leu Ala Thr Leu Ala
385                 390                 395                 400

Asp Glu Val Ser Ala Ser Leu Ala Lys Gln Gly Leu
                405                 410

<210> SEQ ID NO 3
<211> LENGTH: 383
<212> TYPE: PRT
<213> ORGANISM: Homo sapiens

<400> SEQUENCE: 3

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Ala Glu Glu Ala
            35                  40                  45

Gly Ile Gly Asp Thr Pro Ser Leu Glu Asp Glu Ala Ala Gly His Val
        50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
                100                 105                 110

Ile Pro Ala Lys Thr Pro Pro Ala Pro Lys Thr Pro Pro Ser Ser Gly
            115                 120                 125

Glu Pro Pro Lys Ser Gly Asp Arg Ser Gly Tyr Ser Ser Pro Gly Ser
        130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
                180                 185                 190

Pro Asp Leu Lys Asn Val Lys Ser Lys Ile Gly Ser Thr Glu Asn Leu
            195                 200                 205

Lys His Gln Pro Gly Gly Gly Lys Val Gln Ile Ile Asn Lys Lys Leu
        210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
                260                 265                 270

Lys Pro Gly Gly Gly Gln Val Glu Val Lys Ser Glu Lys Leu Asp Phe
            275                 280                 285

Lys Asp Arg Val Gln Ser Lys Ile Gly Ser Leu Asp Asn Ile Thr His
        290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335
```

```
Lys Ser Pro Val Val Ser Gly Asp Thr Ser Pro Arg His Leu Ser Asn
            340                 345                 350

Val Ser Ser Thr Gly Ser Ile Asp Met Val Asp Ser Pro Gln Leu Ala
            355                 360                 365

Thr Leu Ala Asp Glu Val Ser Ala Ser Leu Ala Lys Gln Gly Leu
            370                 375                 380

<210> SEQ ID NO 4
<211> LENGTH: 410
<212> TYPE: PRT
<213> ORGANISM: Homo sapiens

<400> SEQUENCE: 4

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Val Tyr Lys Pro Val Asp Leu Ser Lys Val Thr
        275                 280                 285

Ser Lys Cys Gly Ser Leu Gly Asn Ile His His Lys Pro Gly Gly Gly
    290                 295                 300

Gln Val Glu Val Lys Ser Glu Lys Leu Asp Phe Lys Asp Arg Val Gln
305                 310                 315                 320

Ser Lys Ile Gly Ser Leu Asp Asn Ile Thr His Val Pro Gly Gly Gly
```

```
                    325                 330                 335
Asn Lys Lys Ile Glu Thr His Lys Leu Thr Phe Arg Glu Asn Ala Lys
                340                 345                 350

Ala Lys Thr Asp His Gly Ala Glu Ile Val Tyr Lys Ser Pro Val Val
            355                 360                 365

Ser Gly Asp Thr Ser Pro Arg His Leu Ser Asn Val Ser Ser Thr Gly
        370                 375                 380

Ser Ile Asp Met Val Asp Ser Pro Gln Leu Ala Thr Leu Ala Asp Glu
385                 390                 395                 400

Val Ser Ala Ser Leu Ala Lys Gln Gly Leu
                405                 410

<210> SEQ ID NO 5
<211> LENGTH: 381
<212> TYPE: PRT
<213> ORGANISM: Homo sapiens

<400> SEQUENCE: 5

Met Ala Glu Pro Arg Gln Glu Phe Glu Val Met Glu Asp His Ala Gly
1               5                  10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Val Tyr Lys Pro Val Asp Leu Ser
                245                 250                 255

Lys Val Thr Ser Lys Cys Gly Ser Leu Gly Asn Ile His His Lys Pro
            260                 265                 270

Gly Gly Gly Gln Val Glu Val Lys Ser Glu Lys Leu Asp Phe Lys Asp
        275                 280                 285
```

Arg Val Gln Ser Lys Ile Gly Ser Leu Asp Asn Ile Thr His Val Pro
290                 295                 300

Gly Gly Gly Asn Lys Lys Ile Glu Thr His Lys Leu Thr Phe Arg Glu
305                 310                 315                 320

Asn Ala Lys Ala Lys Thr Asp His Gly Ala Glu Ile Val Tyr Lys Ser
                325                 330                 335

Pro Val Val Ser Gly Asp Thr Ser Pro Arg His Leu Ser Asn Val Ser
                340                 345                 350

Ser Thr Gly Ser Ile Asp Met Val Asp Ser Pro Gln Leu Ala Thr Leu
                355                 360                 365

Ala Asp Glu Val Ser Ala Ser Leu Ala Lys Gln Gly Leu
370                 375                 380

<210> SEQ ID NO 6
<211> LENGTH: 352
<212> TYPE: PRT
<213> ORGANISM: Homo sapiens

<400> SEQUENCE: 6

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Ala Glu Glu Ala
            35                  40                  45

Gly Ile Gly Asp Thr Pro Ser Leu Glu Asp Glu Ala Ala Gly His Val
        50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Val Tyr Lys Pro Val
210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
            260                 265                 270

His Val Pro Gly Gly Gly Asn Lys Lys Ile Glu Thr His Lys Leu Thr
        275                 280                 285

```
Phe Arg Glu Asn Ala Lys Ala Lys Thr Asp His Gly Ala Glu Ile Val
        290                 295                 300

Tyr Lys Ser Pro Val Val Ser Gly Asp Thr Ser Pro Arg His Leu Ser
305                 310                 315                 320

Asn Val Ser Ser Thr Gly Ser Ile Asp Met Val Asp Ser Pro Gln Leu
                325                 330                 335

Ala Thr Leu Ala Asp Glu Val Ser Ala Ser Leu Ala Lys Gln Gly Leu
            340                 345                 350

<210> SEQ ID NO 7
<211> LENGTH: 118
<212> TYPE: PRT
<213> ORGANISM: Artificial Sequence
<220> FEATURE:
<223> OTHER INFORMATION: Synthesized

<400> SEQUENCE: 7

Gln Val Gln Leu Gln Gln Pro Gly Ser Val Leu Val Arg Pro Gly Ala
1               5                   10                  15

Ser Val Lys Leu Ser Cys Lys Ala Ser Gly Tyr Thr Phe Thr Ser Ser
            20                  25                  30

Trp Ile His Trp Ala Lys Gln Arg Pro Gly Gln Gly Leu Glu Trp Ile
        35                  40                  45

Gly Glu Ile Tyr Pro Asn Ser Gly Asn Thr Asn Tyr Asn Glu Lys Phe
    50                  55                  60

Lys Gly Lys Ala Thr Leu Thr Val Asp Ile Ser Ser Ser Thr Ala Tyr
65                  70                  75                  80

Val Asp Leu Thr Ser Leu Thr Ser Glu Asp Ser Ala Val Tyr Tyr Cys
                85                  90                  95

Ala Arg Leu Gly Trp Leu Ile Pro Leu Asp Tyr Trp Gly Gln Gly Thr
            100                 105                 110

Thr Leu Ile Val Ser Ser
        115

<210> SEQ ID NO 8
<211> LENGTH: 10
<212> TYPE: PRT
<213> ORGANISM: Artificial Sequence
<220> FEATURE:
<223> OTHER INFORMATION: Synthesized

<400> SEQUENCE: 8

Gly Tyr Thr Phe Thr Ser Ser Trp Ile His
1               5                   10

<210> SEQ ID NO 9
<211> LENGTH: 17
<212> TYPE: PRT
<213> ORGANISM: Artificial Sequence
<220> FEATURE:
<223> OTHER INFORMATION: Synthesized

<400> SEQUENCE: 9

Glu Ile Tyr Pro Asn Ser Gly Asn Thr Asn Tyr Asn Glu Lys Phe Lys
1               5                   10                  15

Gly

<210> SEQ ID NO 10
<211> LENGTH: 9
<212> TYPE: PRT
```

<213> ORGANISM: Artificial Sequence
<220> FEATURE:
<223> OTHER INFORMATION: Synthesized

<400> SEQUENCE: 10

Leu Gly Trp Leu Ile Pro Leu Asp Tyr
1               5

<210> SEQ ID NO 11
<211> LENGTH: 114
<212> TYPE: PRT
<213> ORGANISM: Artificial Sequence
<220> FEATURE:
<223> OTHER INFORMATION: Synthesized

<400> SEQUENCE: 11

Asp Ile Val Leu Ser Gln Ser Pro Ser Ser Leu Ala Val Ser Val Gly
1               5                   10                  15

Glu Lys Val Thr Met Ser Cys Lys Ser Ser Gln Ser Leu Leu Asp Gly
                20                  25                  30

Asn Asp Gln Lys Asn Tyr Leu Ala Trp Tyr Gln Gln Lys Pro Gly Gln
            35                  40                  45

Ser Pro Lys Leu Leu Met Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Leu Lys Ala Glu Asp Leu Ala Val Tyr Tyr Cys Gln Gln
                85                  90                  95

Phe Tyr Asp Tyr Pro Trp Thr Phe Gly Gly Gly Thr Lys Leu Glu Ile
            100                 105                 110

Lys Arg

<210> SEQ ID NO 12
<211> LENGTH: 17
<212> TYPE: PRT
<213> ORGANISM: Artificial Sequence
<220> FEATURE:
<223> OTHER INFORMATION: Synthesized

<400> SEQUENCE: 12

Lys Ser Ser Gln Ser Leu Leu Asp Gly Asn Asp Gln Lys Asn Tyr Leu
1               5                   10                  15

Ala

<210> SEQ ID NO 13
<211> LENGTH: 7
<212> TYPE: PRT
<213> ORGANISM: Artificial Sequence
<220> FEATURE:
<223> OTHER INFORMATION: Synthesized

<400> SEQUENCE: 13

Trp Ala Ser Thr Arg Glu Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Synthesized

<400> SEQUENCE: 14

```
Gln Gln Phe Tyr Asp Tyr Pro Trp Thr
  1               5

<210> SEQ ID NO 15
<211> LENGTH: 118
<212> TYPE: PRT
<213> ORGANISM: Artificial Sequence
<220> FEATURE:
<223> OTHER INFORMATION: Synthesized

<400> SEQUENCE: 15

Glu Val Gln Leu Gln Gln Pro Gly Ser Val Leu Val Arg Pro Gly Ala
  1               5                  10                  15

Ser Val Lys Leu Ser Cys Lys Ala Ser Gly Tyr Thr Phe Thr Ser Ser
                 20                  25                  30

Trp Ile His Trp Ala Lys Gln Arg Pro Gly Gln Gly Leu Glu Trp Ile
             35                  40                  45

Gly Glu Ile Tyr Pro Asn Ser Gly Asn Thr Asn Tyr Asn Glu Lys Phe
         50                  55                  60

Lys Gly Lys Ala Thr Leu Thr Val Asp Ile Ser Ser Thr Ala Tyr
 65                  70                  75                  80

Val Glu Leu Thr Ser Leu Thr Ser Glu Asp Thr Ala Val Tyr Tyr Cys
                 85                  90                  95

Ala Arg Leu Gly Trp Leu Ile Pro Leu Asp Tyr Trp Gly Gln Gly Thr
            100                 105                 110

Thr Val Thr Val Ser Ser
            115

<210> SEQ ID NO 16
<211> LENGTH: 118
<212> TYPE: PRT
<213> ORGANISM: Artificial Sequence
<220> FEATURE:
<223> OTHER INFORMATION: Synthesized

<400> SEQUENCE: 16

Glu Val Gln Leu Gln Gln Ser Gly Ala Glu Leu Val Lys Pro Gly Ala
  1               5                  10                  15

Ser Val Lys Leu Ser Cys Lys Ala Ser Gly Tyr Thr Phe Thr Ser Ser
                 20                  25                  30

Trp Ile His Trp Val Arg Gln Ala Pro Gly Gln Gly Leu Glu Trp Ile
             35                  40                  45

Gly Glu Ile Tyr Pro Asn Ser Gly Asn Thr Asn Tyr Asn Glu Lys Phe
         50                  55                  60

Lys Gly Arg Val Thr Leu Thr Val Asp Thr Ser Ala Ser Thr Ala Tyr
 65                  70                  75                  80

Met Glu Leu Thr Ser Leu Thr Ser Glu Asp Thr Ala Val Tyr Tyr Cys
                 85                  90                  95

Ala Arg Leu Gly Trp Leu Ile Pro Leu Asp Tyr Trp Gly Gln Gly Thr
            100                 105                 110

Thr Val Thr Val Ser Ser
            115

<210> SEQ ID NO 17
<211> LENGTH: 118
<212> TYPE: PRT
<213> ORGANISM: Artificial Sequence
<220> FEATURE:
<223> OTHER INFORMATION: Synthesized
```

<400> SEQUENCE: 17

Glu Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Ser
            20                  25                  30

Trp Ile His Trp Val Arg Gln Arg Pro Gly Gln Gly Leu Glu Trp Ile
        35                  40                  45

Gly Glu Ile Tyr Pro Asn Ser Gly Asn Thr Asn Tyr Asn Glu Lys Phe
    50                  55                  60

Lys Gly Lys Ala Thr Leu Thr Val Asp Ile Ser Ile Ser Thr Ala Tyr
65                  70                  75                  80

Met Glu Leu Ser Arg Leu Thr Ser Asp Asp Thr Ala Val Tyr Tyr Cys
                85                  90                  95

Ala Arg Leu Gly Trp Leu Ile Pro Leu Asp Tyr Trp Gly Gln Gly Thr
            100                 105                 110

Thr Val Thr Val Ser Ser
        115

<210> SEQ ID NO 18
<211> LENGTH: 118
<212> TYPE: PRT
<213> ORGANISM: Artificial Sequence
<220> FEATURE:
<223> OTHER INFORMATION: Synthesized

<400> SEQUENCE: 18

Glu Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Gly Ser
            20                  25                  30

Trp Ile His Trp Val Arg Gln Arg Pro Gly Gln Gly Leu Glu Trp Ile
        35                  40                  45

Gly Glu Ile Tyr Pro Asn Ser Gly Asn Thr Asn Tyr Ala Glu Lys Phe
    50                  55                  60

Lys Gly Lys Ala Thr Leu Thr Val Asp Ile Ser Ile Ser Thr Ala Tyr
65                  70                  75                  80

Met Glu Leu Ser Arg Leu Thr Ser Asp Asp Thr Ala Val Tyr Tyr Cys
                85                  90                  95

Ala Arg Leu Gly Trp Leu Ile Pro Leu Asp Tyr Trp Gly Gln Gly Thr
            100                 105                 110

Thr Val Thr Val Ser Ser
        115

<210> SEQ ID NO 19
<211> LENGTH: 118
<212> TYPE: PRT
<213> ORGANISM: Artificial Sequence
<220> FEATURE:
<223> OTHER INFORMATION: Synthesized

<400> SEQUENCE: 19

Glu Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Ser
            20                  25                  30

Trp Ile His Trp Val Arg Gln Arg Pro Gly Gln Gly Leu Glu Trp Ile
        35                  40                  45

```
Gly Glu Ile Tyr Pro Asn Ser Gly Asn Thr Asn Tyr Asn Glu Lys Phe
         50                  55                  60

Lys Gly Arg Val Thr Leu Thr Arg Asp Ile Ser Ile Ser Thr Ala Tyr
 65                  70                  75                  80

Met Glu Leu Ser Arg Leu Thr Ser Asp Asp Thr Ala Val Tyr Tyr Cys
                 85                  90                  95

Ala Arg Leu Gly Trp Leu Ile Pro Leu Asp Tyr Trp Gly Gln Gly Thr
                100                 105                 110

Thr Val Thr Val Ser Ser
            115
```

<210> SEQ ID NO 20
<211> LENGTH: 118
<212> TYPE: PRT
<213> ORGANISM: Artificial Sequence
<220> FEATURE:
<223> OTHER INFORMATION: Synthesized

<400> SEQUENCE: 20

```
Glu Val Gln Leu Val Gln Ser Gly Ala Glu Val Val Lys Pro Gly Ala
 1               5                  10                  15

Ser Val Lys Val Ser Cys Lys Ala Ser Gly Tyr Thr Phe Thr Gly Ser
                 20                  25                  30

Trp Ile His Trp Val Arg Gln Arg Pro Gly Gln Gly Leu Glu Trp Ile
             35                  40                  45

Gly Glu Ile Tyr Pro Asn Ser Gly Asn Thr Asn Tyr Ala Glu Lys Phe
         50                  55                  60

Gln Gly Arg Val Thr Leu Thr Arg Asp Ile Ser Ile Ser Thr Ala Tyr
 65                  70                  75                  80

Met Glu Leu Ser Arg Leu Thr Ser Asp Asp Thr Ala Val Tyr Tyr Cys
                 85                  90                  95

Ala Arg Leu Gly Trp Leu Ile Pro Leu Asp Tyr Trp Gly Gln Gly Thr
                100                 105                 110

Thr Val Thr Val Ser Ser
            115
```

<210> SEQ ID NO 21
<211> LENGTH: 118
<212> TYPE: PRT
<213> ORGANISM: Artificial Sequence
<220> FEATURE:
<223> OTHER INFORMATION: Synthesized

<400> SEQUENCE: 21

```
Glu Val Gln Leu Gln Gln Pro Gly Ser Val Leu Val Arg Pro Gly Ala
 1               5                  10                  15

Ser Val Lys Leu Ser Cys Lys Ala Ser Gly Tyr Thr Phe Thr Ser Ser
                 20                  25                  30

Trp Ile His Trp Val Arg Gln Ala Pro Gly Gln Gly Leu Glu Trp Ile
             35                  40                  45

Gly Glu Ile Tyr Pro Asn Ser Gly Asn Thr Asn Tyr Asn Glu Lys Phe
         50                  55                  60

Lys Gly Arg Val Thr Leu Thr Val Asp Thr Ser Ala Ser Thr Ala Tyr
 65                  70                  75                  80

Met Glu Leu Thr Ser Leu Thr Ser Glu Asp Thr Ala Val Tyr Tyr Cys
                 85                  90                  95

Ala Arg Leu Gly Trp Leu Ile Pro Leu Asp Tyr Trp Gly Gln Gly Thr
```

Thr Val Thr Val Ser Ser
              115

<210> SEQ ID NO 22
<211> LENGTH: 118
<212> TYPE: PRT
<213> ORGANISM: Artificial Sequence
<220> FEATURE:
<223> OTHER INFORMATION: Synthesized

<400> SEQUENCE: 22

Glu Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Ser
            20                  25                  30

Trp Ile His Trp Val Arg Gln Ala Pro Gly Gln Gly Leu Glu Trp Ile
        35                  40                  45

Gly Glu Ile Tyr Pro Asn Ser Gly Asn Thr Asn Tyr Asn Glu Lys Phe
    50                  55                  60

Lys Gly Lys Ala Thr Leu Thr Val Asp Ile Ser Ser Ser Thr Ala Tyr
65                  70                  75                  80

Met Glu Leu Thr Ser Leu Thr Ser Glu Asp Thr Ala Val Tyr Tyr Cys
                85                  90                  95

Ala Arg Leu Gly Trp Leu Ile Pro Leu Asp Tyr Trp Gly Gln Gly Thr
            100                 105                 110

Thr Val Thr Val Ser Ser
              115

<210> SEQ ID NO 23
<211> LENGTH: 118
<212> TYPE: PRT
<213> ORGANISM: Artificial Sequence
<220> FEATURE:
<223> OTHER INFORMATION: Synthesized

<400> SEQUENCE: 23

Glu Val Gln Leu Gln Gln Pro Gly Ser Val Leu Val Arg Pro Gly Ala
1               5                   10                  15

Ser Val Lys Leu Ser Cys Lys Ala Ser Gly Tyr Thr Phe Thr Ser Ser
            20                  25                  30

Trp Ile His Trp Val Lys Gln Arg Pro Gly Gln Gly Leu Glu Trp Ile
        35                  40                  45

Gly Glu Ile Tyr Pro Asn Ser Gly Asn Thr Asn Tyr Asn Glu Lys Phe
    50                  55                  60

Lys Gly Lys Ala Thr Leu Thr Val Asp Ile Ser Ser Ser Thr Ala Tyr
65                  70                  75                  80

Val Glu Leu Thr Ser Leu Thr Ser Glu Asp Thr Ala Val Tyr Tyr Cys
                85                  90                  95

Ala Arg Leu Gly Trp Leu Ile Pro Leu Asp Tyr Trp Gly Gln Gly Thr
            100                 105                 110

Thr Val Thr Val Ser Ser
              115

<210> SEQ ID NO 24
<211> LENGTH: 118
<212> TYPE: PRT
<213> ORGANISM: Artificial Sequence
<220> FEATURE:

-continued

<223> OTHER INFORMATION: Synthesized

<400> SEQUENCE: 24

Glu Val Gln Leu Gln Gln Pro Gly Ser Val Leu Val Arg Pro Gly Ala
1               5                   10                  15

Ser Val Lys Leu Ser Cys Lys Ala Ser Gly Tyr Thr Phe Thr Ser Ser
            20                  25                  30

Trp Ile His Trp Val Arg Gln Arg Pro Gly Gln Gly Leu Glu Trp Ile
        35                  40                  45

Gly Glu Ile Tyr Pro Asn Ser Gly Asn Thr Asn Tyr Asn Glu Lys Phe
    50                  55                  60

Lys Gly Lys Ala Thr Leu Thr Val Asp Ile Ser Ser Thr Ala Tyr
65                  70                  75                  80

Val Glu Leu Thr Ser Leu Thr Ser Glu Asp Thr Ala Val Tyr Tyr Cys
                85                  90                  95

Ala Arg Leu Gly Trp Leu Ile Pro Leu Asp Tyr Trp Gly Gln Gly Thr
            100                 105                 110

Thr Val Thr Val Ser Ser
            115

<210> SEQ ID NO 25
<211> LENGTH: 118
<212> TYPE: PRT
<213> ORGANISM: Artificial Sequence
<220> FEATURE:
<223> OTHER INFORMATION: Synthesized

<400> SEQUENCE: 25

Gln Val Gln Leu Val Gln Pro Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Trp Ile His Trp Val Arg Gln Ala Pro Gly Gln Gly Leu Glu Trp Met
        35                  40                  45

Gly Glu Ile Tyr Pro Asn Ser Gly Asn Thr Asn Tyr Asn Glu Lys Phe
    50                  55                  60

Lys Gly Arg Val Thr Met Thr Val Asp Ile Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Leu Gly Trp Leu Ile Pro Leu Asp Tyr Trp Gly Gln Gly Thr
            100                 105                 110

Thr Val Thr Val Ser Ser
            115

<210> SEQ ID NO 26
<211> LENGTH: 118
<212> TYPE: PRT
<213> ORGANISM: Artificial Sequence
<220> FEATURE:
<223> OTHER INFORMATION: Synthesized

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Trp Ile His Trp Val Arg Gln Ala Pro Gly Gln Gly Leu Glu Trp Met

```
                        35                  40                  45

Gly Glu Ile Tyr Pro Asn Ser Gly Asn Thr Asn Tyr Asn Glu Lys Phe
 50                  55                  60

Lys Gly Arg Val Thr Met Thr Val Asp Thr Ser Ile Ser Thr Ala Tyr
 65                  70                  75                  80

Met Glu Leu Ser Arg Leu Arg Ser Asp Thr Ala Val Tyr Tyr Cys
                 85                  90                  95

Ala Arg Leu Gly Trp Leu Ile Pro Leu Asp Tyr Trp Gly Gln Gly Thr
                100                 105                 110

Thr Val Thr Val Ser Ser
        115

<210> SEQ ID NO 27
<211> LENGTH: 118
<212> TYPE: PRT
<213> ORGANISM: Artificial Sequence
<220> FEATURE:
<223> OTHER INFORMATION: Synthesized

<400> SEQUENCE: 27

Glu Val Gln Leu Val Gln Pro Gly Ala Glu Val Lys Lys Pro Gly Ala
 1               5                  10                  15

Ser Val Lys Val Ser Cys Lys Ala Ser Gly Tyr Thr Phe Thr Ser Ser
                20                  25                  30

Trp Ile His Trp Val Arg Gln Ala Pro Gly Gln Gly Leu Glu Trp Met
             35                  40                  45

Gly Glu Ile Tyr Pro Asn Ser Gly Asn Thr Asn Tyr Asn Glu Lys Phe
 50                  55                  60

Lys Gly Arg Val Thr Met Thr Val Asp Ile Ser Ile Ser Thr Ala Tyr
 65                  70                  75                  80

Met Glu Leu Ser Arg Leu Arg Ser Asp Thr Ala Val Tyr Tyr Cys
                 85                  90                  95

Ala Arg Leu Gly Trp Leu Ile Pro Leu Asp Tyr Trp Gly Gln Gly Thr
                100                 105                 110

Thr Val Thr Val Ser Ser
        115

<210> SEQ ID NO 28
<211> LENGTH: 114
<212> TYPE: PRT
<213> ORGANISM: Artificial Sequence
<220> FEATURE:
<223> OTHER INFORMATION: Synthesized

<400> SEQUENCE: 28

Asp Ile Val Leu Thr Gln Ser Pro Ser Ser Leu Ala Val Ser Val Gly
 1               5                  10                  15

Glu Lys Val Thr Met Ser Cys Lys Ser Ser Gln Ser Leu Leu Asp Gly
                20                  25                  30

Asn Asp Gln Lys Asn Tyr Leu Ala Trp Tyr Gln Gln Lys Pro Gly Gln
             35                  40                  45

Ser Pro Lys Leu Leu Met Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95
```

```
Phe Tyr Asp Tyr Pro Trp Thr Phe Gly Gly Gly Thr Lys Leu Glu Ile
                100                 105                 110

Lys Arg
```

<210> SEQ ID NO 29
<211> LENGTH: 114
<212> TYPE: PRT
<213> ORGANISM: Artificial Sequence
<220> FEATURE:
<223> OTHER INFORMATION: Synthesized

<400> SEQUENCE: 29

```
Asp Ile Val Leu Thr Gln Ser Pro Ser Ser Leu Ala Val Ser Val Gly
1               5                   10                  15

Glu Arg Ala Thr Ile Ser Cys Lys Ser Gln Ser Leu Leu Asp Gly
                20                  25                  30

Asn Asp Gln Lys Asn Tyr Leu Ala Trp Tyr Gln Gln Lys Pro Gly Gln
                35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Tyr Asp Tyr Pro Trp Thr Phe Gly Gly Gly Thr Lys Leu Glu Ile
                100                 105                 110

Lys Arg
```

<210> SEQ ID NO 30
<211> LENGTH: 114
<212> TYPE: PRT
<213> ORGANISM: Artificial Sequence
<220> FEATURE:
<223> OTHER INFORMATION: Synthesized

<400> SEQUENCE: 30

```
Asp Ile Val Leu Thr Gln Ser Pro Ser Ser Leu Ala Val Ser Val Gly
1               5                   10                  15

Glu Lys Val Thr Met Ser Cys Lys Ser Gln Ser Leu Leu Asp Gly
                20                  25                  30

Asn Asp Gln Lys Asn Tyr Leu Ala Trp Tyr Gln Gln Lys Pro Gly Gln
                35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Tyr Asp Tyr Pro Trp Thr Phe Gly Gly Gly Thr Lys Leu Glu Ile
                100                 105                 110

Lys Arg
```

<210> SEQ ID NO 31
<211> LENGTH: 118
<212> TYPE: PRT
<213> ORGANISM: Homo sapiens

<400> SEQUENCE: 31

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Arg Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Met Thr Arg Asp Thr Ser Ile Arg Thr Ala Tyr
65                  70                  75                  80

Val Glu Leu Ser Arg Leu Thr Ser Asp Asp Thr Ala Val Tyr Tyr Cys
                85                  90                  95

Ala Ser Leu Ala Asp Asp Pro Glu Asp Phe Trp Gly Gln Gly Thr
            100                 105                 110

Leu Val Thr Val Ser Ser
        115

<210> SEQ ID NO 32
<211> LENGTH: 120
<212> TYPE: PRT
<213> ORGANISM: Homo sapiens

<400> SEQUENCE: 32

Gln Val Gln Leu Val Glu Ser Gly Ala Glu Val Lys Lys Pro Gly Ala
1               5                   10                  15

Ser Val Lys Leu Ser Cys Lys Ala Ser Gly Tyr Thr Phe Ser Ser Tyr
            20                  25                  30

Trp Met His Trp Val Arg Gln Ala Pro Gly Gln Arg Leu Glu Trp Met
        35                  40                  45

Gly Glu Ile Asn Pro Asp Asn Gly His Thr Asn Tyr Asn Glu Lys Phe
    50                  55                  60

Lys Ser Arg Val Thr Ile Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Asp Tyr Ser Tyr Gly Ala Phe Asp Ile Trp Gly Pro
            100                 105                 110

Gly Thr Thr Val Thr Val Ser Ser
        115                 120

<210> SEQ ID NO 33
<211> LENGTH: 96
<212> TYPE: PRT
<213> ORGANISM: Homo sapiens

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80
```

```
Met Glu Leu Ser Arg Leu Arg Ser Asp Asp Thr Ala Val Tyr Tyr Cys
            85                  90                  95
```

<210> SEQ ID NO 34
<211> LENGTH: 114
<212> TYPE: PRT
<213> ORGANISM: Homo sapiens

<400> SEQUENCE: 34

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Pro Met Phe Gly Gln Gly Thr Lys Val Glu Ile
            100                 105                 110

Lys Arg
```

<210> SEQ ID NO 35
<211> LENGTH: 114
<212> TYPE: PRT
<213> ORGANISM: Homo sapiens

<400> SEQUENCE: 35

```
Asp Ile Val Leu Thr Gln Ser Pro Asp Ser Leu Ala Val Ser Leu Gly
1               5                   10                  15

Glu Arg Ala Thr Ile Lys Cys Lys Ser Ser Gln Ser Val Leu Tyr Gly
            20                  25                  30

Ser Asp Ser Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Glu Phe Thr Leu Thr
65                  70                  75                  80

Ile Ser Ser Leu Gln Ala Ala Asp Val Ala Val Tyr Tyr Cys Gln Glu
                85                  90                  95

Tyr Tyr Ser Ser Leu Cys Thr Phe Gly Gln Gly Thr Lys Leu Glu Ile
            100                 105                 110

Lys Arg
```

<210> SEQ ID NO 36
<211> LENGTH: 101
<212> TYPE: PRT
<213> ORGANISM: Homo sapiens

<400> SEQUENCE: 36

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30
```

```
Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Thr Pro
            100

<210> SEQ ID NO 37
<211> LENGTH: 354
<212> TYPE: DNA
<213> ORGANISM: Artificial Sequence
<220> FEATURE:
<223> OTHER INFORMATION: Synthesized

<400> SEQUENCE: 37
caggtccaac tgcagcagcc tgggtctgtg ctggtgaggc ctggagcttc agtgaagctg      60
tcctgcaagg cttctggcta caccttcacc agctcctgga tacactgggc gaagcagagg     120
cctggacaag gccttgagtg gattggagag atttatccta atagtggtaa tactaactac     180
aatgagaagt tcaagggcaa ggccacactg actgtagaca tatcctccag cacagcctac     240
gtggatctca ccagcctgac atctgaggac tctgcggtct attattgtgc aagattggga     300
tggttaatac cccttgacta ctggggccaa ggcaccactc tcatagtctc ctca           354

<210> SEQ ID NO 38
<211> LENGTH: 342
<212> TYPE: DNA
<213> ORGANISM: Artificial Sequence
<220> FEATURE:
<223> OTHER INFORMATION: Synthesized

<400> SEQUENCE: 38
gacattgtgc tgtcacagtc tccatcctcc ctagctgtgt cagttggaga gaaggttact      60
atgagctgca gtccagtca gagccttta gatggtaatg atcaaaagaa ctacttggcc       120
tggtaccagc agaaaccagg gcagtctcct aaactgctga tgtactgggc atccactagg     180
gaatctgggg tccctgatcg cttcacaggc agtggatctg ggacagattt cactctcacc     240
atcagcagtt tgaaggctga agacctggca gtttattact gtcagcagtt ttatgactat     300
ccgtggacgt tcggtggagg caccaagctg gaaatcaaac gt                        342

<210> SEQ ID NO 39
<211> LENGTH: 5
<212> TYPE: PRT
<213> ORGANISM: Artificial Sequence
<220> FEATURE:
<223> OTHER INFORMATION: Synthesized

<400> SEQUENCE: 39

Ser Ser Trp Ile His
1               5

<210> SEQ ID NO 40
<211> LENGTH: 7
<212> TYPE: PRT
<213> ORGANISM: Artificial Sequence
<220> FEATURE:
<223> OTHER INFORMATION: Synthesized
```

```
<400> SEQUENCE: 40

Gly Tyr Thr Phe Thr Ser Ser
1               5

<210> SEQ ID NO 41
<211> LENGTH: 6
<212> TYPE: PRT
<213> ORGANISM: Artificial Sequence
<220> FEATURE:
<223> OTHER INFORMATION: Synthesized

<400> SEQUENCE: 41

Tyr Pro Asn Ser Gly Asn
1               5

<210> SEQ ID NO 42
<211> LENGTH: 10
<212> TYPE: PRT
<213> ORGANISM: Artificial Sequence
<220> FEATURE:
<223> OTHER INFORMATION: Synthesized

<400> SEQUENCE: 42

Glu Ile Tyr Pro Asn Ser Gly Asn Thr Asn
1               5                   10

<210> SEQ ID NO 43
<211> LENGTH: 7
<212> TYPE: PRT
<213> ORGANISM: Artificial Sequence
<220> FEATURE:
<223> OTHER INFORMATION: Synthesized

<400> SEQUENCE: 43

Lys Asn Tyr Leu Ala Trp Tyr
1               5

<210> SEQ ID NO 44
<211> LENGTH: 10
<212> TYPE: PRT
<213> ORGANISM: Artificial Sequence
<220> FEATURE:
<223> OTHER INFORMATION: Synthesized

<400> SEQUENCE: 44

Leu Leu Met Tyr Trp Ala Ser Thr Arg Glu
1               5                   10

<210> SEQ ID NO 45
<211> LENGTH: 8
<212> TYPE: PRT
<213> ORGANISM: Artificial Sequence
<220> FEATURE:
<223> OTHER INFORMATION: Synthesized

<400> SEQUENCE: 45

Gln Gln Phe Tyr Asp Tyr Pro Trp
1               5

<210> SEQ ID NO 46
<211> LENGTH: 6
<212> TYPE: PRT
<213> ORGANISM: Artificial Sequence
<220> FEATURE:
<223> OTHER INFORMATION: Synthesized
```

```
<400> SEQUENCE: 46

Thr Ser Ser Trp Ile His
1               5

<210> SEQ ID NO 47
<211> LENGTH: 13
<212> TYPE: PRT
<213> ORGANISM: Artificial Sequence
<220> FEATURE:
<223> OTHER INFORMATION: Synthesized

<400> SEQUENCE: 47

Trp Ile Gly Glu Ile Tyr Pro Asn Ser Gly Asn Thr Asn
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Synthesized

<400> SEQUENCE: 48

Ala Arg Leu Gly Trp Leu Ile Pro Leu Asp
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Synthesized

<400> SEQUENCE: 49

Gly Tyr Thr Phe Thr Gly Ser Trp Ile His
1               5                   10

<210> SEQ ID NO 50
<211> LENGTH: 17
<212> TYPE: PRT
<213> ORGANISM: Artificial Sequence
<220> FEATURE:
<223> OTHER INFORMATION: Synthesized

<400> SEQUENCE: 50

Glu Ile Tyr Pro Asn Ser Gly Asn Thr Asn Tyr Ala Glu Lys Phe Lys
1               5                   10                  15

Gly

<210> SEQ ID NO 51
<211> LENGTH: 17
<212> TYPE: PRT
<213> ORGANISM: Artificial Sequence
<220> FEATURE:
<223> OTHER INFORMATION: Synthesized

<400> SEQUENCE: 51

Glu Ile Tyr Pro Asn Ser Gly Asn Thr Asn Tyr Ala Glu Lys Phe Gln
1               5                   10                  15

Gly

<210> SEQ ID NO 52
<211> LENGTH: 118
<212> TYPE: PRT
<213> ORGANISM: Artificial Sequence
```

```
<220> FEATURE:
<223> OTHER INFORMATION: Synthesized
<220> FEATURE:
<221> NAME/KEY: MISC_FEATURE
<222> LOCATION: (5)..(5)
<223> OTHER INFORMATION: Xaa =  Gln or Val
<220> FEATURE:
<221> NAME/KEY: MISC_FEATURE
<222> LOCATION: (7)..(7)
<223> OTHER INFORMATION: Xaa =  Pro or Ser
<220> FEATURE:
<221> NAME/KEY: MISC_FEATURE
<222> LOCATION: (11)..(11)
<223> OTHER INFORMATION: Xaa =  Leu or Val
<220> FEATURE:
<221> NAME/KEY: MISC_FEATURE
<222> LOCATION: (20)..(20)
<223> OTHER INFORMATION: Xaa =  Leu or Val
<220> FEATURE:
<221> NAME/KEY: MISC_FEATURE
<222> LOCATION: (67)..(67)
<223> OTHER INFORMATION: Xaa =  Lys or Arg
<220> FEATURE:
<221> NAME/KEY: MISC_FEATURE
<222> LOCATION: (68)..(68)
<223> OTHER INFORMATION: Xaa =  Ala or Val
<220> FEATURE:
<221> NAME/KEY: MISC_FEATURE
<222> LOCATION: (84)..(84)
<223> OTHER INFORMATION: Xaa =  Thr or Ser
<220> FEATURE:
<221> NAME/KEY: MISC_FEATURE
<222> LOCATION: (85)..(85)
<223> OTHER INFORMATION: Xaa =  Ser or Arg
<220> FEATURE:
<221> NAME/KEY: MISC_FEATURE
<222> LOCATION: (89)..(89)
<223> OTHER INFORMATION: Xaa =  Glu  or Asp

<400> SEQUENCE: 52

Glu Val Gln Leu Xaa Gln Xaa Gly Ala Glu Xaa Val Lys Pro Gly Ala
1               5                  10                  15

Ser Val Lys Xaa Ser Cys Lys Ala Ser Gly Tyr Thr Phe Thr Ser Ser
            20                  25                  30

Trp Ile His Trp Val Arg Gln Arg Pro Gly Gln Gly Leu Glu Trp Ile
        35                  40                  45

Gly Glu Ile Tyr Pro Asn Ser Gly Asn Thr Asn Tyr Asn Glu Lys Phe
    50                  55                  60

Lys Gly Xaa Xaa Thr Leu Thr Val Asp Ile Ser Ile Ser Thr Ala Tyr
65                  70                  75                  80

Met Glu Leu Xaa Xaa Leu Thr Ser Xaa Asp Thr Ala Val Tyr Tyr Cys
                85                  90                  95

Ala Arg Leu Gly Trp Leu Ile Pro Leu Asp Tyr Trp Gly Gln Gly Thr
            100                 105                 110

Thr Val Thr Val Ser Ser
        115

<210> SEQ ID NO 53
<211> LENGTH: 114
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (54)..(54)
<223> OTHER INFORMATION: Xaa = Met or Ile

<400> SEQUENCE: 53
```

```
Asp Ile Val Leu Thr Gln Ser Pro Ser Ser Leu Ala Val Ser Val Gly
1               5                   10                  15

Glu Lys Val Thr Met Ser Cys Lys Ser Ser Gln Ser Leu Leu Asp Gly
                20                  25                  30

Asn Asp Gln Lys Asn Tyr Leu Ala Trp Tyr Gln Gln Lys Pro Gly Gln
            35                  40                  45

Ser Pro Lys Leu Leu Xaa Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Tyr Asp Tyr Pro Trp Thr Phe Gly Gly Gly Thr Lys Leu Glu Ile
            100                 105                 110

Lys Arg
```

<210> SEQ ID NO 54
<211> LENGTH: 448
<212> TYPE: PRT
<213> ORGANISM: Artificial Sequence
<220> FEATURE:
<223> OTHER INFORMATION: Synthesized

<400> SEQUENCE: 54

```
Gln Val Gln Leu Gln Gln Pro Gly Ser Val Leu Val Arg Pro Gly Ala
1               5                   10                  15

Ser Val Lys Leu Ser Cys Lys Ala Ser Gly Tyr Thr Phe Thr Ser Ser
                20                  25                  30

Trp Ile His Trp Ala Lys Gln Arg Pro Gly Gln Gly Leu Glu Trp Ile
            35                  40                  45

Gly Glu Ile Tyr Pro Asn Ser Gly Asn Thr Asn Tyr Asn Glu Lys Phe
    50                  55                  60

Lys Gly Lys Ala Thr Leu Thr Val Asp Ile Ser Ser Thr Ala Tyr
65                  70                  75                  80

Val Asp Leu Thr Ser Leu Thr Ser Glu Asp Ser Ala Val Tyr Tyr Cys
                85                  90                  95

Ala Arg Leu Gly Trp Leu Ile Pro Leu Asp Tyr Trp Gly Gln Gly Thr
            100                 105                 110

Thr Leu Ile Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
```

```
                     245                 250                 255
Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 55
<211> LENGTH: 221
<212> TYPE: PRT
<213> ORGANISM: Artificial Sequence
<220> FEATURE:
<223> OTHER INFORMATION: Synthesized

<400> SEQUENCE: 55

Asp Ile Val Leu Ser Gln Ser Pro Ser Ser Leu Ala Val Ser Val Gly
1               5                   10                  15

Glu Lys Val Thr Met Ser Cys Lys Ser Ser Gln Ser Leu Leu Asp Gly
            20                  25                  30

Asn Asp Gln Lys Asn Tyr Leu Ala Trp Tyr Gln Gln Lys Pro Gly Gln
        35                  40                  45

Ser Pro Lys Leu Leu Met Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Leu Lys Ala Glu Asp Leu Ala Val Tyr Tyr Cys Gln Gln
                85                  90                  95

Phe Tyr Asp Tyr Pro Trp Thr Phe Gly Gly Gly Thr Lys Leu Glu Ile
            100                 105                 110

Lys Arg Lys Thr Val Ala Ala Pro Ser Val Phe Ile Phe Pro Pro Ser
        115                 120                 125

Asp Glu Gln Leu Lys Ser Gly Thr Ala Ser Val Val Cys Leu Leu Asn
    130                 135                 140

Asn Phe Tyr Pro Arg Glu Ala Lys Val Gln Trp Lys Val Asp Asn Ala
145                 150                 155                 160

Leu Gln Ser Gly Asn Ser Gln Glu Ser Val Thr Glu Gln Asp Ser Lys
```

```
                165                 170                 175
Asp Ser Thr Tyr Ser Leu Ser Ser Thr Leu Thr Leu Ser Lys Ala Asp
                180                 185                 190

Tyr Glu Lys His Lys Val Tyr Ala Cys Glu Val Thr His Gln Gly Leu
            195                 200                 205

Ser Ser Pro Val Thr Lys Ser Phe Asn Arg Gly Glu Cys
    210                 215                 220
```

ANTIBODIES RECOGNIZING TAU

CROSS-REFERENCE TO RELATED APPLICATIONS

This application is a US national stage entry of PCT/IB2017/052545 filed May 2, 2017, which claims the benefit under 35 USC 119(e) of U.S. Provisional Application No. 62/330,800 filed May 2, 2016, which is incorporated by reference in its entirety for all purposes

REFERENCE TO A SEQUENCE LISTING

The Sequence Listing written in file 516720_SEQL-ST.TXT is 60,763 bytes, was created on Oct. 29, 2018, and is hereby incorporated by reference.

BACKGROUND OF THE INVENTION

Tau is a well-known human protein that can exist in phosphorylated forms (see, e.g., Goedert, Proc. Natl. Acad. Sci. U.S.A. 85:4051-4055(1988); Goedert, EMBO J. 8:393-399(1989); Lee, Neuron 2:1615-1624(1989); Goedert, Neuron 3:519-526(1989); Andreadis, Biochemistry 31:10626-10633(1992). Tau has been reported to have a role in stabilizing microtubules, particularly in the central nervous system. Total tau (t-tau, i.e., phosphorylated and unphosphorylated forms) and phospho-tau (p-tau, i.e., phosphorylated tau) are released by the brain in response to neuronal injury and neurodegeneration and have been reported to occur at increased levels in the CSF of Alzheimer's patients relative to the general population (Jack et al., Lancet Neurol 9: 119-28 (2010)).

Tau is the principal constituent of neurofibrillary tangles, which together with plaques are a hallmark characteristic of Alzheimer's disease. The tangles constitute abnormal fibrils measuring 10 nm in diameter occurring in pairs wound in a helical fashion with a regular periodicity of 80 nm. The tau within neurofibrillary tangles is abnormally phosphorylated (hyperphosphorylated) with phosphate groups attached to specific sites on the molecule. Severe involvement of neurofibrillary tangles is seen in the layer II neurons of the entorhinal cortex, the CA1 and subicular regions of the hippocampus, the amygdala, and the deeper layers (layers III, V, and superficial VI) of the neocortex in Alzheimer's disease. Hyperphosphorylated tau has also been reported to interfere with microtubule assembly, which may promote neuronal network breakdown.

Tau inclusions are part of the defining neurophathology of several neurodegenerative diseases including Alzheimer's disease, frontotemporal lobar degeneration, progressive supranuclear palsy and Pick's disease.

BRIEF SUMMARY OF THE CLAIMED INVENTION

In one aspect, the invention provides an isolated monoclonal antibody that specifically binds to tau. Examples of such antibodies bind to an epitope within amino acid residues 55-78, 60-75 or 61-70 of SEQ ID NO:3 (corresponding to amino acid residues 113-136, 118-133, or 119-128, respectively, of SEQ ID NO:1).

Some such antibodies compete for binding to human tau with antibody 16G7. Some such antibodies bind to the same epitope on human tau as 16G7.

Some antibodies comprise three light chain CDRs as and three heavy chain CDRs of monoclonal antibody 16G7, wherein 16G7 is a mouse antibody characterized by a heavy chain variable region having an amino acid sequence comprising SEQ ID NO: 7 and a light chain variable region having an amino acid sequence comprising SEQ ID NO: 11. In some antibodies, the three heavy chain CDRs are as defined by Kabat/Chothia Composite (SEQ ID NOs: 8, 9, and 10) and the three light chain CDRs are as defined by Kabat/Chothia Composite (SEQ ID NOs: 12, 13, and 14).

For example, the antibody can be 16G7 or a chimeric, veneered, or humanized form thereof. In some such antibodies, the variable heavy chain has 85% identity to human sequence. In some such antibodies, the variable light chain has 85% identity to human sequence. In some such antibodies, each of the variable heavy chain and variable light chain has 85% identity to human germline sequence. In some such antibodies, the mature heavy chain variable region comprises the three heavy chain CDRs are as defined by Kabat/Chothia Composite (SEQ ID NOs: 8, 9, and 10) and the three light chain CDRs are as defined by Kabat/Chothia Composite (SEQ ID NOs: 12, 13, and 14); provided that position H31 is occupied by S or G, position H60 is occupied by N or A and position 64 is occupied by K or Q. In some such antibodies, CDR-H1 has an amino acid sequence comprising SEQ ID NO: 49. In some such antibodies, CDR-H2 has an amino acid sequence comprising SEQ ID NO: 50. In some such antibodies, CDR-H2 has an amino acid sequence comprising SEQ ID NO: 51. In some such antibodies, the antibody is a humanized antibody.

In some such antibodies, the CDR-H1 has an amino acid sequence comprising SEQ ID NO: 49 and CDR-H2 has an amino acid sequence comprising SEQ ID NO: 50. In some such antibodies, the CDR-H1 has an amino acid sequence comprising SEQ ID NO: 49 and CDR-H2 has an amino acid sequence comprising SEQ ID NO: 51.

Some antibodies are a humanized or chimeric 16G7 antibody that specifically binds to human tau, wherein 16G7 is a mouse antibody characterized by a mature heavy chain variable region of SEQ ID NO:7 and a mature light chain variable region of SEQ ID NO: 11. Some such antibodies are a humanized antibody comprising a humanized mature heavy chain variable region comprising the three heavy chain CDRs of 16G7 and a humanized mature light chain variable region comprising the three light chain CDRs of 16G7. In some such antibodies, the CDRs are of a definition selected from the group of Kabat, Chothia, Kabat/Chothia Composite, AbM and Contact.

In some such antibodies the humanized mature heavy chain variable region comprises the three Kabat/Chothia Composite heavy chain CDRs of 16G7 (SEQ ID NOs: 8-10) and the humanized mature light chain variable region comprises the three Kabat/Chothia Composite light chain CDRs of 16G7 (SEQ ID NOs: 12-14).

In some such antibodies, the humanized mature heavy chain variable region comprises the three Kabat heavy chain CDRs of 16G7 (SEQ ID NO:39, SEQ ID NO:9, and SEQ ID NO:10) and the humanized mature light chain variable region comprises the three Kabat light chain CDRs of 16G7 (SEQ ID NOs: 12-14).

In some such antibodies, the humanized mature heavy chain variable region comprises the three Chothia heavy chain CDRs of 16G7 (SEQ ID NO:40, SEQ ID NO:41, and SEQ ID NO:10) and the humanized mature light chain variable region comprises the three Chothia light chain CDRs of 16G7 (SEQ ID NOs: 12-14).

In some such antibodies, the humanized mature heavy chain variable region comprises the three AbM heavy chain CDRs of 16G7 (SEQ ID NO:8, SEQ ID NO:42, and SEQ ID NO:10)) and the humanized mature light chain variable region comprises the three AbM light chain CDRs of 16G7 (SEQ ID NOs: 12-14).

In some such antibodies, the humanized mature heavy chain variable region comprises the three Contact heavy chain CDRs of 16G7 (SEQ ID NO:46-48) and the humanized mature light chain variable region comprises the three Contact light chain CDRs of 16G7 (SEQ ID NO:43-45).

In some antibodies, the humanized mature heavy chain variable region has an amino acid sequence at least 90% identical to any one of SEQ ID NO:15-27 and a humanized mature light chain variable region having an amino acid sequence at least 90% identical to any one of SEQ ID NO: 28-30.

In some such antibodies, at least one of the following positions in the VH region is occupied by the amino acid as specified: H1 is occupied by E, H5 is occupied by Q, H7 is occupied by P, H9 is occupied by S, H10 is occupied by V, H11 is occupied L, H12 is occupied by V, H13 is occupied by R, H20 is occupied by L, H40 is occupied by R, H48 is occupied by I, H66 is occupied by K, H67 is occupied by A, H69 is occupied by L, H71 is occupied by V, H73 is occupied by I, H75 is occupied by S, H80 is occupied by V, H82a is occupied by T, H82b is occupied by S, H83 is occupied by T, and H85 is occupied by E. In some such antibodies, positions H1, H5, H7, H9, H10, H11, H12, H13, H20, H40, H48, H66, H67, H69, H71, H73, H75, H80, H82a, H82b, H83, and H85 in the VH region are occupied by, E, Q, P, S, V, L, V, R, L, R, I, K, A, L, V, I, S, V, T, S, T, and E, respectively.

In some antibodies, at least one of the following positions in the VH region is occupied by the amino acid as specified: H1 is occupied by E, H5 is occupied by Q, H7 is occupied by P, H9 is occupied by S, H10 is occupied by V, H11 is occupied by L, H12 is occupied by V, H13 is occupied by R, H20 is occupied by L, H48 is occupied by I, H69 is occupied by L, H71 is occupied by V, H82a is occupied by T, H82b is occupied by S, H83 is occupied by T, and H85 is occupied by E. In some antibodies, positions H1, H5, H7, H9, H10, H11, H12, H13, H20, H48, H69, H71, H82a, H82b, H83, and H85 in the VH region are occupied by E, Q, P, S, V, L, V, R, L, I, L, V, T, S, T, and E, respectively.

In some antibodies at least one of the following positions in the VH region is occupied by the amino acid as specified: H1 is occupied by E, H5 is occupied by Q, H11 is occupied by L, H12 is occupied by V, H20 is occupied by L, H48 is occupied by I, H69 is occupied by L, H71 is occupied by V, H82a is occupied by T, H82b is occupied by S, H83 is occupied by T, and H85 is occupied by E. In some antibodies, H1, H5, H11, H12, H20, H48, H69, H71, H82a, H82b, H83, and H85 in the VH region are occupied by E, Q, L, V, L, I, L, V, T, S, T, and E, respectively.

In some antibodies, at least one of the following positions in the VH region is occupied by the amino acid as specified: H1 is occupied by E, H12 is occupied by V, H31 is occupied by G, H40 is occupied by R, H48 is occupied by I, H60 is occupied by A, H69 is occupied by L, H73 is occupied by I, and H83 is occupied by T. In some antibodies, positions H1, H12, H31, H40, H48, H60, H69, H73, and H83 in the VH region are occupied by are occupied by E, V, G, R, I, A, L, I, and T, respectively.

In some antibodies, at least one of the following positions in the VH region is occupied by the amino acid as specified: H1 is occupied by E, H12 is occupied by V, H40 is occupied by R, H48 is occupied by I, H69 is occupied by L, H73 is occupied by I, and H83 is occupied by T. In some antibodies, positions H1, H12, H40, H48, H69, H73, and H83 in the VH region are occupied by are occupied by E, V, R, I, L, I, and T, respectively.

In some antibodies, at least one of the following positions in the VH region is occupied by the amino acid as specified: H1 is occupied by E, H12 is occupied by V, H40 is occupied by R, H48 is occupied by I, H66 is occupied K, H67 is occupied by A, H69 is occupied by L, H71 is occupied by V, H73 is occupied by I, and H83 is occupied by T. In some antibodies, positions H1, H12, H40, H48, H66, H67, H69, H71, H73, and H83 in the VH region are occupied by are occupied by E, V, R, I, K, A, L, V, I, and T, respectively.

In some antibodies, at least one of the following positions in the VH region is occupied by the amino acid as specified: H1 is occupied by E, H12 is occupied by V, H40 is occupied by R, H48 is occupied by I, H69 is occupied by L, H73 is occupied by I, and H83 is occupied by T. In some antibodies, positions H1, H12, H40, H48, H69, H73, and H83 in the VH region are occupied by are occupied by E, V, R, I, L, I, and T, respectively. In some antibodies, at least one of the following positions in the VH region is occupied by the amino acid as specified: H7 is occupied by P, H71 is occupied by V, and H73 is occupied by I. In some antibodies, positions H7, H71, and H73 in the VH region are occupied by are occupied by P, V, and I, respectively. In some antibodies, at least one of the following positions in the VH region is occupied by the amino acid as specified: H31 is occupied by G and H60 is occupied by A. In some antibodies, positions H31 and H60 in the VH region are occupied by G and A, respectively. In some antibodies, at least one of the following positions in the VH region is occupied by the amino acid as specified: H1 is occupied by Q or E, H5 is occupied by V or Q, H7 is occupied by S or P, H9 is occupied by A or S, H10 is occupied by E or V, H11 is occupied V or L, H12 is occupied by K or V, H13 is occupied by K or R, H20 is occupied by V or L, H31 is occupied by G or S, H37 is occupied by V or A, H38 is occupied by R or K, H40 is occupied by A or R, H48 is occupied by M or I, H60 is occupied by A or N, H64 is occupied by Q or K, H66 is occupied by R or K, H67 is occupied by V or A, H69 is occupied by M or L, H71 is occupied by R or V, H73 is occupied by T or I, H75 is occupied by I, S, or A, H80 is occupied by M or V, H82a is occupied by S or T, H82b is occupied by R or S, H83 is occupied by R or T, and H85 is occupied by D or E. In some antibodies, positions H1, H5, H7, H9, H10, H11, H12, H13, H20, H37, H38, H40, H48, H66, H67, H69, H71, H73, H75, H80, H82a, H82b, H83, and H85 in the VH region are occupied by E, Q, P, S, V, L, V, R, L, A, K, R, I, K, A, L, V, I, S, V, T, S, T, and E, respectively. In some antibodies, positions H1, H5, H11, H12, H20, H48, H69, H71, H75, H82a, H82b, H83, and H85 in the VH region are occupied by E, Q, L, V, L, I, L, V, A, T, S, T, and E, respectively. In some antibodies, positions H1, H12, H40, H48, H66, H67, H69, H71, H73, and H83 in the VH region are occupied by E, V, R, I, K, A, L, V, I, and T, respectively. In some antibodies, positions H1, H12, H31, H40, H48, H60, H66, H67, H69, H71, H73, and H83 in the VH region are occupied by E, V, G, R, I, A, K, A, L, V, I, and T, respectively. In some antibodies, positions H1, H12, H40, H48, H69, H73, and H83 in the VH region are occupied by E, V, R, I, L, I, and T, respectively. In some antibodies, positions H1, H12, H31, H40, H48, H60, H66, H67, H69, H71, H73, and H83 in the VH region are occupied by Q, V, G, R, I, A, K, A, L, V, I, and T, respectively. In some antibodies, positions H1 and H7 and H73 in the VH region are occupied by Q, P, V and I, respectively. In some antibodies, positions H1, H12, H31, H40, H48, H60, H64, H69, H73, and H83 in the VH region are occupied by, E, V, G, R, I, A, Q, L, I, and T, respectively. In some antibodies, positions H1, H5, H7, H9, H10, H11, H12, H13, H20, H48, H69, H71, H75, H82a, H82b, H83, and H85 in the VH region are occupied by E, Q, P, S, V, L, V, R, L, I, L, V, A, T, S, T, and E. In some antibodies, positions H1, H5, H11, H12, H20, H48, H66, H67, H69, H71, H73, H75, H82a, H82b, H83, and H85 in the VH region are occupied by, E, Q, L, V, L, I, K, A, L, V, I, S, T, S, T, and E. In some antibodies, positions H1, H5, H7, H9, H10, H11, H12, H13, H20, H38, H40, H48, H66, H67, H69, H71, H73I, H75, H80, H82a, H82b, H83, and H85 in the VH region are occupied by E, Q, P, S, V, L, V, R, L, K, R, I, K, A, L, V, I, S, V, T, S, T, and E, respectively. In some antibodies, positions H1, H5, H7, H9, H10, H11, H12, H13, H20, H40, H48, H66, H67, H69, H71, H73, H75, H80, H82a, H82b, H83, and H85 in the VH region are occupied by Q, P, S, V, L, V, R, L, R, I, K, A, L, V, I, S, V, T, S, T, and E, respectively. In some antibodies, positions H7, H71, and H73 in the VH region are occupied by P, V, and I, respectively. In some antibodies, positions H71 in the VH region is occupied by V. In some antibodies, positions H1, H7, H71, and H73 in the VH region are occupied by E, P, V, and I.

In some antibodies, at least one of the following positions in the VL region is occupied by the amino acid as specified: L4 is occupied by L, L9 is occupied by S, L15 is occupied by V, L22 is occupied by S, and L43 is occupied by S. In some antibodies, positions L4, L9, L15, L22, and L43 in the VL region are occupied by L, S, V, S, and S, respectively.

In some antibodies, at least one of the following positions in the VL region is occupied by the amino acid as specified: L4 is occupied by L, L9 is occupied by S, L15 is occupied by V, L18 is occupied by K, L19 is occupied by V, L21 is occupied by M, L22 is occupied by S, and L43 is occupied by S. In some antibodies, L4, L9, L15, L18, L19, L21, L22, and L43 in the VL region are occupied by L, S, V, K, V, M, S, and S, respectively.

In some antibodies, at least one of the following positions in the VL region is occupied by the amino acid as specified: L4 is occupied by M or L, L9 is occupied by D or S, L15 is occupied by L or V, L18 is occupied by R or K, L19 is occupied by A or V, L21 is occupied by I or M, L22 is occupied by N or S, L43 is occupied by P or S, and L48 is occupied by I or M. In some antibodies, L4, L9, L15, L18, L19, L21, L22, and L43 in the VL region are occupied by L, S, V, K, V, M, S, and S, respectively.

In some antibodies, positions L4, L9, L15, L22, and L43 in the VL region are occupied by L, S, V, S, and S, respectively. In some antibodies, positions L4, L9, L15, L18, L19, L21, L22, and L43 in the VL region are occupied by L, S, V, K, V, M, S, and S, respectively.

Some antibodies comprise a mature heavy chain variable region having an amino acid sequence at least 95% identical to any one of SEQ ID NO: 15-27 and a mature light chain variable region having an amino acid sequence at least 95% identical to any one of SEQ ID NO: 28-30. Some antibodies comprise a mature heavy chain variable region having an amino acid sequence at least 98% identical to any one of SEQ ID NO: 15-27 and a mature light chain variable region having an amino acid sequence at least 98% identical to any one of SEQ ID NO: 28-30.

In some antibodies, the mature heavy chain variable region has an amino acid sequence of any of SEQ ID NO:15-27 and the mature light chain variable region has an amino acid sequence of any one of SEQ ID NO:28-30. In some antibodies, the mature heavy chain variable region has an amino acid sequence of SEQ ID NO:15 and the mature light chain variable region has an amino acid sequence of SEQ ID NO:28. In some antibodies, the mature heavy chain variable region has an amino acid sequence of SEQ ID NO:15 and the mature light chain variable region has an amino acid sequence of SEQ ID NO:29. In some antibodies, the mature heavy chain variable region has an amino acid sequence of SEQ ID NO:15 and the mature light chain variable region has an amino acid sequence of SEQ ID NO:30.

In some antibodies, the mature heavy chain variable region has an amino acid sequence of SEQ ID NO:16 and the mature light chain variable region has an amino acid sequence of SEQ ID NO:28. In some antibodies, the mature heavy chain variable region has an amino acid sequence of SEQ ID NO:16 and the mature light chain variable region has an amino acid sequence of SEQ ID NO:29. In some antibodies, the mature heavy chain variable region has an amino acid sequence of SEQ ID NO:16 and the mature light chain variable region has an amino acid sequence of SEQ ID NO:30.

In some antibodies, the mature heavy chain variable region has an amino acid sequence of SEQ ID NO:17 and the mature light chain variable region has an amino acid sequence of SEQ ID NO:28. In some antibodies, the mature heavy chain variable region has an amino acid sequence of SEQ ID NO:17 and the mature light chain variable region has an amino acid sequence of SEQ ID NO:29. In some antibodies, the mature heavy chain variable region has an amino acid sequence of SEQ ID NO:17 and the mature light chain variable region has an amino acid sequence of SEQ ID NO:30.

In some antibodies, the mature heavy chain variable region has an amino acid sequence of SEQ ID NO:18 and the mature light chain variable region has an amino acid sequence of SEQ ID NO:28. In some antibodies, the mature heavy chain variable region region has an amino acid sequence of SEQ ID NO:18 and the mature light chain variable region has an amino acid sequence of SEQ ID NO:29. In some antibodies, the mature heavy chain variable region has an amino acid sequence of SEQ ID NO:18 and the mature light chain variable region has an amino acid sequence of SEQ ID NO:30.

In some antibodies, the mature heavy chain variable region has an amino acid sequence of SEQ ID NO:19 and the mature light chain variable region has an amino acid sequence of SEQ ID NO:28. In some antibodies, the mature heavy chain variable region has an amino acid sequence of SEQ ID NO:19 and the mature light chain variable region has an amino acid sequence of SEQ ID NO:29. In some antibodies, the mature heavy chain variable region has an amino acid sequence of SEQ ID NO:19 and the mature light chain variable region has an amino acid sequence of SEQ ID NO:30.

In some antibodies, the mature heavy chain variable region has an amino acid sequence of SEQ ID NO:20 and the mature light chain variable region has an amino acid sequence of SEQ ID NO:28. In some antibodies, the mature heavy chain variable region has an amino acid sequence of SEQ ID NO:20 and the mature light chain variable region has an amino acid sequence of SEQ ID NO:29. In some antibodies, the mature heavy chain variable region has an amino acid sequence of SEQ ID NO:20 and the mature light chain variable region has an amino acid sequence of SEQ ID NO:30.

In some antibodies, the mature heavy chain variable region has an amino acid sequence of SEQ ID NO:21 and the mature light chain variable region has an amino acid sequence of SEQ ID NO:28. In some antibodies, the mature heavy chain variable region has an amino acid sequence of SEQ ID NO:21 and the mature light chain variable region has an amino acid sequence of SEQ ID NO:29. In some antibodies, the mature heavy chain variable region has an amino acid sequence of SEQ ID NO:21 and the mature light chain variable region has an amino acid sequence of SEQ ID NO:30.

In some antibodies, the mature heavy chain variable region an amino acid sequence of SEQ ID NO:22 and the mature light chain variable region has an amino acid sequence of SEQ ID NO:28. In some antibodies, the mature heavy chain variable region has an amino acid sequence of SEQ ID NO:22 and the mature light chain variable region has an amino acid sequence of SEQ ID NO:29. In some antibodies, the mature heavy chain variable region has an amino acid sequence of SEQ ID NO:22 and the mature light chain variable region has an amino acid sequence of SEQ ID NO:30.

In some antibodies, the mature heavy chain variable region has an amino acid sequence of SEQ ID NO:23 and the mature light chain variable region has an amino acid sequence of SEQ ID NO:28. In some antibodies, the mature heavy chain variable region has an amino acid sequence of SEQ ID NO:23 and the mature light chain variable region has an amino acid sequence of SEQ ID NO:29. In some antibodies, the mature heavy chain variable region has an amino acid sequence of SEQ ID NO:23 and the mature light chain variable region has an amino acid sequence of SEQ ID NO:30.

In some antibodies, the mature heavy chain variable region has an amino acid sequence of SEQ ID NO:24 and the mature light chain variable region has an amino acid sequence of SEQ ID NO:28. In some antibodies, the mature heavy chain variable region has an amino acid sequence of SEQ ID NO:24 and the mature light chain variable region has an amino acid sequence of SEQ ID NO:29. In some antibodies, the mature heavy chain variable region has an amino acid sequence of SEQ ID NO:24 and the mature light chain variable region has an amino acid sequence of SEQ ID NO:30.

In some antibodies, the mature heavy chain variable region has an amino acid sequence of SEQ ID NO:25 and the mature light chain variable region has an amino acid sequence of SEQ ID NO:28. In some antibodies, the mature heavy chain variable region has an amino acid sequence of SEQ ID NO:25 and the mature light chain variable region has an amino acid sequence of SEQ ID NO:29. In some antibodies, the mature heavy chain variable region has an amino acid sequence of SEQ ID NO:25 and the mature light chain variable region has an amino acid sequence of SEQ ID NO:30.

In some antibodies, the mature heavy chain variable region has an amino acid sequence of SEQ ID NO:26 and the mature light chain variable region has an amino acid sequence of SEQ ID NO:28. In some antibodies, the mature heavy chain variable region has an amino acid sequence of SEQ ID NO:26 and the mature light chain variable region has an amino acid sequence of SEQ ID NO:29. In some antibodies, the mature heavy chain variable region has an amino acid sequence of SEQ ID NO:26 and the mature light chain variable region has an amino acid sequence of SEQ ID NO:30.

In some antibodies, the mature heavy chain variable region has an amino acid sequence of SEQ ID NO:27 and the mature light chain variable region has an amino acid sequence of SEQ ID NO:28. In some antibodies, the mature heavy chain variable region has an amino acid sequence of SEQ ID NO:27 and the mature light chain variable region has an amino acid sequence of SEQ ID NO:29. In some antibodies, the mature heavy chain variable region has an amino acid sequence of SEQ ID NO:27 and the mature light chain variable region has an amino acid sequence of SEQ ID NO:30.

For example, the antibody can be a chimeric antibody. For example, the antibody can be a veneered antibody. The antibody can be an intact mouse, chimeric, veneered or humanized antibody or a binding fragment, single-chain antibody Fab fragment, Fab'2 fragment, or single chain Fv. Some of the antibodies have a human IgG1 isotype, while others may have a human IgG2 or IgG4 isotype. Some antibodies have the mature light chain variable region fused to a light chain constant region and the mature heavy chain variable region fused to a heavy chain constant region. The heavy chain constant region of some antibodies is a mutant form of a natural human heavy chain constant region which has reduced binding to a Fcγ receptor relative to the natural human heavy chain constant region.

Some antibodies may have at least one mutation in the constant region, such as a mutation that reduces complement fixation or activation by the constant region, for example, a mutation at one or more of positions 241, 264, 265, 270, 296, 297, 318, 320, 322, 329 and 331 by EU numbering. Some antibodies have an alanine at positions 318, 320 and 322. Some antibodies can be at least 95% w/w pure. The antibody can be conjugated to a therapeutic, cytotoxic, cytostatic, neurotrophic, or neuroprotective agent.

In another aspect, the invention provides a pharmaceutical composition comprising any of the antibodies disclosed herein and a pharmaceutically-acceptable carrier.

In another aspect, the invention provides a nucleic acid encoding the heavy chain and/or light chain of any of the antibodies disclosed herein, a recombinant expression vector comprising the nucleic acid and a host cell transformed with the recombinant expression vector.

In yet another aspect, the invention provides methods of humanizing any non-human antibody described herein, for example, mouse antibodies 16G7, wherein 16G7 is characterized by a mature heavy chain variable region of SEQ ID NO:7 and a mature light chain variable region of SEQ ID NO:11. Such methods can involve selecting one or more acceptor antibodies, synthesizing a nucleic acid encoding a humanized heavy chain comprising CDRs of the mouse heavy chain and a nucleic acid encoding a humanized light chain comprising CDRs of the mouse antibody light chain, and expressing the nucleic acids in a host cell to produce a humanized antibody.

Methods of producing antibodies, such as a humanized, chimeric or veneered antibody, for example humanized, chimeric or veneered forms of 16G7, are also provided. In such methods, cells transformed with nucleic acids encoding the heavy and light chains of the antibody are cultured so that the cells secrete the antibody. The antibody can then be purified from the cell culture media.

Cell lines producing any of the antibodies disclosed herein can be produced by introducing a vector encoding heavy and light chains of the antibody and a selectable marker into cells, propagating the cells under conditions to select for cells having increased copy number of the vector, isolating single cells from the selected cells; and banking cells cloned from a single cell selected based on yield of antibody.

Some cells can be propagated under selective conditions and screened for cell lines naturally expressing and secreting at least 100 mg/L/10⁶ cells/24 hours. Single cells can be isolated from the selected cells. Cells cloned from a single cell can then be banked Single cells can be selected based on desirable properties, such as the yield of the antibody. Exemplary cell lines are cell lines expressing 16G7.

The invention also provides methods of inhibiting or reducing aggregation of tau in a subject having or at risk of developing a tau-mediated amyloidosis, comprising administering to the subject an effective regime of an antibody disclosed herein, thereby inhibiting or reducing aggregation of tau in the subject. Exemplary antibodies include humanized versions of 16G7.

Also provided are methods of treating or effecting prophylaxis of a tau-related disease in a subject, comprising administering an effective regime of an antibody disclosed herein and thereby treating or effecting prophylaxis of the disease. Examples of such a disease are Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), or progressive supranuclear palsy (PSP). In some methods, the tau-related disease is Alzheimer's disease. In some methods the patient is an ApoE4 carrier.

Also provided are methods of reducing aberrant transmission of tau comprising administering an effective regime of an antibody disclosed herein and thereby reducing transmission of tau.

Also provided are methods of inducing phagocytosis of tau comprising administering an effective regime of an antibody disclosed herein and thereby inducing phagocytosis of tau.

Also provided are methods of inhibiting tau aggregation or deposition comprising administering an effective regime of an antibody disclosed herein thereby inhibiting tau aggregation or deposition.

Also provided are methods of inhibiting formation of tau tangles comprising administering an effective regime of an antibody disclosed herein.

The invention also provides a method of detecting tau protein deposits in a subject having or at risk of a disease associated with tau aggregation or deposition comprising administering to a subject an antibody disclosed herein, and detecting the antibody bound to tau in the subject. Examples of such a disease are Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), or progressive supranuclear palsy (PSP). In some embodiments, the antibody is administered by intravenous injection into the body of the subject. In some embodiments, the antibody is administered directly to the brain of the subject by intracranial injection or by drilling a hole through the skull of the subject. In some embodiments, the antibody is labeled. In some embodiments, the antibody is labeled with a fluorescent label, a paramagnetic label, or a radioactive label. In some embodiments, the radioactive label is detected using positron emission tomography (PET) or single-photon emission computed tomography (SPECT).

The invention also provides a method of measuring efficacy of treatment in a subject being treated for a disease associated with tau aggregation or deposition, comprising measuring a first level of tau protein deposits in the subject prior to treatment by administering to a subject an antibody disclosed herein, and detecting a first amount of the antibody bound to tau in the subject, administering the treatment to the subject, measuring a second level of tau protein deposits in the subject after treatment by administering to a subject the antibody, and detecting the antibody bound to tau in the subject, wherein a decrease in the level of tau protein deposits indicates a positive response to treatment.

The invention also provides a method of measuring efficacy of treatment in a subject being treated for a disease associated with tau aggregation or deposition, comprising measuring a first level of tau protein deposits in the subject prior to treatment by administering to a subject an antibody disclosed herein, and detecting a first amount of antibody bound to tau in the subject, administering the treatment to the subject, measuring a second level of tau protein deposits in the subject after treatment by administering to a subject the antibody, and detecting a second amount of antibody bound to tau in the subject, wherein no change in the level of tau protein deposits or a small increase in tau protein deposits indicates a positive response to treatment.

BRIEF DESCRIPTION OF THE DRAWINGS

FIG. 2 depicts an alignment of heavy chain variable regions of the mouse 16G7 antibody and humanized versions of the 16G7 antibody. The CDRs as defined by Kabat/Chothia Composite are in boldface. Positions in heavy chain variable regions of the mouse 16G7 antibody and humanized versions of the 16G7 antibody where amino acid residues differ from the "Majority" sequence are boxed.

FIGS. 8A-D depict exemplary humanized Vk designs, with backmutations and other mutations based on selected human frameworks. The bolded areas indicate the CDRs as defined by Kabat/Chothia Composite.

FIGS. 9A-E depict exemplary humanized Vh designs, with backmutations and other mutations based on selected human frameworks. The bolded areas indicate the CDRs as defined by Kabat/Chothia Composite.

BRIEF DESCRIPTION OF THE SEQUENCES

Figure 1:
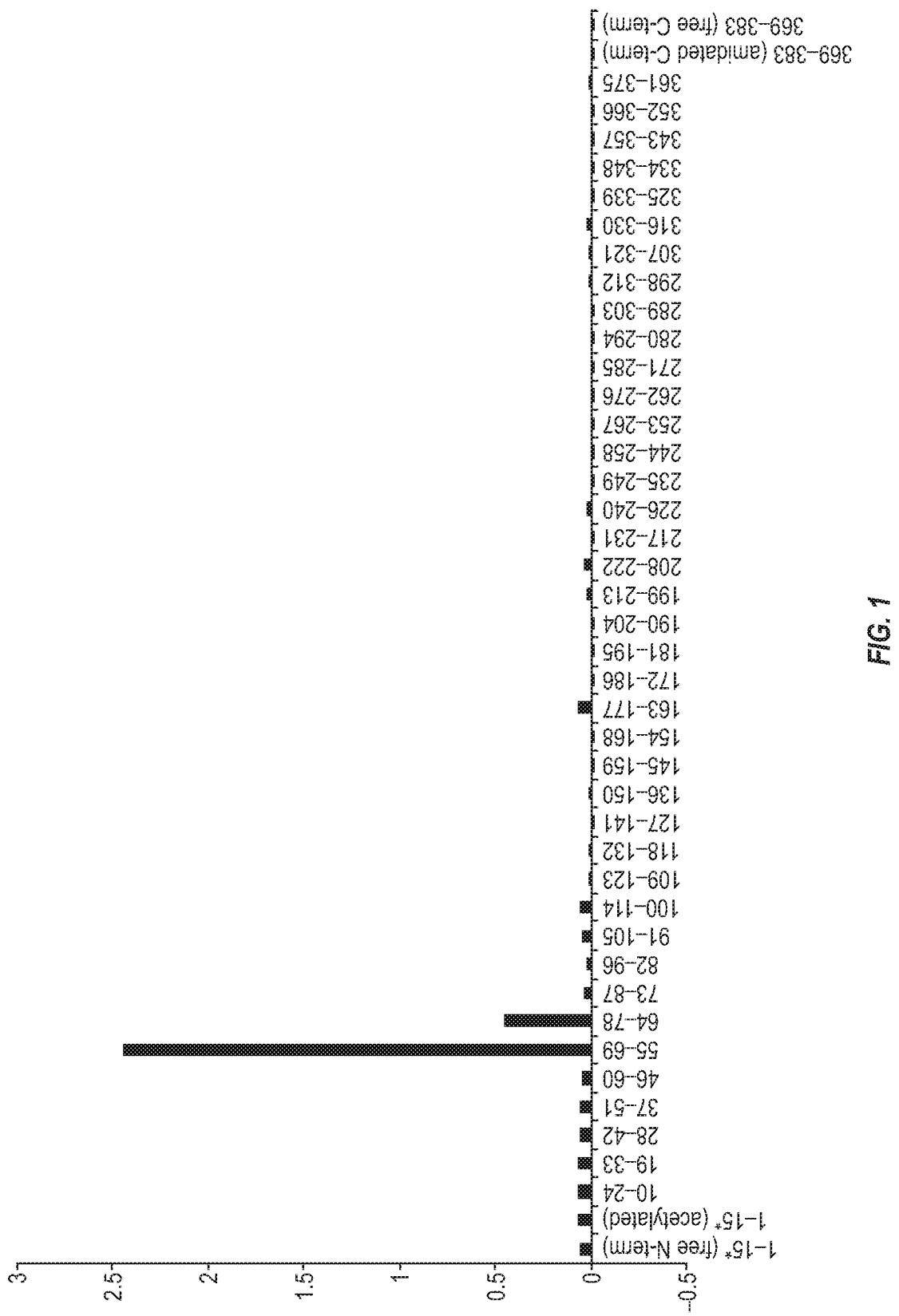
FIG. 1 depicts the results of experiments designed to map the epitope(s) bound by the murine 16G7 monoclonal antibody.

SEQ ID NO:1 sets forth the amino acid sequence of an isoform of human tau (Swiss-Prot P10636-8).

SEQ ID NO:2 sets forth the amino acid sequence of an isoform of human tau (Swiss-Prot P10636-7).

SEQ ID NO:3 sets forth the amino acid sequence of an isoform of human tau (Swiss-Prot P10636-6), (4R0N human tau).

SEQ ID NO:4 sets forth the amino acid sequence of an isoform of human tau (Swiss-Prot P10636-5).

SEQ ID NO:5 sets forth the amino acid sequence of an isoform of human tau (Swiss-Prot P10636-4).

SEQ ID NO:6 sets forth the amino acid sequence of an isoform of human tau (Swiss-Prot P10636-2).

SEQ ID NO: 7 sets forth the amino acid sequence of the heavy chain variable region of the mouse 16G7 antibody.

SEQ ID NO: 8 sets forth the amino acid sequence of Kabat/Chothia Composite CDR-H1 of the mouse 16G7 antibody.

SEQ ID NO:9 sets forth the amino acid sequence of Kabat CDR-H2 of the mouse 16G7 antibody.

SEQ ID NO: 10 sets forth the amino acid sequence of Kabat CDR-H3 of the mouse 16G7 antibody.

SEQ ID NO: 11 sets forth the amino acid sequence of the light chain variable region of the mouse 16G7 antibody.

SEQ ID NO: 12 sets forth the amino acid sequence of Kabat CDR-L1 of the mouse 16G7 antibody.

SEQ ID NO: 13 sets forth the amino acid sequence of Kabat CDR-L2 of the mouse 16G7 antibody.

SEQ ID NO: 14 sets forth the amino acid sequence of Kabat CDR-L3 of the mouse 16G7 antibody.

SEQ ID NO:15 sets forth the amino acid sequence of heavy chain variable region of the humanized 16G7 antibody hu16G7VHv1.

SEQ ID NO:16 sets forth the amino acid sequence of heavy chain variable region of the humanized 16G7 antibody hu16G7VHv2.

SEQ ID NO:17 sets forth the amino acid sequence of heavy chain variable region of the humanized 16G7 antibody hu16G7VHv2a.

SEQ ID NO:18 sets forth the amino acid sequence of heavy chain variable region of the humanized 16G7 antibody hu16G7VHv2aB7.

SEQ ID NO:19 sets forth the amino acid sequence of heavy chain variable region of the humanized 16G7 antibody hu16G7VHv2b.

SEQ ID NO:20 sets forth the amino acid sequence of heavy chain variable region of the humanized 16G7 antibody hu16G7VHv2bH7.

SEQ ID NO:21 sets forth the amino acid sequence of heavy chain variable region of the humanized 16G7 antibody hu16G7VHv3.

SEQ ID NO:22 sets forth the amino acid sequence of heavy chain variable region of the humanized 16G7 antibody hu16G7VHv4.

SEQ ID NO:23 sets forth the amino acid sequence of heavy chain variable region of the humanized 16G7 antibody hu16G7VHv5V.

SEQ ID NO:24 sets forth the amino acid sequence of heavy chain variable region of the humanized 16G7 antibody hu16G7VHv5VR.

SEQ ID NO:25 sets forth the amino acid sequence of heavy chain variable region of the humanized 16G7 antibody hu16G7VHv6a.

SEQ ID NO:26 sets forth the amino acid sequence of heavy chain variable region of the humanized 16G7 antibody hu16G7VHv6b.

SEQ ID NO:27 sets forth the amino acid sequence of heavy chain variable region of the humanized 16G7 antibody hu16G7VHv7.

SEQ ID NO:28 sets forth the amino acid sequence of the light chain variable region of the humanized 16G7 antibody hu16G7VLv1.

SEQ ID NO:29 sets forth the amino acid sequence of the light chain variable region of the humanized 16G7 antibody hu16G7VLv2.

SEQ ID NO:30 sets forth the amino acid sequence of the light chain variable region of the humanized 16G7 antibody hu16G7VLv3.

SEQ ID NO:31 sets forth the amino acid sequence of the heavy chain variable acceptor Acc. #AAA18265.1.

SEQ ID NO:32 sets forth the amino acid sequence of the heavy chain variable acceptor Acc. #ADW08092.1.

SEQ ID NO:33 sets forth the amino acid sequence of the heavy chain variable acceptor Acc. #IMGT #IGHV1-2*02.

SEQ ID NO:34 sets forth the amino acid sequence of the light chain variable acceptor Acc. #AAB24404.1.

SEQ ID NO:35 sets forth the amino acid sequence of the light chain variable acceptor Acc. #AEK69364.1.

SEQ ID NO:36 sets forth the amino acid sequence of the light chain variable acceptor Acc. #IMGT#IGKV4-1*01.

SEQ ID NO: 37 sets forth a nucleic acid sequence encoding the heavy chain variable region of the mouse 16G7 antibody.

SEQ ID NO: 38 sets forth a nucleic acid sequence encoding the light chain variable region of the mouse 16G7 antibody.

SEQ ID NO: 39 sets forth the amino acid sequence of Kabat CDR-H1 of the mouse 16G7 antibody.

SEQ ID NO: 40 sets forth the amino acid sequence of Chothia CDR-H1 of the mouse 16G7 antibody.

SEQ ID NO: 41 sets forth the amino acid sequence of Chothia CDR-H2 of the mouse 16G7 antibody.

SEQ ID NO: 42 sets forth the amino acid sequence of AbM CDR-H2 of the mouse 16G7 antibody.

SEQ ID NO: 43 sets forth the amino acid sequence of Contact CDR-L1 of the mouse 16G7 antibody.

SEQ ID NO: 44 sets forth the amino acid sequence of Contact CDR-L2 of the mouse 16G7 antibody.

SEQ ID NO: 45 sets forth the amino acid sequence of Contact CDR-L3 of the mouse 16G7 antibody.

SEQ ID NO: 46 sets forth the amino acid sequence of Contact CDR-H1 of the mouse 16G7 antibody.

SEQ ID NO: 47 sets forth the amino acid sequence of Contact CDR-H2 of the mouse 16G7 antibody.

SEQ ID NO: 48 sets forth the amino acid sequence of Contact CDR-H3 of the mouse 16G7 antibody.

SEQ ID NO: 49 sets forth the amino acid sequence of an alternate Kabat-Chothia Composite CDR-H1 of a humanized 16G7 antibody.

SEQ ID NO: 50 sets forth the amino acid sequence of an alternate Kabat CDR-H2 of a humanized 16G7 antibody.

SEQ ID NO: 51 sets forth the amino acid sequence of an alternate Kabat CDR-H2 of a humanized 16G7 antibody.

SEQ ID NO:52 sets forth the consensus amino acid sequence among the heavy chain variable regions of the mouse 16G7 and humanized 16G7 antibodies (labeled "Majority" in FIG. 2).

Figure 3:
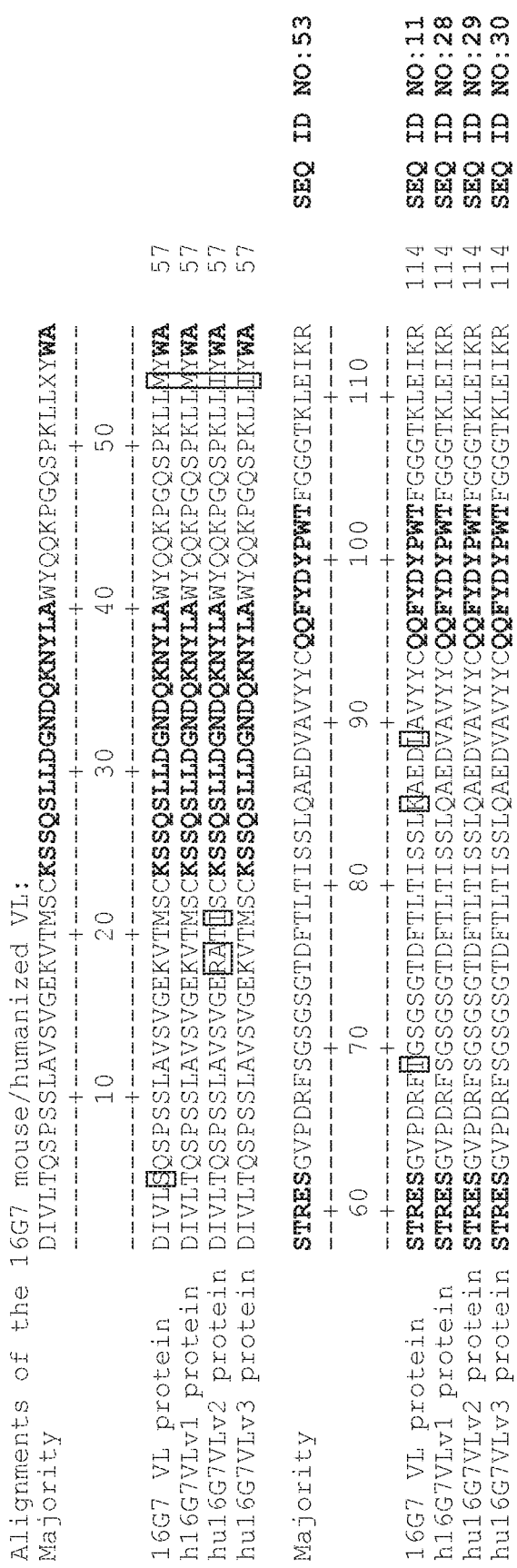
FIG. 3 depicts an alignment of light chain variable regions of the mouse 16G7 antibody and humanized versions of the 16G7 antibody. The CDRs as defined by Kabat are in boldface. Positions in light chain variable regions of the mouse 16G7 antibody and humanized versions of the 16G7 antibody where amino acid residues differ from the "Majority" sequence are boxed.

SEQ ID NO:53 sets forth the consensus amino acid sequence between the light chain variable regions of the mouse 16G7 and humanized 16G7 antibodies (labeled "Majority' in FIG. 3).

SEQ ID NO: 54 sets forth the amino acid sequence of the heavy chain of a chimeric 16G7 antibody.

SEQ ID NO: 55 sets forth the amino acid sequence of the light chain of a chimeric 16G7 antibody.

DEFINITIONS

Monoclonal antibodies or other biological entities are typically provided in isolated form. This means that an antibody or other biologically entity is typically at least 50% w/w pure of interfering proteins and other contaminants arising from its production or purification but does not exclude the possibility that the monoclonal antibody is combined with an excess of pharmaceutically acceptable carrier(s) or other vehicle intended to facilitate its use. Sometimes monoclonal antibodies are at least 60%, 70%, 80%, 90%, 95% or 99% w/w pure of interfering proteins and contaminants from production or purification. Often an isolated monoclonal antibody or other biological entity is the predominant macromolecular species remaining after its purification.

Specific binding of an antibody to its target antigen means an affinity and/or avidity of at least $10^6$, $10^7$, $10^8$, $10^9$, $10^{10}$, $10^{11}$, or $10^{12}$ M$^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that an antibody binds one and only one target.

The basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region means a light chain variable region without the light chain signal peptide. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. See generally, *Fundamental Immunology*, Paul, W., ed., 2nd ed. Raven Press, N.Y., 1989, Ch. 7 (incorporated by reference in its entirety for all purposes).

An immunoglobulin light or heavy chain variable region (also referred to herein as a "light chain variable domain" ("VL domain") or "heavy chain variable domain" ("VH domain"), respectively) consists of a "framework" region interrupted by three "complementarity determining regions" or "CDRs." The framework regions serve to align the CDRs for specific binding to an epitope of an antigen. The CDRs include the amino acid residues of an antibody that are primarily responsible for antigen binding. From amino-terminus to carboxyl-terminus, both VL and VH domains comprise the following framework (FR) and CDR regions: FR1, CDR1, FR2, CDR2, FR3, CDR3, and FR4. CDRs 1, 2, and 3 of a VL domain are also referred to herein, respectively, as CDR-L1, CDR-L2, and CDR-L3; CDRs 1, 2, and 3 of a VH domain are also referred to herein, respectively, as CDR-H1, CDR-H2, and CDR-H3.

The assignment of amino acids to each VL and VH domain is in accordance with any conventional definition of CDRs. Conventional definitions include, the Kabat definition (Kabat, *Sequences of Proteins of Immunological Interest* (National Institutes of Health, Bethesda, Md., 1987 and 1991), the Chothia definition (Chothia & Lesk, *J. Mol. Biol.* 196:901-917, 1987; Chothia et al., Nature 342:878-883, 1989); a composite of Chothia Kabat CDR in which CDR-H1 is a composite of Chothia and Kabat CDRs; the AbM definition used by Oxford Molecular's antibody modelling software; and, the contact definition of Martin et al (bioinfo.org.uk/abs) (see Table 1). Kabat provides a widely used numbering convention (Kabat numbering) in which corresponding residues between different heavy chains or between different light chains are assigned the same number. When an antibody is said to comprise CDRs by a certain definition of CDRs (e.g., Kabat) that definition specifies the minimum number of CDR residues present in the antibody (i.e., the Kabat CDRs). It does not exclude that other residues falling within another conventional CDR definition but outside the specified definition are also present. For example, an antibody comprising CDRs defined by Kabat includes among other possibilities, an antibody in which the CDRs contain Kabat CDR residues and no other CDR residues, and an antibody in which CDR H1 is a composite Chothia-Kabat CDR H1 and other CDRs contain Kabat CDR residues and no additional CDR residues based on other definitions.

TABLE 1

Conventional Definitions of CDRs Using Kabat Numbering

| Loop | Kabat | Chothia | Composite of Chothia & Kabat | AbM | Contact |
|---|---|---|---|---|---|
| L1 | L24 - - - L34 | L24 - - - L34 | L24 - - - L34 | L24 - - - L34 | L30 - - - L36 |
| L2 | L50 - - - L56 | L50 - - - L56 | L50 - - - L56 | L50 - - - L56 | L46 - - - L55 |
| L3 | L89 - - - L97 | L89 - - - L97 | L89 - - - L97 | L89 - - - L97 | L89 - - - L96 |
| H1 | H31 - - - H35B | H26 - - - H32 . . . H34* | H26 - - - H35B* | H26 - - - H35B | H30 - - - H35B |

TABLE 1-continued

Conventional Definitions of CDRs Using Kabat Numbering

| Loop | Kabat | Chothia | Composite of Chothia & Kabat | AbM | Contact |
|---|---|---|---|---|---|
| H2 | H50 - - - H65 | H52 - - - H56 | H50 - - - H65 | H50 - - - H58 | H47 - - - H58 |
| H3 | H95 - - - H102 | H95 - - - H102 | H95 - - - H102 | H95 - - - H102 | H93 - - - H101 |

*CDR-H1 by Chothia can end at H32, H33, or H34 (depending on the length of the loop). This is because the Kabat numbering scheme places insertions of extra residues at 35A and 35B, whereas Chothia numbering places them at 31A and 31B. If neither H35A nor H35B (Kabat numbering) is present, the Chothia CDR-H1 loop ends at H32. If only H35A is present, it ends at H33. If both H35A and H35B are present, it ends at H34.

The term "antibody" includes intact antibodies and binding fragments thereof. Typically, fragments compete with the intact antibody from which they were derived for specific binding to the target including separate heavy chains, light chains Fab, Fab', F(ab')$_2$, F(ab)c, Dabs, nanobodies, and Fv. Fragments can be produced by recombinant DNA techniques, or by enzymatic or chemical separation of intact immunoglobulins. The term "antibody" also includes a bispecific antibody and/or a humanized antibody. A bispecific or bifunctional antibody is an artificial hybrid antibody having two different heavy/light chain pairs and two different binding sites (see, e.g., Songsivilai and Lachmann, *Clin. Exp. Immunol.*, 79:315-321 (1990); Kostelny et al., *J. Immunol.*, 148:1547-53 (1992)). In some bispecific antibodies, the two different heavy/light chain pairs include a humanized 16G7 heavy chain/light chain pair and a heavy chain/light chain pair specific for a different epitope on tau than that bound by 16G7.

In some bispecific antibodies, one heavy chain/light chain pair is a humanized 16G7 antibody as further disclosed below and the other heavy chain/light chain pair is from an antibody that binds to a receptor expressed on the blood brain barrier, such as an insulin receptor, an insulin-like growth factor (IGF) receptor, a leptin receptor, or a lipoprotein receptor, or a transferrin receptor (Friden et al., *Proc. Natl. Acad. Sci. USA* 88:4771-4775, 1991; Friden et al., *Science* 259:373-377, 1993). Such a bispecific antibody can be transferred cross the blood brain barrier by receptor-mediated transcytosis. Brain uptake of the bispecific antibody can be further enhanced by engineering the bi-specific antibody to reduce its affinity to the blood brain barrier receptor. Reduced affinity for the receptor resulted in a broader distributioin in the brain (see, e.g., Atwal et al., *Sci. Trans. Med.* 3, 84ra43, 2011; Yu et al., *Sci. Trans. Med.* 3, 84ra44, 2011).

Exemplary bispecific antibodies can also be: (1) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: *Antibody Engineering*, Springer Berlin Heidelberg (2010)); (2) a Tandab, which is a fusion of two single chain diabodies resulting in a tetravalent bispecific antibody that has two binding sites for each of the target antigens; (3) a flexibody, which is a combination of scFvs with a diabody resulting in a multivalent molecule; (4) a so-called "dock and lock" molecule, based on the "dimerization and docking domain" in Protein Kinase A, which, when applied to Fabs, can yield a trivalent bispecific binding protein consisting of two identical Fab fragments linked to a different Fab fragment; or (5) a so-called Scorpion molecule, comprising, e.g., two scFvs fused to both termini of a human Fc-region. Examples of platforms useful for preparing bispecific antibodies include BiTE (Micromet), DART (MacroGenics), Fcab and Mab2 (F-star), Fc-engineered IgG1 (Xencor) or DuoBody (based on Fab arm exchange, Genmab).

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996).

Antibodies that recognize the same or overlapping epitopes can be identified in a simple immunoassay showing the ability of one antibody to compete with the binding of another antibody to a target antigen. The epitope of an antibody can also be defined X-ray crystallography of the antibody bound to its antigen to identify contact residues. Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., *Cancer Res.* 50:1495, 1990). A test antibody competes with a reference antibody if an excess of a test antibody (e.g., at least 2x, 5x, 10x, 20x or 100x) inhibits binding of the reference antibody by at least 50% as measured in a competitive binding assay. Some test antibodies inhibit binding of the references antibody by at least 75%, 90% or 99%. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

The term "pharmaceutically acceptable" means that the carrier, diluent, excipient, or auxiliary is compatible with the other ingredients of the formulation and not substantially deleterious to the recipient thereof.

The term "patient" includes human and other mammalian subjects that receive either prophylactic or therapeutic treatment.

An individual is at increased risk of a disease if the subject has at least one known risk-factor (e.g., genetic, biochemical, family history, and situational exposure) placing individuals with that risk factor at a statistically significant greater risk of developing the disease than individuals without the risk factor.

The term "biological sample" refers to a sample of biological material within or obtainable from a biological source, for example a human or mammalian subject. Such samples can be organs, organelles, tissues, sections of tissues, bodily fluids, peripheral blood, blood plasma, blood serum, cells, molecules such as proteins and peptides, and any parts or combinations derived therefrom. The term biological sample can also encompass any material derived by processing the sample. Derived material can include cells or their progeny. Processing of the biological sample may involve one or more of filtration, distillation, extraction, concentration, fixation, inactivation of interfering components, and the like.

The term "control sample" refers to a biological sample not known or suspected to include tau-related disease-affected regions, or at least not known or suspect to include diseased regions of a given type. Control samples can be obtained from individuals not afflicted with the tau-related disease. Alternatively, control samples can be obtained from patients afflicted with the tau-related disease. Such samples can be obtained at the same time as a biological sample thought to comprise the tau-related disease or on a different occasion. A biological sample and a control sample can both be obtained from the same tissue. Preferably, control samples consist essentially or entirely of normal, healthy regions and can be used in comparison to a biological sample thought to comprise tau-related disease-affected regions. Preferably, the tissue in the control sample is the same type as the tissue in the biological sample. Preferably, the tau-related disease-affected cells thought to be in the biological sample arise from the same cell type (e.g., neurons or glia) as the type of cells in the control sample.

The term "disease" refers to any abnormal condition that impairs physiological function. The term is used broadly to encompass any disorder, illness, abnormality, pathology, sickness, condition, or syndrome in which physiological function is impaired, irrespective of the nature of the etiology.

The term "symptom" refers to a subjective evidence of a disease, such as altered gait, as perceived by the subject. A "sign" refers to objective evidence of a disease as observed by a physician.

The term "positive response to treatment" refers to a more favorable response in an individual patient or average response in a population of patients relative to an average response in a control population not receiving treatment.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" or "including" one or more recited elements may include other elements not specifically recited. For example, a composition that "comprises" or "includes" an antibody may contain the antibody alone or in combination with other ingredients.

Designation of a range of values includes all integers within or defining the range, and all subranges defined by integers within the range.

Unless otherwise apparent from the context, the term "about" encompasses insubstantial variations, such as values within a standard margin of error of measurement (e.g., SEM) of a stated value.

Statistical significance means p≤0.05.

The singular forms of the articles "a," "an," and "the" include plural references unless the context clearly dictates otherwise. For example, the term "a compound" or "at least one compound" can include a plurality of compounds, including mixtures thereof.

DETAILED DESCRIPTION

I. General

The invention provides antibodies that bind to tau. Some antibodies specifically bind to an epitope within residues 55-78 of SEQ ID NO:3 (corresponding to residues 113-136 of SEQ ID NO:1), such as, for example, an epitope within residues 60-75 (corresponding to residues 118-133 of SEQ ID NO:1) or within residues 61-70 (corresponding to residues 119-128 of SEQ ID NO:1). Some such antibodies can specifically bind to two peptides, for example, a first peptide comprising residues 55-69 of SEQ ID NO:3 (corresponding to residues 113-127 of SEQ ID NO:1) as well as a second peptide comprising residues 64-78 (corresponding to residues 122-136 of SEQ ID NO:1). Some antibodies bind to tau irrespective of phosphorylation state. Some antibodies of the invention serve to inhibit or delay tau-associated pathologies and associated symptomatic deterioration. Although an understanding of mechanism is not required for practice of the invention, a reduction in toxicity may occur as a result of the antibody inducing phagocytosis of tau, inhibiting tau from inter or intramolecular aggregation, or from binding to other molecules, by stabilizing a non-toxic conformation, by inhibiting intercellular or intracellular transmission of pathogenic tau forms, by blockade of tau phosphorylation, by preventing binding of tau to cells, or by inducing proteolytic cleavage of tau, among other mechanisms. The antibodies of the invention or agents that induce such antibodies can be used in methods of treating or effecting prophylaxis of Alzheimer's and other diseases associated with tau.

II. Target Molecules

Unless otherwise apparent from the context, reference to tau means a natural human form of tau including all isoforms irrespective of whether posttranslational modification (e.g., phosphorylation, glycation, or acetylation) is present. There are six major isoforms (splice variants) of tau occurring in the human brain. The longest of these variants has 441 amino acids, of which the initial met residue is cleaved. Residues are numbered according to the 441 isoform. Thus, for example, reference to a phosphorylation at position 404 means position 404 of the 441 isoform, or corresponding position of any other isoform when maximally aligned with the 441 isoform. The amino acid sequences of the isoforms and Swiss-Prot numbers are indicated below.

P10636-8

(SEQ ID NO: 1)

```
        10         20         30         40         50         60
MAEPRQEFEV MEDHAGTYGL GDRKDQGGYT MHQDQEGDTD AGLKESPLQT PTEDGSEEPG 70         80         90        100        110        120
SETSDAKSTP TAEDVTAPLV DEGAPGKQAA AQPHTEIPEG TTAEEAGIGD TPSLEDEAAG 130        140        150        160        170        180
HVTQARMVSK SKDGTGSDDK KAKGADGKTK IATPRGAAPP GQKGQANATR IPAKTPPAPK 190        200        210        220        230        240
TPPSSGEPPK SGDRSGYSSP GSPGTPGSRS RTPSLPTPPT REPKKVAVVR TPPKSPSSAK 250        260        270        280        290        300
SRLQTAPVPM PDLKNVKSKI GSTENLKHQP GGGKVQIINK KLDLSNVQSK CGSKDNIKHV 310        320        330        340        350        360
PGGGSVQIVY KPVDLSKVTS KCGSLGNIHH KPGGGQVEVK SEKLDFKDRV QSKIGSLDNI 370        380        390        400        410        420
THVPGGGNKK IETHKLTFRE NAKAKTDHGA EIVYKSPVVS GDTSPRHLSN VSSTGSIDMV 430        440
DSPQLATLAD EVSASLAKQG L
```

P10636-7

(SEQ ID NO: 2)

```
        10         20         30         40         50         60
MAEPRQEFEV MEDHAGTYGL GDRKDQGGYT MHQDQEGDTD AGLKESPLQT PTEDGSEEPG 70         80         90        100        110        120
SETSDAKSTP TAEAEEAGIG DTPSLEDEAA GHVTQARMVS KSKDGTGSDD KKAKGADGKT 130        140        150        160        170        180
KIATPRGAAP PGQKGQANAT RIPAKTPPAP KTPPSSGEPP KSGDRSGYSS PGSPGTPGSR 190        200        210        220        230        240
SRTPSLPTPP TREPKKVAVV RTPPKSPSSA KSRLQTAPVP MPDLKNVKSK IGSTENLKHQ 250        260        270        280        290        300
PGGGKVQIIN KKLDLSNVQS KCGSKDNIKH VPGGGSVQIV YKPVDLSKVT SKCGSLGNIH 310        320        330        340        350        360
HKPGGGQVEV KSEKLDFKDR VQSKIGSLDN ITHVPGGGNK KIETHKLTFR ENAKAKTDHG 370        380        390        400        410
AEIVYKSPVV SGDTSPRHLS NVSSTGSIDM VDSPQLATLA DEVSASLAKQ GL
```

P10636-6 (4R0N human tau)

(SEQ ID NO: 3)

```
        10         20         30         40         50         60
MAEPRQEFEV MEDHAGTYGL GDRKDQGGYT MHQDQEGDTD AGLKAEEAGI GDTPSLEDEA 70         80         90        100        110        120
AGHVTQARMV SKSKDGTGSD DKKAKGADGK TKIATPRGAA PPGQKGQANA TRIPAKTPPA 130        140        150        160        170        180
PKTPPSSGEP PKSGDRSGYS SPGSPGTPGS RSRTPSLPTP PTREPKKVAV VRTPPKSPSS 190        200        210        220        230        240
AKSRLQTAPV PMPDLKNVKS KIGSTENLKH QPGGGKVQII NKKLDLSNVQ SKCGSKDNIK 250        260        270        280        290        300
HVPGGGSVQI VYKPVDLSKV TSKCGSLGNI HHKPGGGQVE VKSEKLDFKD RVQSKIGSLD 310        320        330        340        350        360
NITHVPGGGN KKIETHKLTF RENAKAKTDH GAEIVYKSPV VSGDTSPRHL SNVSSTGSID 370        380
MVDSPQLATL ADEVSASLAK QGL
```

P10636-5

(SEQ ID NO: 4)

```
        10         20         30         40         50         60
MAEPRQEFEV MEDHAGTYGL GDRKDQGGYT MHQDQEGDTD AGLKESPLQT PTEDGSEEPG 70         80         90        100        110        120
SETSDAKSTP TAEDVTAPLV DEGAPGKQAA AQPHTEIPEG TTAEEAGIGD TPSLEDEAAG 130        140        150        160        170        180
```

-continued
```

HVTQARMVSK SKDGTGSDDK KAKGADGKTK IATPRGAAPP GQKGQANATR IPAKTPPAPK 190        200        210        220        230        240
TPPSSGEPPK SGDRSGYSSP GSPGTPGSRS RTPSLPTPPT REPKKVAVVR TPPKSPSSAK 250        260        270        280        290        300
SRLQTAPVPM PDLKNVKSKI GSTENLKHQP GGGKVQIVYK PVDLSKVTSK CGSLGNIHHK 310        320        330        340        350        360
PGGGQVEVKS EKLDFKDRVQ SKIGSLDNIT HVPGGGNKKI ETHKLTFREN AKAKTDHGAE 370        380        390        400        410
IVYKSPVVSG DTSPRHLSNV SSTGSIDMVD SPQLATLADE VSASLAKQGL
```

P10636-4
```
                                                       (SEQ ID NO: 5)
        10         20         30         40         50         60
MAEPRQEFEV MEDHAGTYGL GDRKDQGGYT MHQDQEGDTD AGLKESPLQT PTEDGSEEPG 70         80         90        100        110        120
SETSDAKSTP TAEAEEAGIG DTPSLEDEAA GHVTQARMVS KSKDGTGSDD KKAKGADGKT 130        140        150        160        170        180
KIATPRGAAP PGQKGQANAT RIPAKTPPAP KTPPSSGEPP KSGDRSGYSS PGSPGTPGSR 190        200        210        220        230        240
SRTPSLPTPP TREPKKVAVV RTPPKSPSSA KSRLQTAPVP MPDLKNVKSK IGSTENLKHQ 250        260        270        280        290        300
PGGGKVQIVY KPVDLSKVTS KCGSLGNIHH KPGGGQVEVK SEKLDFKDRV QSKIGSLDNI 310        320        330        340        350        360
THVPGGGNKK IETHKLTFRE NAKAKTDHGA EIVYKSPVVS GDTSPRHLSN VSSTGSIDMV 370        380
DSPQLATLAD EVSASLAKQG L
```

P10636-2
```
                                                       (SEQ ID NO: 6)
  10         20         30         40         50         60
MAEPRQEFEV MEDHAGTYGL GDRKDQGGYT MHQDQEGDTD AGLKAEEAGI GDTPSLEDEA 70         80         90        100        110        120
AGHVTQARMV SKSKDGTGSD DKKAKGADGK TKIATPRGAA PPGQKGQOANA TRIPAKTPPA 130        140        150        160        170        180
PKTPPSSGEP PKSGDRSGYS SPGSPGTPGS RSRTPSLPTP PTREPKKVAV VRTPPKSPSS 190        200        210        220        230        240
AKSRLQTAPV PMPDLKNVKS KIGSTENLKH QPGGGKVQIV YKPVDLSKVT SKCGSLGNIH 250        260        270        280        290        300
HKPGGGQVEV KSEKLDFKDR VQSKIGSLDN ITHVPGGGNK KIETHKLTFR ENAKAKTDHG 310        320        330        340        350
AEIVYKSPVV SGDTSPRHLS NVSSTGSIDM VDSPQLATLA DEVSASLAKQ GL
```

Reference to tau includes known natural variations about 30 of which are listed in the Swiss-Prot database and permutations thereof, as well as mutations associated with tau pathologies, such as dementia, Pick's disease, supranuclear palsy, etc. (see, e.g., Swiss-Prot database and Poorkaj, et al. Ann Neurol. 43:815-825 (1998)). Some examples of tau mutations numbered by the 441 isoform are a lysine to threonine mutation at amino acid residue 257 (K257T), an isoleucine to valine mutation at amino acid position 260 (1260V); a glycine to valine mutation at amino acid position 272 (G272V); an asparagine to lysine mutation at amino acid position 279 (N279K); an asparagine to histidine mutation at amino acid position 296 (N296H); a proline to serine mutation at amino acid position 301 (P301S); a proline to leucine mutation at amino acid position 301 (P301L); a glycine to valine mutation at amino acid position 303 (G303V); a serine to asparagine mutation at position 305 (S305N); a glycine to serine mutation at amino acid position 335 (G335S); a valine to methionine mutation at position 337 (V337M); a glutamic acid to valine mutation at position 342 (E342V); a lysine to isoleucine mutation at amino acid position 369 (K369I); a glycine to arginine mutation at amino acid position 389 (G389R); and an arginine to tryptophan mutation at amino acid position 406 (R406W).

Tau can be phosphorylated at one or more amino acid residues including tyrosine at amino acid positions 18, 29, 97, 310, and 394 serine at amino acid positions 184, 185, 198, 199, 202, 208, 214, 235, 237, 238, 262, 293, 324, 356, 396, 400, 404, 409, 412, 413, and 422; and threonine at amino acids positions 175, 181, 205, 212, 217, 231, and 403. Unless otherwise apparent from context, reference to tau, or their fragments includes the natural human amino acid sequences including isoforms, mutants, and allelic variants thereof.

IV. Antibodies

A. Binding Specificity and Functional Properties

The invention provides antibodies that bind to tau. Some antibodies specifically bind to an epitope within residues 55-78 of SEQ ID NO:3 (corresponding to residues of 113-136 of SEQ ID NO:1), such as, for example, an epitope within residues 60-75 of SEQ ID NO:3 (corresponding to residues 118-133 of SEQ ID NO:1) or within residues 61-70 of SEQ ID NO:3 (corresponding to residues 119-128 of SEQ ID NO:1). Some antibodies bind to tau irrespective of phosphorylation state. These antibodies can be obtained by immunizing with a tau polypeptide purified from a natural source or recombinantly expressed. Antibodies can be screened for binding tau in unphosphorylated form as well as a form in which one or more residues susceptible to phosphorylation are phosphorylated. Such antibodies preferably bind with indistinguishable affinities or at least within a factor of 1.5, 2 or 3-fold to phosphorylated tau compared to non-phosphorylated tau (i.e., are "pan-specific"). 16G7 is an example of a pan-specific monoclonal antibody. The invention also provides antibodies binding to the same epitope as any of the foregoing antibodies, such as, for example, the epitope of 16G7. Also included are antibodies competing for binding to tau with any of the foregoing antibodies, such as, for example, competing with 16G7.

The above-mentioned antibodies can be generated de novo by immunizing with a peptide including residues 55-78, 55-69, or 64-78 of SEQ ID NO: 3 (corresponding to residues 113-136, 113-127, or 122-136, respectively, of SEQ ID NO:1) or by immunizing with a full length tau polypeptide or fragment thereof comprising such residues and screening for specific binding to a peptide including such residues. Such peptides are preferably attached to a heterologous conjugate molecule that helps elicit an antibody response to the peptide. Attachment can be direct or via a spacer peptide or amino acid. Cysteine is used as a spacer amino acid because its free SH group facilitates attachment of a carrier molecule. A polyglycine linker (e.g., 2-6 glycines), with or without a cysteine residue between the glycines and the peptide can also be used. The carrier molecule serves to provide a T-cell epitope that helps elicit an antibody response against the peptide. Several carriers are commonly used particularly keyhole limpet hemocyanin (KLH), ovalbumin and bovine serum albumin (BSA). Peptide spacers can be added to peptide immunogen as part of solid phase peptide synthesis. Carriers are typically added by chemical cross-linking Some examples of chemical crosslinkers that can be used include cross-N-maleimido-6-aminocaproyl ester or m-maleimidobenzoyl-N-hydroxysuccinimide ester (MBS) (see for example, Harlow, E. et al., Antibodies: A Laboratory Manual, Cold Spring Harbor Laboratory Press, Cold Spring Harbor, N.Y. 1988; Sinigaglia et al., Nature, 336:778-780 (1988); Chicz et al., J. Exp. Med., 178:27-47 (1993); Hammer et al., Cell 74:197-203 (1993); Falk K. et al., Immunogenetics, 39:230-242 (1994); WO 98/23635; and, Southwood et al. J. Immunology, 160: 3363-3373 (1998)). The carrier and spacer if present can be attached to either end of the immunogen.

A peptide with optional spacer and carrier can be used to immunize laboratory animals or B-cells as described in more detail below. Hybridoma supernatants can be tested for ability to bind one or more peptides including residues 55-78, 55-69, or 64-78 of SEQ ID NO: 3 (corresponding to residues 113-136, 113-127, or 122-136, respectively, of SEQ ID NO:1) and/or phosphorylated and non-phosphorylated forms of tau, such as, for example, a full-length isoform of tau with position 404 in phosphorylated form. The peptide can be attached to a carrier or other tag to facilitate the screening assay. In this case, the carrier or tag is preferentially different than the combination of spacer and carrier molecule used for immunization to eliminate antibodies specific for the spacer or carrier rather than the tau peptide. Any of the tau isoforms can be used.

The invention provides monoclonal antibodies binding to epitopes within tau. An antibody designated 16G7 is one such exemplary mouse antibody. Unless otherwise apparent from context, reference to 16G7 should be understood as referring to any of the mouse, chimeric, veneered, and humanized forms of this antibody. The antibody has been deposited as [DEPOSIT NUMBER]. This antibody specifically binds within amino acid residues 55-78, 55-69, or 64-78 of SEQ ID NO: 3 (corresponding to residues 113-136, 113-127, or 122-136, respectively, of SEQ ID NO:1). This antibody is further characterized by its ability to bind both phosphorylated and unphosphorylated tau, both non-pathological and pathological forms and conformations of tau, and misfolded/aggregated forms of tau.

Some antibodies of the invention bind to the same or overlapping epitope as an antibody designated 16G7. The sequences of the heavy and light chain mature variable regions of this antibody are designated SEQ ID NO: 7 and SEQ ID NO:11, respectively. Other antibodies having such a binding specificity can be produced by immunizing mice with tau or a portion thereof including the desired epitope and screening resulting antibodies for binding to tau optionally in competition with an antibody having the variable regions of mouse 16G7 (IgG1 kappa). Fragments of tau including the desired epitope can be linked to a carrier that helps elicit an antibody response to the fragment and/or be combined with an adjuvant the helps elicit such a response. Such antibodies can be screened for differential binding to tau or a fragment thereof compared with mutants of specified residues. Screening against such mutants more precisely defines the binding specificity to allow identification of antibodies whose binding is inhibited by mutagenesis of particular residues and which are likely to share the functional properties of other exemplified antibodies. The mutations can be systematic replacement substitution with alanine (or serine if an alanine is present already) one residue at a time, or more broadly spaced intervals, throughout the target or throughout a section thereof in which an epitope is known to reside. If the same set of mutations significantly reduces the binding of two antibodies, the two antibodies bind the same epitope.

Antibodies having the binding specificity of a selected murine antibody (e.g., 16G7) can also be produced using a variant of the phage display method. See Winter, WO 92/20791. This method is particularly suitable for producing human antibodies. In this method, either the heavy or light chain variable region of the selected murine antibody is used as a starting material. If, for example, a light chain variable region is selected as the starting material, a phage library is constructed in which members display the same light chain variable region (i.e., the murine starting material) and a different heavy chain variable region. The heavy chain variable regions can for example be obtained from a library of rearranged human heavy chain variable regions. A phage showing strong specific binding for tau or a fragment thereof (e.g., at least $10^8$ and preferably at least $10^9$ $M^{-1}$) is selected. The heavy chain variable region from this phage then serves as a starting material for constructing a further phage library. In this library, each phage displays the same heavy chain variable region (i.e., the region identified from the first display library) and a different light chain variable region. The light chain variable regions can be obtained for example from a library of rearranged human variable light chain regions. Again, phage showing strong specific binding for tau are selected. The resulting antibodies usually have the same or similar epitope specificity as the murine starting material.

Kabat/Chothia Composite CDRs of the heavy chain of 16G7 are designated SEQ ID NOs: 8, 9, and 10, respectively, and Kabat CDRs of the light chain of 16G7 are designated SEQ ID NOs: 12, 13, and 14, respectively.

TABLE 2

16G7 CDRs as defined by Kabat, Chothia, Composite of Chothia and Kabat, AbM, and Contact

| Loop | Kabat | Chothia | Composite of Chothia & Kabat | AbM | Contact |
|------|-------|---------|------------------------------|-----|---------|
| L1 | L24 - - - L34 | L24 - - - L34 | L24 - - - L34 | L24 - - - L34 | L30 - - - L36 |
|    | SEQ ID NO: 12 | SEQ ID NO: 12 | SEQ ID NO: 12 | SEQ ID NO: 12 | SEQ ID NO: 43 |
| L2 | L50 - - - L56 | L50 - - - L56 | L50 - - - L56 | L50 - - - L56 | L46 - - - L55 |
|    | SEQ ID NO: 13 | SEQ ID NO: 13 | SEQ ID NO: 13 | SEQ ID NO: 13 | SEQ ID NO: 44 |
| L3 | L89 - - - L97 | L89 - - - L97 | L89 - - - L97 | L89 - - - L97 | L89 - - - L96 |
|    | SEQ ID NO: 14 | SEQ ID NO: 14v | SEQ ID NO: 14 | SEQ ID NO: 14 | SEQ ID NO: 45 |
| H1 | H31 - - - H35B | H26 - - - H32 | H26 - - - H35B | H26 - - - H35B | H30 - - - H35B |
|    | SEQ ID NO: 39 | SEQ ID NO: 40 | SEQ ID NO: 8 | SEQ ID NO: 8 | SEQ ID NO: 46 |
| H2 | H50 - - - H65 | H52 - - - H56 | H50 - - - H65 | H50 - - - H58 | H47 - - - H58 |
|    | SEQ ID NO: 9 | SEQ ID NO: 41 | SEQ ID NO: 9 | SEQ ID NO: 42 | SEQ ID NO: 47 |
| H3 | H95 - - - H102 | H95 - - - H102 | H95 - - - H102 | H95 - - - H102 | H93 - - - H101 |
|    | SEQ ID NO: 10 | SEQ ID NO: 10 | SEQ ID NO: 10 | SEQ ID NO: 10 | SEQ ID NO: 48 |

Other antibodies can be obtained by mutagenesis of cDNA encoding the heavy and light chains of an exemplary antibody, such as 16G7. Monoclonal antibodies that are at least 70%, 80%, 90%, 95%, 96%, 97%, 98%, or 99% identical to 16G7 in amino acid sequence of the mature heavy and/or light chain variable regions and maintain its functional properties, and/or which differ from the respective antibody by a small number of functionally inconsequential amino acid substitutions (e.g., conservative substitutions), deletions, or insertions are also included in the invention. Monoclonal antibodies having at least one or all six CDR(s) as defined by any conventional definition, but preferably Kabat, that are 90%, 95%, 99% or 100% identical to corresponding CDRs of 16G7 are also included.

The invention also provides antibodies having some or all (e.g., 3, 4, 5, and 6) CDRs entirely or substantially from 16G7. Such antibodies can include a heavy chain variable region that has at least two, and usually all three, CDRs entirely or substantially from the heavy chain variable region of 16G7 and/or a light chain variable region having at least two, and usually all three, CDRs entirely or substantially from the light chain variable region of 16G7. The antibodies can include both heavy and light chains. A CDR is substantially from a corresponding 16G7 CDR when it contains no more than 4, 3, 2, or 1 substitutions, insertions, or deletions, except that CDR-H2 (when defined by Kabat) can have no more than 6, 5, 4, 3, 2, or 1 substitutions, insertions, or deletions. Such antibodies can have at least 70%, 80%, 90%, 95%, 96%, 97%, 98%, or 99% identity to 16G7 in the amino acid sequence of the mature heavy and/or light chain variable regions and maintain their functional properties, and/or differ from 16G7 by a small number of functionally inconsequential amino acid substitutions (e.g., conservative substitutions), deletions, or insertions.

Some antibodies identified by such assays can bind to monomeric, misfolded, aggregated, phosphorylated, or unphosphorylated forms of tau or otherwise. Likewise, some antibodies are immunoreactive on non-pathological and pathological forms and conformations of tau.

B. Non-Human Antibodies

The production of other non-human antibodies, e.g., murine, guinea pig, primate, rabbit or rat, against tau or a fragment thereof (e.g., amino acid residues 55-78, 60-75, 61-70, 55-69, or 64-78 of SEQ ID NO: 3, corresponding to amino acid residues 113-136, 118-133, 119-128, 113-127, or 122-136, respectively, of SEQ ID NO:1) can be accomplished by, for example, immunizing the animal with tau or a fragment thereof. See Harlow & Lane, Antibodies, *A Laboratory Manual* (CSHP NY, 1988) (incorporated by reference for all purposes). Such an immunogen can be obtained from a natural source, by peptide synthesis, or by recombinant expression. Optionally, the immunogen can be administered fused or otherwise complexed with a carrier protein. Optionally, the immunogen can be administered with an adjuvant. Several types of adjuvant can be used as described below. Complete Freund's adjuvant followed by incomplete adjuvant is preferred for immunization of laboratory animals. Rabbits or guinea pigs are typically used for making polyclonal antibodies. Mice are typically used for making monoclonal antibodies. Antibodies are screened for specific binding to tau or an epitope within tau (e.g., an epitope comprising one or more of amino acid residues 55-78, 60-75, or 61-70 of SEQ ID NO:3 (corresponding to amino acid residues 113-136, 118-133, or 119-128, respectively, of SEQ ID NO:1). Such screening can be accomplished by determining binding of an antibody to a collection of tau variants, such as tau variants containing amino acid residues 55-78, 60-75, 61-70, 55-69, or 64-78 of SEQ ID NO:3 (corresponding to amino acid residues 113-136, 118-133, 119-128, 113-127, or 122-136, respectively, of SEQ ID NO:1) or mutations within these residues, and determining which tau variants bind to the antibody. Binding can be assessed, for example, by Western blot, FACS or ELISA.

C. Humanized Antibodies

A humanized antibody is a genetically engineered antibody in which CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539; Carter, U.S. Pat. No. 6,407,213; Adair, U.S. Pat. No. 5,859,205; and Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having at least three, four, five or all CDRs entirely or substantially from a donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by any conventional definition but preferably defined by Kabat) are identical between the respective CDRs. The variable region framework sequences of an antibody chain or the constant region of an antibody chain are substantially from a human variable region framework sequence or human constant region respectively when at least 85%, 90%, 95% or 100% of corresponding residues defined by Kabat are identical. To be classified as humanized under the 2014 World Health Organization (WHO) International non-proprietary names (INN) definition of humanized antibodies, an antibody must have at least 85% identity to human germline antibody sequences (i.e., prior to somatic hypermutation). Mixed antibodies are antibodies for which one antibody chain (e.g., heavy chain) meets the threshold but the other chain (e.g., light chain) does not meet the threshold. An antibody is classified as chimeric if neither chain meets the threshold, even though the variable framework regions for both chains were substantially human with some murine backmutations. See, Jones et al. (2016) The INNs and outs of antibody nonproprietary names, mAbs 8:1, 1-9, DOI: 10.1080/19420862.2015.1114320. See also "WHO-INN: International nonproprietary names (INN) for biological and biotechnological substances (a review)" (Internet) 2014. Available from: http://www.whoint/medicines/services/inn/BioRev2014.pdf), incorporated herein by reference. For the avoidance of doubt, the term $^3$humanized$^2$ as used herein is not intended to be limited to the 2014 WHO INN definition of humanized antibodies. Some of the humanized antibodies provided herein have at least 85% sequence identity to human germline sequences and some of the humanized antibodies provided herein have less than 85% sequence identity to human germline sequences. Some of the heavy chains of the humanized antibodies provided herein have from about 60% to 100% sequence identity to human germ line sequences, such as, for example, in the range of about 60% to 69%, 70% to 79%, 80% to 84%, or 85% to 89%. Some heavy chains fall below the 2014 WHO INN definition and have, for example, about 64%, 65%, 66%, 67%, 68%, 69%, 70%, 71%, 72%, 73%, 74%, 75%, 76%, 77%, 78%, 79%, 80%, 81%, 82%, 83%, or 84% sequence identity to human germ line sequences, while other heavy chains meet the 2014 WHO INN definition and have about 85%, 86%, 87%, 88%, 89% or greater sequence identity to human germ line sequences. Some of the light chains of the humanized antibodies provided herein have from about 60% to 100% sequence identity to human germ line sequences, such as, for example, in the range of about 80% to 84% or 85% to 89%. Some light chains fall below the 2014 WHO INN definition and have, for example, about 81%, 82%, 83% or 84% sequence identity to human germ line sequences, while other light chains meet the 2014 WHO INN definition and have about 85%, 86%, 87%, 88%, 89% or greater sequence identity to human germ line sequences. Some humanized antibodies provided herein that are "chimeric" under the 2014 WHO INN definition have heavy chains with less than 85% identity to human germ line sequences paired with light chains having less than 85% identity to human germ line sequences. Some humanized antibodies provided herein are "mixed" under the 2014 WHO INN definition, for example, having a heavy chain with at least 85% sequence identity to human germ line sequences paired with a light chain having less than 85% sequence identity to human germ line sequences, or vice versa. Some humanized antibodies provided herein meet the 2014 WHO INN definition of "humanized" and have a heavy chain with at least 85% sequence identity to human germ line sequences paired with a light chain having at least 85% sequence identity to human germ line sequences. Exemplary antibodies that meet the 2014 WHO INN definition of "humanized" include antibodies having a mature light chain with the amino acid sequence of SEQ ID NO:29 paired with a mature heavy chain sequence having an amino acid sequence of SEQ ID NO:20, SEQ ID NO:25, SEQ ID NO:26 or SEQ ID NO:27. Additional humanized antibodies of the invention include antibodies having a mature heavy chain having an amino acid sequence of any of SEQ ID NOs:15-27 paired with a mature light chain having an amino acid sequence of any of SEQ ID NOs:28-30.

Although humanized antibodies often incorporate all six CDRs (defined by any conventional definition but preferably as defined by Kabat) from a mouse antibody, they can also be made with less than all CDRs (e.g., at least 3, 4, or 5 CDRs) from a mouse antibody (e.g., Pascalis et al., *J. Immunol.* 169:3076, 2002; Vajdos et al., *J. of Mol. Biol.,* 320: 415-428, 2002; Iwahashi et al., *Mol. Immunol.* 36:1079-1091, 1999; Tamura et al, *J. Immunol.,* 164:1432-1441, 2000).

In some antibodies only part of the CDRs, namely the subset of CDR residues required for binding, termed the SDRs, are needed to retain binding in a humanized antibody. CDR residues not contacting antigen and not in the SDRs can be identified based on previous studies (for example residues H60-H65 in CDR H2 are often not required), from regions of Kabat CDRs lying outside Chothia hypervariable loops (Chothia, *J. Mol. Biol.* 196:901, 1987), by molecular modeling and/or empirically, or as described in Gonzales et al., *Mol. Immunol.* 41: 863, 2004. In such humanized antibodies at positions in which one or more donor CDR residues is absent or in which an entire donor CDR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity and/or for meeting the WHO INN definition of "humanized". However, substitutions can also cause changes of affinity, and significant reductions in affinity are preferably avoided. Positions for substitution within CDRs and amino acids to substitute can also be selected empirically.

The human acceptor antibody sequences can optionally be selected from among the many known human antibody sequences to provide a high degree of sequence identity (e.g., 65-85% identity) between a human acceptor sequence variable region frameworks and corresponding variable region frameworks of a donor antibody chain.

An example of an acceptor sequence for the heavy chain is the human mature heavy chain variable region with NCBI accession code AAA18265.1 (SEQ ID NO:31). An example of an acceptor sequence for the heavy chain is the human mature heavy chain variable region with NCBI accession code ADW08092.1 (SEQ ID NO:32). An example of an acceptor sequence for the heavy chain is the human mature heavy chain variable region with NCBI accession code IMGT #IGHV1-2*02 (SEQ ID NO:33). IMGT #IGHV1-2*02 includes CDRs CDR-H1 and CDR-H2 having the same canonical form as mouse 16G7 heavy chain and is a member of Kabat human chain heavy subgroup 1. An example of an acceptor sequence for the light chain is the human mature light chain variable region with NCBI accession code AAB24404.1 (SEQ ID NO: 34). An example of an acceptor sequence for the light chain is the human mature light chain variable region with NCBI accession code AEK69364.1 (SEQ ID NO: 35). An example of an acceptor sequence for the light chain is the human mature light chain variable region with NCBI accession code IMGT#IGKV4-1*01 (SEQ ID NO: 36). IMGT#IGKV4-1*01 has the same canonical classes for CDR-L1, CDR-L2 and CDR-L3 as does mouse 16G7, and belongs to human kappa subgroup 1.

If more than one human acceptor antibody sequence is selected, a composite or hybrid of those acceptors can be used, and the amino acids used at different positions in the humanized light chain and heavy chain variable regions can be taken from any of the human acceptor antibody sequences used.

Certain amino acids from the human variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid can be substituted by the equivalent framework amino acid from the mouse antibody when it is reasonably expected that the amino acid:

(1) noncovalently binds antigen directly;
(2) is adjacent to a CDR region or within a CDR as defined by Chothia but not Kabat;
(3) otherwise interacts with a CDR region (e.g., is within about 6 Å of a CDR region), (e.g., identified by modeling the light or heavy chain on the solved structure of a homologous known immunoglobulin chain); or
(4) is a residue participating in the VL-VH interface.

The invention provides humanized forms of the murine 16G7 antibody including 13 exemplified humanized mature heavy chain variable regions: hu16G7VHv1 (SEQ ID NO:15), hu16G7VHv2 (SEQ ID NO:16), hu16G7VHv2a (SEQ ID NO:17), 16G7VHv2aB7 (SEQ ID NO:18), hu16G7VHv2b (SEQ ID NO:19), hu16G7VHv2bH7 (SEQ ID NO:20), hu16G7VHv3 (SEQ ID NO:21), hu16G7VHv4 (SEQ ID NO:22), hu16G7VHv5V (SEQ ID NO:23), hu16G7VHv5VR (SEQ ID NO:24), hu16G7VHv6a (SEQ ID NO:25), hu16G7VHv6b (SEQ ID NO:26 hu16G7VHv7 (SEQ ID NO:27). and 3 exemplified human mature light chain variable regions: hu16G7VLv1 (SEQ ID NO:28). hu16G7VLv2 (SEQ ID NO:29), and hu16G7VLv3 (SEQ ID NO:30).

In an embodiment, humanized sequences are generated using a two-stage PCR protocol that allows introduction of multiple mutations, deletions, and insertions using QuikChange site-directed mutagenesis [Wang, W. and Malcolm, B. A. (1999) BioTechniques 26:680-682)].

Framework residues from classes (1) through (3) as defined by Queen, U.S. Pat. No. 5,530,101, are sometimes alternately referred to as canonical and vernier residues. Framework residues that help define the conformation of a CDR loop are sometimes referred to as canonical residues (Chothia & Lesk, J. Mol. Biol. 196:901-917 (1987); Thornton & Martin, J. Mol. Biol. 263:800-815 (1996)). Framework residues that support antigen-binding loop conformations and play a role in fine-tuning the fit of an antibody to antigen are sometimes referred to as vernier residues (Foote & Winter, J. Mol. Biol 224:487-499 (1992)).

Other framework residues that are candidates for substitution are residues creating a potential glycosylation site. Still other candidates for substitution are acceptor human framework amino acids that are unusual for a human immunoglobulin at that position. These amino acids can be substituted with amino acids from the equivalent position of the mouse donor antibody or from the equivalent positions of more typical human immunoglobulins.

Other framework residues that are candidates for substitution are N-terminal glutamine residues (Q) that may be replaced with glutamic acid (E) to minimize potential for pyroglutamate conversion [Y. Diana Liu, et al., 2011, J. Biol. Chem., 286: 11211-11217]. Glutamic acid (E) conversion to pyroglutamate (pE) occurs more slowly than from glutamine (Q). Because of the loss of a primary amine in the glutamine to pE conversion, antibodies become more acidic. Incomplete conversion produces heterogeneity in the antibody that can be observed as multiple peaks using charge-based analytical methods. Heterogeneity differences may indicate a lack of process control. Exemplary humanized antibodies with N-terminal glutamine to glutamate substitutions are SEQ ID NO:15 (hu16G7VHv1), SEQ ID NO:16 (hu16G7VHv2), SEQ ID NO:17 (hu16G7VHv2a), SEQ ID NO:18 (16G7VHv2aB7), SEQ ID NO:19 (hu16G7VHv2b), SEQ ID NO:20 (hu16G7VHv2bH7), SEQ ID NO:21 (hu16G7VHv3), SEQ ID NO:22 (hu16G7VHv4), SEQ ID NO:23 (hu16G7VHv5V), SEQ ID NO:24 (hu16G7VHv5VR), and SEQ ID NO:27 (hu16G7VHv7).

Exemplary humanized antibodies are humanized forms of the mouse 16G7, designated Hu16G7.

The mouse antibody 16G7 comprises mature heavy and light chain variable regions having amino acid sequences comprising SEQ ID NO: 7 and SEQ ID NO:11, respectively. The invention provides 13 exemplified humanized mature heavy chain variable regions: hu16G7VHv1, hu16G7VHv2), hu16G7VHv2a, 16G7VHv2aB7, hu16G7VHv2b, hu16G7VHv2bH7, hu16G7VHv3, hu16G7VHv4, hu16G7VHv5V, hu16G7VHv5VR, hu16G7VHv6a, hu16G7VHv6b, and hu16G7VHv7. The invention further provides 3 exemplified human mature light chain variable regions: hu16G7VLv1. hu16G7VLv2, and hu16G7VLv3. FIGS. 2 and 3 show alignments of the heavy chain variable region and light chain variable region, respectively, of murine 16G7 and various humanized antibodies.

For reasons such as possible influence on CDR conformation and/or binding to antigen, mediating interaction between heavy and light chains, interaction with the constant region, being a site for desired or undesired posttranslational modification, being an unusual residue for its position in a human variable region sequence and therefore potentially immunogenic, getting aggregation potential, and other reasons, the following 33 variable region framework positions were considered as candidates for substitutions in the 3 exemplified human mature light chain variable regions and the 13 exemplified human mature heavy chain variable regions, as further specified in the examples: L4 (M4L), L9 (D9S), L15 (I15V), L18 (R18K), L19 (A19V), L21 (I21M), L22 (N22S), L43 (P43S), L48 (I48M), H1 (Q1E), H5 (V5Q), H7 (S7P), H9 (A9S), H10 (E10V), H11 (V11L), H12 (K12V), H13 (K13R), H20 (V20L), H37 (V37A), H38 (R38K), H40 (A40R), H48 (M48I), H66 (R66K), H67 (V67K), H69 (M69L), H71 (R71V), H73 (T73I), H75 (I75S or I75A), H80 (M80V), H82a (S82a-T), H82b (R82b-S), H83 (R83T), H85 (D85E). The following 3 variable region CDR positions were considered as candidates for substitutions in the 13 exemplified human mature heavy chain variable regions, as further specified in the examples: H31 (S31G), H60 (N60A), and H64 (K64Q).

Here, as elsewhere, the first-mentioned residue is the residue of a humanized antibody formed by grafting Kabat CDRs or a composite Chothia-Kabat CDR in the case of CDR-H1 into a human acceptor framework, and the second-mentioned residue is a residue being considered for replacing such residue. Thus, within variable region frameworks, the first mentioned residue is human, and within CDRs, the first mentioned residue is mouse.

Exemplified antibodies include any permutations or combinations of the exemplified mature heavy and light chain variable regions e.g., VHv1/VLv1, VHv1/VLv2, VHv1/VLv3, VHv2/VLv1, VHv2/VLv2, VHv2/VLv3, VHv2a/VLv1, VHv2a/VLv2, VHv2a/VLv3, VHv2aB7/VLv1, VHv2aB7/VLv2, VHv2aB7/VLv3, VHv2b/VLv1, VHv2b/VLv2, VHv2b/VLv3, VHv2bH7/VLv1, VHv2bH7/VLv2, VHv2bH7/VLv3, VHv3/VLv1, VHv3/VLv2, VHv3/VLv3, VHv4/VLv1, VHv4/VLv2, VHv4/VLv3, VHv5/VLv1, VHv5/VLv2, VHv5/VLv3, VHv5VR/VLv1, VHv5VR/VLv2, VHv5VR/VLv3, VHv6a/VLv1, VHv6a/VLv2, VHv6a/VLv3, VHv6b/VLv1, VHv6b/VLv2, VHv6b/VLv3, VHv7/VLv1, VHv7/VLv2, or VHv7/VLv3.

The invention provides variants of the 16G7 humanized antibody in which the humanized mature heavy chain variable region shows at least 90%, 95%, 96%, 97%, 98%, or 99% identity to hu16G7VHv1, hu16G7VHv2, hu16G7VHv2a, 16G7VHv2aB7, hu16G7VHv2b, hu16G7VHv2bH7, hu16G7VHv3, hu16G7VHv4, hu16G7VHv5V, hu16G7VHv5VR, hu16G7VHv6a, hu16G7VHv6b, and hu16G7VHv7 (SEQ ID NOs: 15-27) and the humanized mature light chain variable region shows at least 90%, 95%, 96%, 97%, 98%, or 99% identity to hu16G7VLv1. hu16G7VLv2, and hu16G7VLv3 (SEQ ID NO: 28-30). In some such antibodies at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or all 36 of the backmutations or other mutations found in SEQ ID NO:15-27 and SEQ ID NO:28-30 are retained.

In some humanized 16G7 antibodies, at least one of the following positions in the VH region is occupied by the amino acid as specified: H1 is occupied by E, H5 is occupied by Q, H7 is occupied by P, H9 is occupied by S, H10 is occupied by V, H11 is occupied L, H12 is occupied by V, H13 is occupied by R, H20 is occupied by L, H40 is occupied by R, H48 is occupied by I, H66 is occupied by K, H67 is occupied by A, H69 is occupied by L, H71 is occupied by V, H73 is occupied by I, H75 is occupied by S, H80 is occupied by V, H82a is occupied by T, H82b is occupied by S, H83 is occupied by T, and H85 is occupied by E. In some humanized 16G7 antibodies, positions H1, H5, H7, H9, H10, H11, H12, H13, H20, H40, H48, H66, H67, H69, H71, H73, H75, H80, H82a, H82b, H83, and H85 in the VH region are occupied by, E, Q, P, S, V, L, V, R, L, R, I, K, A, L, V, I, S, V, T, S, T, and E, respectively.

In some humanized 16G7 antibodies, at least one of the following positions in the VH region is occupied by the amino acid as specified: H1 is occupied by E, H5 is occupied by Q, H7 is occupied by P, H9 is occupied by S, H10 is occupied by V, H11 is occupied by L, H12 is occupied by V, H13 is occupied by R, H20 is occupied by L, H48 is occupied by I, H69 is occupied by L, H71 is occupied by V, H82a is occupied by T, H82b is occupied by S, H83 is occupied by T, and H85 is occupied by E. In some humanized 16G7 antibodies, positions H1, H5, H7, H9, H10, H11, H12, H13, H20, H48, H69, H71, H82a, H82b, H83, and H85 in the VH region are occupied by E, Q, P, S, V, L, V, R, L, I, L, V, T, S, T, and E, respectively.

In some humanized 16G7 antibodies, at least one of the following positions in the VH region is occupied by the amino acid as specified: H1 is occupied by E, H5 is occupied by Q, H11 is occupied by L, H12 is occupied by V, H20 is occupied by L, H48 is occupied by I, H69 is occupied by L, H71 is occupied by V, H82a is occupied by T, H82b is occupied by S, H83 is occupied by T, and H85 is occupied by E. In some humanized 16G7 antibodies, positions H1, H5, H11, H12, H20, H48, H69, H71, H82a, H82b, H83, and H85. in the VH region are occupied by E, Q, L, V, L I, L, V, T, S, T, and E, respectively.

In some humanized 16G7 antibodies, at least one of the following positions in the VH region is occupied by the amino acid as specified: H1 is occupied by E, H12 is occupied by V, H31 is occupied by G, H40 is occupied by R, H48 is occupied by I, H60 is occupied by A, H69 is occupied by L, H73 is occupied by I, and H83 is occupied by T. In some humanized 16G7 antibodies, positions H1, H12, H31, H40, H48, H60, H69, H73, and H83 in the VH region are occupied by are occupied by E, V, G, R, I, A, L, I, and T, respectively.

In some humanized 16G7 antibodies, at least one of the following positions in the VH region is occupied by the amino acid as specified: H1 is occupied by E, H12 is occupied by V, H40 is occupied by R, H48 is occupied by I, H69 is occupied by L, H73 is occupied by I, and H83 is occupied by T. In some humanized 16G7 antibodies, positions H1, H12, H40, H48, H69, H73, and H83 in the VH region are occupied by are occupied by E, V, R, I, L, I, and T, respectively.

In some humanized 16G7 antibodies, at least one of the following positions in the VH region is occupied by the amino acid as specified: H1 is occupied by E, H12 is occupied by V, H40 is occupied by R, H48 is occupied by I, H66 is occupied K, H67 is occupied by A, H69 is occupied by L, H71 is occupied by V, H73 is occupied by I, and H83 is occupied by T. In some humanized 16G7 antibodies, positions H1, H12, H40, H48, H66, H67, H69, H71, H73, and H83 in the VH region are occupied by are occupied by E, V, R, I, K, A, L, V, I, and T, respectively.

In some humanized 16G7 antibodies, at least one of the following positions in the VH region is occupied by the amino acid as specified: H1 is occupied by E, H12 is occupied by V, H40 is occupied by R, H48 is occupied by I, H69 is occupied by L, H73 is occupied by I, and H83 is occupied by T. In some humanized 16G7 antibodies, positions H1, H12, H40, H48, H69, H73, and H83 in the VH region are occupied by are occupied by E, V, R, I, L, I, and T, respectively.

In some humanized 16G7 antibodies, at least one of the following positions in the VH region is occupied by the amino acid as specified: H7 is occupied by P, H71 is occupied by V, and H73 is occupied by I. In some humanized 16G7 antibodies, positions H7, H71, and H73 in the VH region are occupied by are occupied by P, V, and I, respectively.

In some humanized 16G7 antibodies, at least one of the following positions in the VH region is occupied by the amino acid as specified: H31 is occupied by G and H60 is occupied by A. In some humanized 16G7 antibodies, positions H31 and H60 in the VH region are occupied by G and A, respectively.

In some humanized 16G7 antibodies, positions H1, H12, H31, H40, H48, H60, H66, H67, H69, H71, H73, and H83 in the VH region are occupied by Q, V, G, R, I, A, K, A, L, V, I, and T, respectively.

In some humanized 16G7 antibodies, positions H1, H7, H71, and H73 in the VH region are occupied by Q, P, V and I, respectively.

In some humanized 16G7 antibodies, at least one of the following positions in the VH region is occupied by the amino acid as specified: H1 is occupied by Q or E, H5 is occupied by V or Q, H7 is occupied by S or P, H9 is occupied by A or S, H10 is occupied by E or V, H11 is occupied V or L, H12 is occupied by K or V, H13 is occupied by K or R, H20 is occupied by V or L, H31 is occupied by G or S, H37 is occupied by V or A, H 38 is occupied by R or K, H40 is occupied by A or R, H48 is occupied by M or I, H60 is occupied by A or N, H64 is occupied by Q or K, H66 is occupied by R or K, H67 is occupied by V or A, H69 is occupied by M or L, H71 is occupied by R or V, H73 is occupied by T or I, H75 is occupied by I, S, or A, H80 is occupied by M or V, H82a is occupied by S or T, H82b is occupied by R or S, H83 is occupied by R or T, and H85 is occupied by D or E.

In some humanized 16G7 antibodies, positions H1, H5, H7, H9, H10, H11, H12, H13, H20, H37, H38, H40, H48, H66, H67, H69, H71, H73, H75, H80, H82a, H82b, H83, and H85 in the VH region are occupied by E, Q, P, S, V, L, V, R, L, A, K, R, I, K, A, L, V, I, S, V, T, S, T, and E, respectively, as in hu16G7VHv1. In some humanized 16G7 antibodies, positions H1, H5, H11, H12, H20, H48, H69, H71, H75, H82a, H82b, H83, and H85 in the VH region are occupied by E, Q, L, V, L, I, L, V, A, T, S, T, and E, respectively, as in hu16G7VHv2. In some humanized 16G7 antibodies, positions H1, H12, H40, H48, H66, H67, H69, H71, H73, and H83 in the VH region are occupied by E, V, R, I, K, A, L, V, I, and T, respectively, as in hu16G7VHv2a. In some humanized 16G7 antibodies, positions H1, H12, H31, H40, H48, H60, H66, H67, H69, H71, H73, and H83 in the VH region are occupied by E, V, G, R, I, A, K, A, L, V, I, and T, respectively, as in hu16G7VHv2aB7. In some humanized 16G7 antibodies, positions H1, H12, H40, H48, H69, H73, and H83 in the VH region are occupied by E, V, R, I, L, I, and T, respectively, as in hu16G7VHv2b. In some humanized 16G7 antibodies, positions H1, H12, H31, H40, H48, H60, H64, H69, H73, and H83 in the VH region are occupied by, E, V, G, R, I, A, Q, L, I, and T, respectively, as in hu16G7VHv2bH7. In some humanized 16G7 antibodies, positions H1, H5, H7, H9, H10, H11, H12, H13, H20, H48, H69, H71, H75, H82a, H82b, H83, and H85 in the VH region are occupied by E, Q, P, S, V, L, V, R, L, I, L, V, A, T, S, T, and E, respectively, as in hu16G7VHv3. In some humanized 16G7 antibodies, positions H1, H5, H11, H12, H20, H48, H66, H67, H69, H71, H73, H75, H82a, H82b, H83, and H85 in the VH region are occupied by, E, Q, L, V, L, I, K, A, L, V, I, S, T, S, T, and E, respectively, as in hu16G7VHv4. In some humanized 16G7 antibodies, positions H1, H5, H7, H9, H10, H11, H12, H13, H20, H38, H40, H48, H66, H67, H69, H71, H73I, H75, H80, H82a, H82b, H83, and H85 in the VH region are occupied by E, Q, P, S, V, L, V, R, L, K, R, I, K, A, L, V, I, S, V, T, S, T, and E, respectively, as in hu16G7VHv5V. In some humanized 16G7 antibodies, positions H1, H5, H7, H9, H10, H11, H12, H13, H20, H40, H48, H66, H67, H69, H71, H73, H75, H80, H82a, H82b, H83, and H85 in the VH region are occupied by Q, P, S, V, L, V, R, L, R, I, K, A, L, V, I, S, V, T, S, T, and E, respectively, as in hu16G7VHv5VR. In some humanized 16G7 antibodies, positions H7, H71, and H73 in the VH region are occupied by P, V, and I, respectively, as in hu16G7VHv6a. In some humanized 16G7 antibodies, position H71 in the VH region is occupied by V, as in hu16G7VHv6b. In some humanized 16G7 antibodies, positions H1, H7, H71, and H73 in the VH region are occupied by E, P, V, and I, respectively, as in hu16G7VHv7.

In some humanized 16G7 antibodies, the variable heavy chain has ≥85% identity to human sequence. In some humanized 16G7 antibodies, the variable light chain has ≥85% identity to human sequence. In some humanized 16G7 antibodies, each of the variable heavy chain and variable light chain has ≥85% identity to human germline sequence.

In some humanized 16G7 antibodies, the three heavy chain CDRs are as defined by Kabat/Chothia Composite (SEQ ID NOs: 8, 9, and 10) and the three light chain CDRs are as defined by Kabat/Chothia Composite (SEQ ID NOs: 12, 13, and 14); provided that position H31 is occupied by S or G, position H60 is occupied by N or A and position 64 is occupied by K or Q. In some humanized 16G7 antibodies, CDR-H1 has an amino acid sequence comprising SEQ ID NO: 49. In some humanized 16G7 antibodies, CDR-H2 has an amino acid sequence comprising SEQ ID NO: 50. In some humanized 16G7 antibodies, CDR-H2 has an amino acid sequence comprising SEQ ID NO: 51.

In some humanized 16G7 antibodies, at least one of the following positions in the VH region is occupied by the amino acid as specified: L4 is occupied by L, L9 is occupied by S, L15 is occupied by V, L22 is occupied by S, and L43 is occupied by S. In some humanized 16G7 antibodies, positions L4, L9, L15, L22, and L43 in the VL region are occupied by L, S, V, S, and S, respectively.

In some humanized 16G7 antibodies, at least one of the following positions in the VH region is occupied by the amino acid as specified: L4 is occupied by L, L9 is occupied by S, L15 is occupied by V, L18 is occupied by K, L19 is occupied by V, L21 is occupied by M, L22 is occupied by S, and L43 is occupied by S. In some humanized 16G7 antibodies, positions L4, L9, L15, L18, L19, L21, L22, and L43 in the VL region are occupied by L, S, V, K, V, M, S, and S, respectively.

In some humanized 16G7 antibodies, at least one of the following positions in the VL region is occupied by the amino acid as specified: L4 is occupied by M or L, L9 is occupied by D or S, L15 is occupied by L or V, L18 is occupied by R or K, L19 is occupied by A or V, L21 is occupied by I or M, L22 is occupied by N or S, L43 is occupied by P or S, and L48 is occupied by I or M.

In some humanized 16G7 antibodies, positions L4, L9, L15, L18, L19, L21, L22, and L43 in the VL region are occupied by L, S, V, K, V, M, S, and S, respectively, as in hu16G7VLv1. In some humanized 16G7 antibodies, positions L4, L9, L15, L22, and L43 in the VL region are occupied by L, S, V, S, and S, respectively, as in hu16G7VLv2. In some humanized 16G7 antibodies, positions L4, L9, L15, L18, L19, L21, L22, and L43 in the VL region are occupied by L, S, V, K, V, M, S, and S, respectively, as in hu16G7VLv3.

In some humanized 16G7 antibodies, the variable heavy chain has 85% identity to human sequence. In some humanized 16G7 antibodies, the variable light chain has 85% identity to human sequence. In some humanized 16G7 antibodies, each of the variable heavy chain and variable light chain has 85% identity to human germline sequence. In some humanized 16G7 antibodies, the three heavy chain CDRs are as defined by Kabat/Chothia Composite (SEQ ID NOs: 8, 9, and 10) and the three light chain CDRs are as defined by Kabat/Chothia Composite (SEQ ID NOs: 12, 13, and 14); provided that position H31 is occupied by S or G, position H60 is occupied by N or A and position 64 is occupied by K or Q. In some humanized 16G7 antibodies, CDR-H1 has an amino acid sequence comprising SEQ ID NO: 49. In some humanized 16G7 antibodies, CDR-H2 has an amino acid sequence comprising SEQ ID NO: 50. In some humanized 16G7 antibodies, CDR-H2 has an amino acid sequence comprising SEQ ID NO: 51.

The CDR regions of such humanized antibodies can be identical or substantially identical to the CDR regions of 16G7. The CDR regions can be defined by any conventional definition (e.g., Chothia, or composite of Chothia and Kabat) but are preferably as defined by Kabat.

Variable regions framework positions are in accordance with Kabat numbering unless otherwise stated. Other such variants typically differ from the sequences of the exemplified Hu16G7 heavy and light chains by a small number (e.g., typically no more than 1, 2, 3, 5, 10, or 15) of replacements, deletions or insertions. Such differences are usually in the framework but can also occur in the CDRs.

A possibility for additional variation in humanized 16G7 variants is additional backmutations in the variable region frameworks. Many of the framework residues not in contact with the CDRs in the humanized mAb can accommodate substitutions of amino acids from the corresponding positions of the donor mouse mAb or other mouse or human antibodies, and even many potential CDR-contact residues are also amenable to substitution. Even amino acids within the CDRs may be altered, for example, with residues found at the corresponding position of the human acceptor sequence used to supply variable region frameworks. In addition, alternate human acceptor sequences can be used, for example, for the heavy and/or light chain. If different acceptor sequences are used, one or more of the backmutations recommended above may not be performed because the corresponding donor and acceptor residues are already the same without backmutations.

Preferably, replacements or backmutations in humanized 16G7 variants (whether or not conservative) have no substantial effect on the binding affinity or potency of the humanized mAb, that is, its ability to bind to tau).

The humanized 16G7 antibodies are further characterized by their ability to bind both phosphorylated and unphosphorylated tau and misfolded/aggregated forms of tau.

D. Chimeric and Veneered Antibodies

The invention further provides chimeric and veneered forms of non-human antibodies, particularly the 16G7 antibodies of the examples.

A chimeric antibody is an antibody in which the mature variable regions of light and heavy chains of a non-human antibody (e.g., a mouse) are combined with human light and heavy chain constant regions. Such antibodies substantially or entirely retain the binding specificity of the mouse antibody, and are about two-thirds human sequence. In an embodiment, a chimeric 16G7 antibody has a heavy chain amino acid sequence of SEQ ID NO: 54 and a light chain amino acid sequence of SEQ ID NO:55.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, Mol. Immunol. 28:489, 1991) with residues from the corresponding positions of a human antibody sequence. The result is an antibody in which the CDRs are entirely or substantially from a non-human antibody and the variable region frameworks of the non-human antibody are made more human-like by the substitutions. Veneered forms of the 16G7 antibody are included in the invention.

E. Human Antibodies

Human antibodies against tau or a fragment thereof (e.g., amino acid residues 55-78, 60-75, 61-70, 55-69, or 64-78 of SEQ ID NO: 3, corresponding to amino acid residues 113-136, 118-133, 119-128, 113-127, or 122-136, respectively, of SEQ ID NO:1) are provided by a variety of techniques described below. Some human antibodies are selected by competitive binding experiments, by the phage display method of Winter, above, or otherwise, to have the same epitope specificity as a particular mouse antibody, such as one of the mouse monoclonal antibodies described in the examples. Human antibodies can also be screened for a particular epitope specificity by using only a fragment of tau, such as a tau fragment containing only, amino acid residues 55-78, 60-75, 61-70, 55-69, or 64-78 of SEQ ID NO: 3 (corresponding to amino acid residues 113-136, 118-133, 119-128, 113-127, or 122-136, respectively, of SEQ ID NO:1), as the target antigen, and/or by screening antibodies against a collection of tau variants, such as tau variants containing various mutations within amino acid residues 55-78, 60-75, 61-70, 55-69, or 64-78 of SEQ ID NO: 3 (corresponding to amino acid residues 113-136, 118-133, 119-128, 113-127, or 122-136, respectively, of SEQ ID NO:1).

Methods for producing human antibodies include the trioma method of Oestberg et al., Hybridoma 2:361-367 (1983); Oestberg, U.S. Pat. No. 4,634,664; and Engleman et al., U.S. Pat. No. 4,634,666, use of transgenic mice including human immunoglobulin genes (see, e.g., Lonberg et al., WO93/12227 (1993); U.S. Pat. Nos. 5,877,397; 5,874,299; 5,814,318; 5,789,650; 5,770,429; 5,661,016; 5,633,425; 5,625,126; 5,569,825; 5,545,806; Neuberger, Nat. Biotechnol. 14:826 (1996); and Kucherlapati, WO 91/10741 (1991)) phage display methods (see, e.g., Dower et al., WO 91/17271; McCafferty et al., WO 92/01047; U.S. Pat. Nos. 5,877,218; 5,871,907; 5,858,657; 5,837,242; 5,733,743; and 5,565,332); and methods described in WO 2008/081008 (e.g., immortalizing memory B cells isolated from humans, e.g., with EBV, screening for desired properties, and cloning and expressing recombinant forms).

F. Selection of Constant Region

The heavy and light chain variable regions of chimeric, veneered or humanized antibodies can be linked to at least a portion of a human constant region. The choice of constant region depends, in part, whether antibody-dependent cell-mediated cytotoxicity, antibody dependent cellular phagocytosis and/or complement dependent cytotoxicity are desired. For example, human isotypes IgG1 and IgG3 have complement-dependent cytotoxicity and human isotypes IgG2 and IgG4 do not. Human IgG1 and IgG3 also induce stronger cell mediated effector functions than human IgG2 and IgG4. Light chain constant regions can be lambda or kappa. Numbering conventions for constant regions include EU numbering (Edelman, G. M. et al., Proc. Natl. Acad. USA, 63, 78-85 (1969)), Kabat numbering (Kabat, *Sequences of Proteins of Immunological Interest* (National Institutes of Health, Bethesda, Md., 1991, IMGT unique numbering (Lefranc M.-P. et al., IMGT unique numbering for immunoglobulin and T cell receptor constant domains and Ig superfamily C-like domains, Dev. Comp. Immunol., 29, 185-203 (2005), and IMGT exon numbering (Lefranc, supra).

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., *Proc. Natl. Acad. Sci. USA* 103:4005, 2006), or to prolong half-life in humans (see, e.g., Hinton et al., *J. Biol. Chem.* 279:6213, 2004). Exemplary substitutions include a Gln at position 250 and/or a Leu at position 428 (EU numbering is used in this paragraph for the constant region) for increasing the half-life of an antibody. Substitution at any or all of positions 234, 235, 236 and/or 237 reduce affinity for Fcγ receptors, particularly FcγRI receptor (see, e.g., U.S. Pat. No. 6,624,821). An alanine substitution at positions 234, 235, and 237 of human IgG1 can be used for reducing effector functions. Some antibodies have alanine substitution at positions 234, 235 and 237 of human IgG1 for reducing effector functions. Optionally, positions 234, 236 and/or 237 in human IgG2 are substituted with alanine and position 235 with glutamine (see, e.g., U.S. Pat. No. 5,624, 821). In some antibodies, a mutation at one or more of positions 241, 264, 265, 270, 296, 297, 322, 329, and 331 by EU numbering of human IgG1 is used. In some antibodies, a mutation at one or more of positions 318, 320, and 322 by EU numbering of human IgG1 is used. In some antibodies, positions 234 and/or 235 are substituted with alanine and/or position 329 is substituted with glycine. In some antibodies, positions 234 and 235 are substituted with alanine. In some antibodies, the isotype is human IgG2 or IgG4.

Antibodies can be expressed as tetramers containing two light and two heavy chains, as separate heavy chains, light chains, as Fab, Fab', F(ab')2, and Fv, or as single chain antibodies in which heavy and light chain mature variable domains are linked through a spacer.

Human constant regions show allotypic variation and isoallotypic variation between different individuals, that is, the constant regions can differ in different individuals at one or more polymorphic positions. Isoallotypes differ from allotypes in that sera recognizing an isoallotype bind to a non-polymorphic region of a one or more other isotypes. Thus, for example, another heavy chain constant region is of IgG1 G1m3 with or without the C-terminal lysine. Reference to a human constant region includes a constant region with any natural allotype or any permutation of residues occupying positions in natural allotypes.

G. Expression of Recombinant Antibodies

A number of methods are known for producing chimeric and humanized antibodies using an antibody-expressing cell line (e.g., hybridoma). For example, the immunoglobulin variable regions of antibodies can be cloned and sequenced using well known methods. In one method, the heavy chain variable VH region is cloned by RT-PCR using mRNA prepared from hybridoma cells. Consensus primers are employed to the VH region leader peptide encompassing the translation initiation codon as the 5' primer and a g2b constant regions specific 3' primer. Exemplary primers are described in U.S. patent publication US 2005/0009150 by Schenk et al. (hereinafter "Schenk"). The sequences from multiple, independently derived clones can be compared to ensure no changes are introduced during amplification. The sequence of the VH region can also be determined or confirmed by sequencing a VH fragment obtained by 5' RACE RT-PCR methodology and the 3' g2b specific primer.

The light chain variable VL region can be cloned in an analogous manner. In one approach, a consensus primer set is designed for amplification of VL regions using a 5' primer designed to hybridize to the VL region encompassing the translation initiation codon and a 3' primer specific for the Ck region downstream of the V-J joining region. In a second approach, 5'RACE RT-PCR methodology is employed to clone a VL encoding cDNA. Exemplary primers are described in Schenk, supra. The cloned sequences are then combined with sequences encoding human (or other non-human species) constant regions.

In one approach, the heavy and light chain variable regions are re-engineered to encode splice donor sequences downstream of the respective VDJ or VJ junctions and are cloned into a mammalian expression vector, such as pCMV-hγ1 for the heavy chain and pCMV-Mcl for the light chain. These vectors encode human γ1 and Ck constant regions as exonic fragments downstream of the inserted variable region cassette. Following sequence verification, the heavy chain and light chain expression vectors can be co-transfected into CHO cells to produce chimeric antibodies. Conditioned media is collected 48 hours post-transfection and assayed by western blot analysis for antibody production or ELISA for antigen binding. The chimeric antibodies are humanized as described above.

Chimeric, veneered, humanized, and human antibodies are typically produced by recombinant expression. Recombinant polynucleotide constructs typically include an expression control sequence operably linked to the coding sequences of antibody chains, including naturally associated or heterologous expression control elements, such as a promoter. The expression control sequences can be promoter systems in vectors capable of transforming or transfecting eukaryotic or prokaryotic host cells. Once the vector has been incorporated into the appropriate host, the host is maintained under conditions suitable for high level expression of the nucleotide sequences and the collection and purification of the crossreacting antibodies.

These expression vectors are typically replicable in the host organisms either as episomes or as an integral part of the host chromosomal DNA. Commonly, expression vectors contain selection markers, e.g., ampicillin resistance or hygromycin resistance, to permit detection of those cells transformed with the desired DNA sequences.

*E. coli* is one prokaryotic host useful for expressing antibodies, particularly antibody fragments. Microbes, such as yeast, are also useful for expression. *Saccharomyces* is a yeast host with suitable vectors having expression control sequences, an origin of replication, termination sequences, and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

Mammalian cells can be used for expressing nucleotide segments encoding immunoglobulins or fragments thereof. See Winnacker, From Genes to Clones, (VCH Publishers, N Y, 1987). A number of suitable host cell lines capable of secreting intact heterologous proteins have been developed, and include CHO cell lines, various COS cell lines, HeLa cells, HEK293 cells, L cells, and non-antibody-producing myelomas including Sp2/0 and NSO. The cells can be nonhuman. Expression vectors for these cells can include expression control sequences, such as an origin of replication, a promoter, an enhancer (Queen et al., *Immunol. Rev.* 89:49 (1986)), and necessary processing information sites, such as ribosome binding sites, RNA splice sites, polyadenylation sites, and transcriptional terminator sequences. Expression control sequences can include promoters derived from endogenous genes, cytomegalovirus, SV40, adenovirus, bovine papillomavirus, and the like. See Co et al., *J. Immunol.* 148:1149 (1992).

Alternatively, antibody coding sequences can be incorporated in transgenes for introduction into the genome of a transgenic animal and subsequent expression in the milk of the transgenic animal (see, e.g., U.S. Pat. Nos. 5,741,957; 5,304,489; and 5,849,992). Suitable transgenes include coding sequences for light and/or heavy chains operably linked with a promoter and enhancer from a mammary gland specific gene, such as casein or beta lactoglobulin.

The vectors containing the DNA segments of interest can be transferred into the host cell by methods depending on the type of cellular host. For example, calcium chloride transfection is commonly utilized for prokaryotic cells, whereas calcium phosphate treatment, electroporation, lipofection, biolistics, or viral-based transfection can be used for other cellular hosts. Other methods used to transform mammalian cells include the use of polybrene, protoplast fusion, liposomes, electroporation, and microinjection. For production of transgenic animals, transgenes can be microinjected into fertilized oocytes or can be incorporated into the genome of embryonic stem cells, and the nuclei of such cells transferred into enucleated oocytes.

Having introduced vector(s) encoding antibody heavy and light chains into cell culture, cell pools can be screened for growth productivity and product quality in serum-free media. Top-producing cell pools can then be subjected of FACS-based single-cell cloning to generate monoclonal lines. Specific productivities above 50 pg or 100 pg per cell per day, which correspond to product titers of greater than 7.5 g/L culture, can be used. Antibodies produced by single cell clones can also be tested for turbidity, filtration properties, PAGE, IEF, UV scan, HP-SEC, carbohydrate-oligosaccharide mapping, mass spectrometry, and binding assay, such as ELISA or Biacore. A selected clone can then be banked in multiple vials and stored frozen for subsequent use.

Once expressed, antibodies can be purified according to standard procedures of the art, including protein A capture, HPLC purification, column chromatography, gel electrophoresis and the like (see generally, Scopes, *Protein Purification* (Springer-Verlag, NY, 1982)).

Methodology for commercial production of antibodies can be employed, including codon optimization, selection of promoters, selection of transcription elements, selection of terminators, serum-free single cell cloning, cell banking, use of selection markers for amplification of copy number, CHO terminator, or improvement of protein titers (see, e.g., U.S. Pat. Nos. 5,786,464; 6,114,148; 6,063,598; 7,569,339; WO2004/050884; WO2008/012142; WO2008/012142; WO2005/019442; WO2008/107388; WO2009/027471; and U.S. Pat. No. 5,888,809).

IV. Active Immunogens

An agent used for active immunization serves to induce in a patient the same types of antibody described in connection with passive immunization above. Agents used for active immunization can be the same types of immunogens used for generating monoclonal antibodies in laboratory animals, e.g., a peptide of 3-15 or 3-12 or 5-12, or 5-8 contiguous amino acids from a region of tau corresponding to residues 55-78, 60-75, 61-70, 55-69, or 64-78 of SEQ ID NO: 3 (corresponding to amino acid residues 113-136, 118-133, 119-128, 113-127, or 122-136, respectively, of SEQ ID NO:1), such as, for example, a peptide including residues 55-78, 60-75, 61-70, 55-69, or 64-78 of SEQ ID NO: 3 (corresponding to amino acid residues 113-136, 118-133, 119-128, 113-127, or 122-136, respectively, of SEQ ID NO:1). For inducing antibodies binding to the same or overlapping epitope as 16G7, the epitope specificity of these antibodies can be mapped (e.g., by testing binding to a series of overlapping peptides spanning tau). A fragment of tau consisting of or including or overlapping the epitope can then be used as an immunogen. Such fragments are typically used in unphosphorylated form.

The heterologous carrier and adjuvant, if used may be the same as used for generating monoclonal antibody, but may also be selected for better pharmaceutical suitability for use in humans. Suitable carriers include serum albumins, keyhole limpet hemocyanin, immunoglobulin molecules, thyroglobulin, ovalbumin, tetanus toxoid, or a toxoid from other pathogenic bacteria, such as diphtheria (e.g., CRM197), *E. coli*, cholera, or *H. pylori*, or an attenuated toxin derivative. T cell epitopes are also suitable carrier molecules. Some conjugates can be formed by linking agents of the invention to an immunostimulatory polymer molecule (e.g., tripalmitoyl-S-glycerine cysteine (Pam$_3$Cys), mannan (a mannose polymer), or glucan (a β 1→2 polymer)), cytokines (e.g., IL-1, IL-1 alpha and β peptides, IL-2, γ-INF, IL-10, GM-CSF), and chemokines (e.g., MIP1-α and β, and RANTES) Immunogens may be linked to the carriers with or without spacers amino acids (e.g., gly-gly). Additional carriers include virus-like particles. Virus-like particles (VLPs), also called pseudovirions or virus-derived particles, represent subunit structures composed of multiple copies of a viral capsid and/or envelope protein capable of self-assembly into VLPs of defined spherical symmetry in vivo. (Powilleit, et al., (2007) PLoS ONE 2(5):e415.) Alternatively, peptide immunogens can be linked to at least one artificial T-cell epitope capable of binding a large proportion of MHC Class II molecules, such as the pan DR epitope ("PADRE"). PADRE is described in U.S. Pat. No. 5,736,142, WO 95/07707, and Alexander J et al, Immunity, 1:751-761 (1994). Active immunogens can be presented in multimeric form in which multiple copies of an immunogen and/or its carrier are presented as a single covalent molecule.

Fragments are often administered with pharmaceutically acceptable adjuvants. The adjuvant increases the titer of induced antibodies and/or the binding affinity of induced antibodies relative to the situation if the peptide were used alone. A variety of adjuvants can be used in combination with an immunogenic fragment of tau to elicit an immune response. Preferred adjuvants augment the intrinsic response to an immunogen without causing conformational changes in the immunogen that affect the qualitative form of the response. Preferred adjuvants include aluminum salts, such as aluminum hydroxide and aluminum phosphate, 3 De-O-acylated monophosphoryl lipid A (MPL™) (see GB 2220211 (RIBI ImmunoChem Research Inc., Hamilton, Mont., now part of Corixa). Stimulon™ QS-21 is a triterpene glycoside or saponin isolated from the bark of the Quillaja Saponaria Molina tree found in South America (see Kensil et al., in *Vaccine Design: The Subunit and Adjuvant Approach* (eds. Powell & Newman, Plenum Press, N Y, 1995); U.S. Pat. No. 5,057,540), (Aquila BioPharmaceuticals, Framingham, Mass.; now Antigenics, Inc., New York, N.Y.). Other adjuvants are oil in water emulsions (such as squalene or peanut oil), optionally in combination with immune stimulants, such as monophosphoryl lipid A (see Stoute et al., *N. Engl. J. Med.* 336, 86-91 (1997)), pluronic polymers, and killed mycobacteria. Ribi adjuvants are oil-in-water emulsions. Ribi contains a metabolizable oil (squalene) emulsified with saline containing Tween 80. Ribi also contains refined mycobacterial products which act as immunostimulants and bacterial monophosphoryl lipid A. Another adjuvant is CpG (WO 98/40100). Adjuvants can be administered as a component of a therapeutic composition with an active agent or can be administered separately, before, concurrently with, or after administration of the therapeutic agent.

Analogs of natural fragments of tau that induce antibodies against tau can also be used. For example, one or more or all L-amino acids can be substituted with D amino acids in such peptides. Also the order of amino acids can be reversed (retro peptide). Optionally a peptide includes all D-amino acids in reverse order (retro-inverso peptide). Peptides and other compounds that do not necessarily have a significant amino acid sequence similarity with tau peptides but nevertheless serve as mimetics of tau peptides and induce a similar immune response, Anti-idiotypic antibodies against monoclonal antibodies to tau as described above can also be used. Such anti-Id antibodies mimic the antigen and generate an immune response to it (see Essential immunology, Roit ed Blackwell Scientific Publications, Palo Alto, Calif. 6th ed., p. 181).

Peptides (and optionally a carrier fused to the peptide) can also be administered in the form of a nucleic acid encoding the peptide and expressed in situ in a patient. A nucleic acid segment encoding an immunogen is typically linked to regulatory elements, such as a promoter and enhancer that allow expression of the DNA segment in the intended target cells of a patient. For expression in blood cells, as is desirable for induction of an immune response, promoter and enhancer elements from light or heavy chain immunoglobulin genes or the CMV major intermediate early promoter and enhancer are suitable to direct expression. The linked regulatory elements and coding sequences are often cloned into a vector. Antibodies can also be administered in the form of nucleic acids encoding the antibody heavy and/or light chains. If both heavy and light chains are present, the chains are preferably linked as a single chain antibody. Antibodies for passive administration can also be prepared e.g., by affinity chromatography from sera of patients treated with peptide immunogens.

The DNA can be delivered in naked form (i.e., without colloidal or encapsulating materials). Alternatively a number of viral vector systems can be used including retroviral systems (see, e.g., Lawrie and Tumin, Cur. Opin. Genet. Develop. 3, 102-109 (1993)); adenoviral vectors {see, e.g., Bett et al, J. Virol. 67, 591 1 (1993)); adeno-associated virus vectors {see, e.g., Zhou et al., J. Exp. Med. 179, 1867 (1994)), viral vectors from the pox family including vaccinia virus and the avian pox viruses, viral vectors from the alpha virus genus such as those derived from Sindbis and Semliki Forest Viruses (see, e.g., Dubensky et al., J. Virol. 70, 508-519 (1996)), Venezuelan equine encephalitis virus (see U.S. Pat. No. 5,643,576) and rhabdoviruses, such as vesicular stomatitis virus (see WO 96/34625) and papillomaviruses (Ohe et al., Human Gene Therapy 6, 325-333 (1995); Woo et al, WO 94/12629 and Xiao & Brandsma, Nucleic Acids. Res. 24, 2630-2622 (1996)).

DNA encoding an immunogen, or a vector containing the same, can be packaged into liposomes. Suitable lipids and related analogs are described by U.S. Pat. Nos. 5,208,036, 5,264,618, 5,279,833, and 5,283,185. Vectors and DNA encoding an immunogen can also be adsorbed to or associated with particulate carriers, examples of which include polymethyl methacrylate polymers and polylactides and poly(lactide-co-glycolides), (see, e.g., McGee et al., J. Micro Encap. 1996).

H. Antibody Screening Assays

Antibodies can be initially screened for the intended binding specificity as described above. Active immunogens can likewise be screened for capacity to induce antibodies with such binding specificity. In this case, an active immunogen is used to immunize a laboratory animal and the resulting sera tested for the appropriate binding specificity.

Antibodies having the desired binding specificity can then be tested in cellular and animal models. The cells used for such screening are preferentially neuronal cells. A cellular model of tau pathology has been reported in which neuroblastoma cells are transfected with a four-repeat domain of tau, optionally with a mutation associated with tau pathology (e.g., delta K280, see Khlistunova, Current Alzheimer Research 4, 544-546 (2007)). In another model, tau is induced in the neuroblastoma N2a cell line by the addition of doxycycline. The cell models enable one to study the toxicity of tau to cells in the soluble or aggregated state, the appearance of tau aggregates after switching on tau gene expression, the dissolution of tau aggregates after switching the gene expression off again, and the efficiency of antibodies in inhibiting formation of tau aggregates or disaggregating them.

Antibodies or active immunogens can also be screened in transgenic animal models of diseases associated with tau. Such transgenic animals can include a tau transgene (e.g., any of the human isoforms) and optionally a human APP transgene among others, such as a kinase that phosphorylates tau, ApoE, presenilin or alpha synuclein. Such transgenic animals are disposed to develop at least one sign or symptom of a disease associated with tau.

An exemplary transgenic animal is the K3 line of mice (Itner et al., Proc. Natl. Acad. Sci. USA 105(41):15997-6002 (2008)). These mice have a human tau transgene with a K 369 I mutation (the mutation is associated with Pick's disease) and a Thy 1.2 promoter. This model shows a rapid course of neurodegeneration, motor deficit and degeneration of afferent fibers and cerebellar granule cells. Another exemplary animal is the JNPL3 line of mice. These mice have a human tau transgene with a P301L mutation (the mutation is associated with frontotemporal dementia) and a Thy 1.2 promoter (Taconic, Germantown, N.Y., Lewis, et al., Nat Genet. 25:402-405 (2000)). These mice have a more gradual course of neurodegeneration. The mice develop neurofibrillary tangles in several brain regions and spinal cord, which is hereby incorporated by reference in its entirety). This is an excellent model to study the consequences of tangle development and for screening therapy that may inhibit the generation of these aggregates. Another advantage of these animals is the relatively early onset of pathology. In the homozygous line, behavioral abnormalities associated with tau pathology can be observed at least as early as 3 months, but the animals remain relatively healthy at least until 8 months of age. In other words, at 8 months, the animals ambulate, feed themselves, and can perform the behavioral tasks sufficiently well to allow the treatment effect to be monitored. Active immunization of these mice for 6-13 months with—AI wI KLH-PHF-1 generated titers of about 1,000 and showed fewer neurofibrillary tangles, less pSer422, and reduced weight loss relative to untreated control mice.

The activity of antibodies or active agents can be assessed by various criteria including reduction in amount of total tau or phosphorylated tau, reduction in other pathological characteristics, such as amyloid deposits of Aβ, and inhibition or delay or behavioral deficits. Active immunogens can also be tested for induction of antibodies in the sera. Both passive and active immunogens can be tested for passage of antibodies across the blood brain barrier into the brain of a transgenic animal. Antibodies or fragments inducing an antibody can also be tested in non-human primates that naturally or through induction develop symptoms of diseases characterized by tau. Tests on an antibody or active agent are usually performed in conjunction with a control in which a parallel experiment is conduct except that the antibody or active agent is absent (e.g., replaced by vehicle). Reduction, delay or inhibition of signs or symptoms disease attributable to an antibody or active agent under test can then be assessed relative to the control.

VI. Patients Amenable to Treatment

The presence of neurofibrillary tangles has been found in several diseases including Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), and progressive supranuclear palsy (PSP). The present regimes can also be used in treatment or prophylaxis of any of these diseases. Because of the widespread association between neurological diseases and conditions and tau, the present regimes can be used in treatment or prophylaxis of any subject showing elevated levels of tau or phosphorylated tau (e.g., in the CSF) compared with a mean value in individuals without neurological disease. The present regimes can also be used in treatment or prophylaxis of neurological disease in individuals having a mutation in tau associated with neurological disease. The present methods are particularly suitable for treatment or prophylaxis of Alzheimer's disease, and especially in patients.

Patients amenable to treatment include individuals at risk of disease but not showing symptoms, as well as patients presently showing symptoms. Patients at risk of disease include those having a known genetic risk of disease. Such individuals include those having relatives who have experienced this disease, and those whose risk is determined by analysis of genetic or biochemical markers. Genetic markers of risk include mutations in tau, such as those discussed above, as well as mutations in other genes associated with neurological disease. For example, the ApoE4 allele in heterozygous and even more so in homozygous form is associated with risk of Alzheimer's disease. Other markers of risk of Alzheimer's disease include mutations in the APP gene, particularly mutations at position 717 and positions 670 and 671 referred to as the Hardy and Swedish mutations respectively, mutations in the presenilin genes, PS1 and PS2, a family history of AD, hypercholesterolemia or atherosclerosis. Individuals presently suffering from Alzheimer's disease can be recognized by PET imaging, from characteristic dementia, as well as the presence of risk factors described above. In addition, a number of diagnostic tests are available for identifying individuals who have AD. These include measurement of CSF tau or phospho-tau and Aβ42 levels. Elevated tau or phospho-tau and decreased Aβ42 levels signify the presence of AD. Some mutations associated with Parkinson's disease. Ala30Pro or Ala53, or mutations in other genes associated with Parkinson's disease such as leucine-rich repeat kinase, PARKS. Individuals can also be diagnosed with any of the neurological diseases mentioned above by the criteria of the DSM IV TR.

In asymptomatic patients, treatment can begin at any age (e.g., 10, 20, 30). Usually, however, it is not necessary to begin treatment until a patient reaches 40, 50, 60 or 70 years of age. Treatment typically entails multiple dosages over a period of time. Treatment can be monitored by assaying antibody levels over time. If the response falls, a booster dosage is indicated. In the case of potential Down's syndrome patients, treatment can begin antenatally by administering therapeutic agent to the mother or shortly after birth.

I. Nucleic Acids

The invention further provides nucleic acids encoding any of the heavy and light chains described above (e.g., SEQ ID NO:7 and SEQ ID NO:11). Optionally, such nucleic acids further encode a signal peptide and can be expressed with the signal peptide linked to the constant region. Coding sequences of nucleic acids can be operably linked with regulatory sequences to ensure expression of the coding sequences, such as a promoter, enhancer, ribosome binding site, transcription termination signal, and the like. The nucleic acids encoding heavy and light chains can occur in isolated form or can be cloned into one or more vectors. The nucleic acids can be synthesized by, for example, solid state synthesis or PCR of overlapping oligonucleotides. Nucleic acids encoding heavy and light chains can be joined as one contiguous nucleic acid, e.g., within an expression vector, or can be separate, e.g., each cloned into its own expression vector.

J. Conjugated Antibodies

Conjugated antibodies that specifically bind to antigens such as tau, are useful in detecting the presence of tau; monitoring and evaluating the efficacy of therapeutic agents being used to treat patients diagnosed with Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), or progressive supranuclear palsy (PSP); inhibiting or reducing aggregation of tau; inhibiting or reducing tau fibril formation; reducing or clearing tau deposits; stabilizing non-toxic conformations of tau; or treating or effecting prophylaxis of Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), or progressive supranuclear palsy (PSP) in a patient.

For example, such antibodies can be conjugated with other therapeutic moieties, other proteins, other antibodies, and/or detectable labels. See WO 03/057838; U.S. Pat. No. 8,455,622. Such therapeutic moieties can be any agent that can be used to treat, combat, ameliorate, prevent, or improve an unwanted condition or disease in a patient, such as Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), or progressive supranuclear palsy (PSP).

Conjugated therapeutic moieties can include cytotoxic agents, cytostatic agents, neurotrophic agents, neuroprotective agents, radiotherapeutic agents, immunomodulators, or any biologically active agents that facilitate or enhance the activity of the antibody. A cytotoxic agent can be any agent that is toxic to a cell. A cytostatic agent can be any agent that inhibits cell proliferation. A neurotrophic agent can be any agent, including chemical or proteinaceous agents, that promotes neuron maintenance, growth, or differentiation. A neuroprotective agent can be agent, including chemical or proteinaceous agents, that protects neurons from acute insult or degenerative processes. An immunomodulator can be any agent that stimulates or inhibits the development or maintenance of an immunologic response. A radiotherapeutic agent can be any molecule or compound that emits radiation. If such therapeutic moieties are coupled to a tau-specific antibody, such as the antibodies described herein, the coupled therapeutic moieties will have a specific affinity for tau-related disease-affected cells over normal cells. Consequently, administration of the conjugated antibodies directly targets cancer cells with minimal damage to surrounding normal, healthy tissue. This can be particularly useful for therapeutic moieties that are too toxic to be administered on their own. In addition, smaller quantities of the therapeutic moieties can be used.

Some such antibodies can be modified to act as immunotoxins. See, e.g., U.S. Pat. No. 5,194,594. For example, ricin, a cellular toxin derived from plants, can be coupled to antibodies by using the bifunctional reagents S-acetylmercaptosuccinic anhydride for the antibody and succinimidyl 3-(2-pyridyldithio)propionate for ricin. See Pietersz et al., Cancer Res. 48(16):4469-4476 (1998). The coupling results in loss of B-chain binding activity of ricin, while impairing neither the toxic potential of the A-chain of ricin nor the activity of the antibody. Similarly, saporin, an inhibitor of ribosomal assembly, can be coupled to antibodies via a disulfide bond between chemically inserted sulfhydryl groups. See Polito et al., Leukemia 18:1215-1222 (2004).

Some such antibodies can be linked to radioisotopes. Examples of radioisotopes include, for example, yttrium$^{90}$ (90Y), indium$^{111}$ (111In), $^{131}$I, $^{99}$mTc, radiosilver-111, radiosilver-199, and Bismuth$^{213}$. Linkage of radioisotopes to antibodies may be performed with conventional bifunction chelates. For radiosilver-111 and radiosilver-199 linkage, sulfur-based linkers may be used. See Hazra et al., Cell Biophys. 24-25:1-7 (1994). Linkage of silver radioisotopes may involve reducing the immunoglobulin with ascorbic acid. For radioisotopes such as 111In and 90Y, ibritumomab tiuxetan can be used and will react with such isotopes to form 111In-ibritumomab tiuxetan and 90Y-ibritumomab tiuxetan, respectively. See Witzig, Cancer Chemother. Pharmacol., 48 Suppl 1:S91-S95 (2001).

Some such antibodies can be linked to other therapeutic moieties. Such therapeutic moieties can be, for example, cytotoxic, cytostatic, neurotrophic, or neuroprotective. For example, antibodies can be conjugated with toxic chemotherapeutic drugs such as maytansine, geldanamycin, tubulin inhibitors such as tubulin binding agents (e.g., auristatins), or minor groove binding agents such as calicheamicin. Other representative therapeutic moieties include agents known to be useful for treatment, management, or amelioration of Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), or progressive supranuclear palsy (PSP).

Antibodies can also be coupled with other proteins. For example, antibodies can be coupled with Fynomers. Fynomers are small binding proteins (e.g., 7 kDa) derived from the human Fyn SH3 domain They can be stable and soluble, and they can lack cysteine residues and disulfide bonds. Fynomers can be engineered to bind to target molecules with the same affinity and specificity as antibodies. They are suitable for creating multi-specific fusion proteins based on antibodies. For example, Fynomers can be fused to N-terminal and/or C-terminal ends of antibodies to create bi- and tri-specific FynomAbs with different architectures. Fynomers can be selected using Fynomer libraries through screening technologies using FACS, Biacore, and cell-based assays that allow efficient selection of Fynomers with optimal properties. Examples of Fynomers are disclosed in Grabulovski et al., J. Biol. Chem. 282:3196-3204 (2007); Bertschinger et al., Protein Eng. Des. Sel. 20:57-68 (2007); Schlatter et al., MAbs. 4:497-508 (2011); Banner et al., Acta. Crystallogr. D. Biol. Crystallogr. 69(Pt6):1124-1137 (2013); and Brack et al., Mol. Cancer Ther. 13:2030-2039 (2014).

The antibodies disclosed herein can also be coupled or conjugated to one or more other antibodies (e.g., to form antibody heteroconjugates). Such other antibodies can bind to different epitopes within tau or can bind to a different target antigen.

Antibodies can also be coupled with a detectable label. Such antibodies can be used, for example, for diagnosing Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), or progressive supranuclear palsy (PSP), and/or for assessing efficacy of treatment. Such antibodies are particularly useful for performing such determinations in subjects having or being susceptible to Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), or progressive supranuclear palsy (PSP), or in appropriate biological samples obtained from such subjects. Representative detectable labels that may be coupled or linked to an antibody include various enzymes, such as horseradish peroxidase, alkaline phosphatase, beta-galactosidase, or acetylcholinesterase; prosthetic groups, such streptavidin/biotin and avidin/biotin; fluorescent materials, such as umbelliferone, fluorescein, fluorescein isothiocyanate, rhodamine, dichlorotriazinylamine fluorescein, dansyl chloride or phycoerythrin; luminescent materials, such as luminol; bioluminescent materials, such as luciferase, luciferin, and aequorin; radioactive materials, such as radiosilver-111, radiosilver-199, Bismuth$^{213}$, iodine ($^{131}$I, $^{125}$I, $^{123}$I, $^{121}$I), carbon ($^{14}$C), sulfur ($^{5}$S), tritium ($^{3}$H), indium ($^{115}$In, $^{113}$In, $^{112}$In, $^{111}$In), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies; non-radioactive paramagnetic metal ions; and molecules that are radiolabelled or conjugated to specific radioisotopes.

Linkage of radioisotopes to antibodies may be performed with conventional bifunction chelates. For radiosilver-111 and radiosilver-199 linkage, sulfur-based linkers may be used. See Hazra et al., *Cell Biophys.* 24-25:1-7 (1994). Linkage of silver radioisotopes may involve reducing the immunoglobulin with ascorbic acid. For radioisotopes such as 111In and 90Y, ibritumomab tiuxetan can be used and will react with such isotopes to form 111In-ibritumomab tiuxetan and 90Y-ibritumomab tiuxetan, respectively. See Witzig, *Cancer Chemother. Pharmacol.*, 48 Suppl 1:S91-S95 (2001).

Therapeutic moieties, other proteins, other antibodies, and/or detectable labels may be coupled or conjugated, directly or indirectly through an intermediate (e.g., a linker), to an antibody of the invention. See e.g., Arnon et al., "Monoclonal Antibodies For Immunotargeting Of Drugs In Cancer Therapy," in Monoclonal Antibodies And Cancer Therapy, Reisfeld et al. (eds.), pp. 243-56 (Alan R. Liss, Inc. 1985); Hellstrom et al., "Antibodies For Drug Delivery," in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review," in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy," in Monoclonal Antibodies For Cancer Detection And Therapy, Baldwin et al. (eds.), pp. 303-16 (Academic Press 1985); and Thorpe et al., *Immunol. Rev.*, 62:119-58 (1982). Suitable linkers include, for example, cleavable and non-cleavable linkers. Different linkers that release the coupled therapeutic moieties, proteins, antibodies, and/or detectable labels under acidic or reducing conditions, on exposure to specific proteases, or under other defined conditions can be employed.

VI. Pharmaceutical Compositions and Methods of Use

In prophylactic applications, an antibody or agent for inducing an antibody or a pharmaceutical composition the same is administered to a patient susceptible to, or otherwise at risk of a disease (e.g., Alzheimer's disease) in regime (dose, frequency and route of administration) effective to reduce the risk, lessen the severity, or delay the onset of at least one sign or symptom of the disease. In particular, the regime is preferably effective to inhibit or delay tau or phospho-tau and paired filaments formed from it in the brain, and/or inhibit or delay its toxic effects and/or inhibit/ or delay development of behavioral deficits. In therapeutic applications, an antibody or agent to induce an antibody is administered to a patient suspected of, or already suffering from a disease (e.g., Alzheimer's disease) in a regime (dose, frequency and route of administration) effective to ameliorate or at least inhibit further deterioration of at least one sign or symptom of the disease. In particular, the regime is preferably effective to reduce or at least inhibit further increase of levels of tau, phosphor-tau, or paired filaments formed from it, associated toxicities and/or behavioral deficits.

A regime is considered therapeutically or prophylactically effective if an individual treated patient achieves an outcome more favorable than the mean outcome in a control population of comparable patients not treated by methods of the invention, or if a more favorable outcome is demonstrated in treated patients versus control patients in a controlled clinical trial (e.g., a phase II, phase II/III or phase III trial) at the p<0.05 or 0.01 or even 0.001 level.

Effective doses of vary depending on many different factors, such as means of administration, target site, physiological state of the patient, whether the patient is an ApoE carrier, whether the patient is human or an animal, other medications administered, and whether treatment is prophylactic or therapeutic.

Exemplary dosage ranges for antibodies are from about 0.01 to 60 mg/kg, or from about 0.1 to 3 mg/kg or 0.15-2 mg/kg or 0.15-1.5 mg/kg, of patient body weight. Antibody can be administered such doses daily, on alternative days, weekly, fortnightly, monthly, quarterly, or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months.

The amount of an agent for active administration varies from 0.1-500 µg per patient and more usually from 1-100 or 1-10 µg per injection for human administration. The timing of injections can vary significantly from once a day, to once a year, to once a decade. A typical regimen consists of an immunization followed by booster injections at time intervals, such as 6 week intervals or two months. Another regimen consists of an immunization followed by booster injections 1, 2 and 12 months later. Another regimen entails an injection every two months for life. Alternatively, booster injections can be on an irregular basis as indicated by monitoring of immune response.

Antibodies or agents for inducing antibodies are preferably administered via a peripheral route (i.e., one in which an administered or induced antibody crosses the blood brain barrier to reach an intended site in the brain. Routes of administration include topical, intravenous, oral, subcutaneous, intraarterial, intracranial, intrathecal, intraperitoneal, intranasal, intraocular, or intramuscular. Preferred routes for administration of antibodies are intravenous and subcutaneous. Preferred routes for active immunization are subcutaneous and intramuscular. This type of injection is most typically performed in the arm or leg muscles. In some methods, agents are injected directly into a particular tissue where deposits have accumulated, for example intracranial injection.

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use.

The present regimes can be administered in combination with another agent effective in treatment or prophylaxis of the disease being treated. For example, in the case of Alzheimer's disease, the present regimes can be combined with immunotherapy against AP (WO/2000/072880), cholinesterase inhibitors or memantine or in the case of Parkinson's disease immunotherapy against alpha synuclein WO/2008/103472, Levodopa, dopamine agonists, COMT inhibitors, MAO-B inhibitors, Amantadine, or anticholinergic agents.

Antibodies are administered in an effective regime meaning a dosage, route of administration and frequency of administration that delays the onset, reduces the severity, inhibits further deterioration, and/or ameliorates at least one sign or symptom of a disorder being treated. If a patient is already suffering from a disorder, the regime can be referred to as a therapeutically effective regime. If the patient is at elevated risk of the disorder relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a preclinical or clinical trial in a population of treated patients relative to a control population of untreated patients.

Exemplary dosages for an antibody are 0.1-60 mg/kg (e.g., 0.5, 3, 10, 30, or 60 mg/kg), or 0.5-5 mg/kg body weight (e.g., 0.5, 1, 2, 3, 4 or 5 mg/kg) or 10-4000 mg or 10-1500 mg as a fixed dosage. The dosage depends on the condition of the patient and response to prior treatment, if any, whether the treatment is prophylactic or therapeutic and whether the disorder is acute or chronic, among other factors.

Administration can be parenteral, intravenous, oral, subcutaneous, intra-arterial, intracranial, intrathecal, intraperitoneal, topical, intranasal or intramuscular. Some antibodies can be administered into the systemic circulation by intravenous or subcutaneous administration. Intravenous administration can be, for example, by infusion over a period such as 30-90 min The frequency of administration depends on the half-life of the antibody in the circulation, the condition of the patient and the route of administration among other factors. The frequency can be daily, weekly, monthly, quarterly, or at irregular intervals in response to changes in the patient's condition or progression of the disorder being treated. An exemplary frequency for intravenous administration is between weekly and quarterly over a continuous cause of treatment, although more or less frequent dosing is also possible. For subcutaneous administration, an exemplary dosing frequency is daily to monthly, although more or less frequent dosing is also possible.

The number of dosages administered depends on whether the disorder is acute or chronic and the response of the disorder to the treatment. For acute disorders or acute exacerbations of a chronic disorder, between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the patient.

A. Diagnostics and Monitoring Methods

In Vivo Imaging, Diagnostic Methods, and Optimizing Immunotherapy

The invention provides methods of in vivo imaging tau protein deposits (e.g., neurofibrillary tangles and tau inclusions) in a patient. The methods work by administering a reagent, such as antibody that binds tau (e.g., a mouse, humanized, chimeric or veneered 16G7 antibody), to the patient and then detecting the agent after it has bound. In some methods, the antibody binds to an epitope of tau within amino acid residues 55-78 of SEQ ID NO:3 (corresponding to amino acid residues 113-136 of SEQ ID NO:1). In some methods, the antibody binds to an epitope within amino acid residues 60-75 of SEQ ID NO:3 (corresponding to amino acid residues 118-133 of SEQ ID NO:1), or within amino acid residues 61-70 of SEQ ID NO:3 (corresponding to amino acid residues 119-128 of SEQ ID NO:1). A clearing response to the administered antibodies can be avoided or reduced by using antibody fragments lacking a full-length constant region, such as Fabs. In some methods, the same antibody can serve as both a treatment and diagnostic reagent.

Diagnostic reagents can be administered by intravenous injection into the body of the patient, or directly into the brain by intracranial injection or by drilling a hole through the skull. The dosage of reagent should be within the same ranges as for treatment methods. Typically, the reagent is labeled, although in some methods, the primary reagent with affinity for tau is unlabeled and a secondary labeling agent is used to bind to the primary reagent. The choice of label depends on the means of detection. For example, a fluorescent label is suitable for optical detection. Use of paramagnetic labels is suitable for tomographic detection without surgical intervention. Radioactive labels can also be detected using positron emission tomography (PET) or single-photon emission computed tomography (SPECT).

The methods of in vivo imaging of tau protein deposits are useful to diagnose or confirm diagnosis of a tauopathy, such as Alzheimer's disease, frontotemporal lobar degeneration, progressive supranuclear palsy and Pick's disease, or susceptibility to such a disease. For example, the methods can be used on a patient presenting with symptoms of dementia. If the patient has abnormal neurofibrillary tangles, then the patient is likely suffering from Alzheimer's disease. Alternatively, if the patient has abnormal tau inclusions, then depending on the location of the inclusions, the patient may be suffering from frontotemporal lobar degeneration. The methods can also be used on asymptomatic patients. Presence of abnormal tau protein deposits indicates susceptibility to future symptomatic disease. The methods are also useful for monitoring disease progression and/or response to treatment in patients who have been previously diagnosed with a tau-related disease.

Diagnosis can be performed by comparing the number, size, and/or intensity of labeled loci, to corresponding baseline values. The base line values can represent the mean levels in a population of undiseased individuals. Baseline values can also represent previous levels determined in the same patient. For example, baseline values can be determined in a patient before beginning tau immunotherapy treatment, and measured values thereafter compared with the baseline values. A decrease in values relative to baseline signals a positive response to treatment.

In some patients, diagnosis of a tauopathy may be aided by performing a PET scan. A PET scan can be performed using, for example, a conventional PET imager and auxiliary equipment. The scan typically includes one or more regions of the brain known in general to be associated with tau protein deposits and one or more regions in which few if any deposits are generally present to serve as controls.

The signal detected in a PET scan can be represented as a multidimensional image. The multidimensional image can be in two dimensions representing a cross-section through the brain, in three dimensions, representing the three dimensional brain, or in four dimensions representing changes in the three dimensional brain over time. A color scale can be used with different colors indicating different amounts of label and, inferentially, tau protein deposit detected. The results of the scan can also be presented numerically, with numbers relating to the amount of label detected and consequently amount of tau protein deposits. The label present in a region of the brain known to be associated with deposits for a particular tauopathy (e.g., Alzheimer's disease) can be compared with the label present in a region known not to be associated with deposits to provide a ratio indicative of the extent of deposits within the former region. For the same radiolabeled ligand, such ratios provide a comparable measure of tau protein deposits and changes thereof between different patients.

In some methods, a PET scan is performed concurrent with or in the same patient visit as an MRI or CAT scan. An MRI or CAT scan provides more anatomical detail of the brain than a PET scan. However, the image from a PET scan can be superimposed on an MRI or CAT scan image more precisely indicating the location of PET ligand and inferentially tau deposits relative to anatomical structures in the brain. Some machines can perform both PET scanning and MRI or CAT scanning without the patient changing positions between the scans facilitating superimposition of images.

Suitable PET ligands include radiolabeled antibodies of the invention (e.g., a mouse, humanized, chimeric or veneered 16G7 antibody). The radioisotope used can be, for example, $C^{11}$, $N^{13}$, $O^{15}$, $F^{18}$, or $I^{123}$. The interval between administering the PET ligand and performing the scan can depend on the PET ligand and particularly its rate of uptake and clearing into the brain, and the half-life of its radiolabel.

PET scans can also be performed as a prophylactic measure in asymptomatic patients or in patients who have symptoms of mild cognitive impairment but have not yet been diagnosed with a tauopathy but are at elevated risk of developing a tauopathy. For asymptomatic patients, scans are particularly useful for individuals considered at elevated risk of tauopathy because of a family history, genetic or biochemical risk factors, or mature age. Prophylactic scans can commence for example, at a patient age between 45 and 75 years. In some patients, a first scan is performed at age 50 years.

Prophylactic scans can be performed at intervals of for example, between six months and ten years, preferably between 1-5 years. In some patients, prophylactic scans are performed annually. If a PET scan performed as a prophylactic measure indicates abnormally high levels of tau protein deposits, immunotherapy can be commenced and subsequent PET scans performed as in patients diagnosed with a tauopathy. If a PET scanned performed as a prophylactic measure indicates levels of tau protein deposits within normal levels, further PET scans can performed at intervals of between six months and 10 years, and preferably 1-5 years, as before, or in response to appearance of signs and symptoms of a tauopathy or mild cognitive impairment. By combining prophylactic scans with administration of tau-directed immunotherapy if and when an above normal level of tau protein deposits is detected, levels of tau protein deposits can be reduced to, or closer to, normal levels, or at least inhibited from increasing further, and the patient can remain free of the tauopathy for a longer period than if not receiving prophylactic scans and tau-directed immunotherapy (e.g., at least 5, 10, 15 or 20 years, or for the rest of the patient's life).

Normal levels of tau protein deposits can be determined by the amount of neurofibrillary tangles or tau inclusions in the brains of a representative sample of individuals in the general population who have not been diagnosed with a particular tauopathy (e.g., Alzheimer's disease) and are not considered at elevated risk of developing such disease (e.g., a representative sample of disease-free individuals under 50 years of age). Alternatively, a normal level can be recognized in an individual patient if the PET signal according to the present methods in a region of the brain in which tau protein deposits are known to develop is not different (within the accuracy of measurement) from the signal from a region of the brain in which it is known that such deposits do not normally develop. An elevated level in an individual can be recognized by comparison to the normal levels (e.g., outside mean and variance of a standard deviation) or simply from an elevated signal beyond experimental error in a region of the brain associated with tau protein deposits compared with a region not known to be associated with deposits. For purposes of comparing the levels of tau protein deposits in an individual and population, the tau protein deposits should preferably be determined in the same region(s) of the brain, these regions including at least one region in which tau protein deposits associated with a particular tauopathy (e.g., Alzheimer's disease) are known to form. A patient having an elevated level of tau protein deposits is a candidate for commencing immunotherapy.

After commencing immunotherapy, a decrease in the level of tau protein deposits can be first seen as an indication that the treatment is having the desired effect. The observed decrease can be, for example, in the range of 1-100%, 1-50%, or 1-25% of the baseline value. Such effects can be measured in one or more regions of the brain in which deposits are known to form or can be measured from an average of such regions. The total effect of treatment can be approximated by adding the percentage reduction relative to baseline to the increase in tau protein deposits that would otherwise occur in an average untreated patient.

Maintenance of tau protein deposits at an approximately constant level or even a small increase in tau protein deposits can also be an indication of response to treatment albeit a suboptimal response. Such responses can be compared with a time course of levels of tau protein deposits in patients with a particular tauopathy (e.g., Alzheimer's disease) that did not receive treatment, to determine whether the immunotherapy is having an effect in inhibiting further increases of tau protein deposits.

Monitoring of changes in tau protein deposits allows adjustment of the immunotherapy or other treatment regime in response to the treatment. PET monitoring provides an indication of the nature and extent of response to treatment. Then a determination can be made whether to adjust treatment and if desired treatment can be adjusted in response to the PET monitoring. PET monitoring thus allows for tau-directed immunotherapy or other treatment regime to be adjusted before other biomarkers, MRI or cognitive measures have detectably responded. A significant change means that comparison of the value of a parameter after treatment relative to basement provides some evidence that treatment has or has not resulted in a beneficial effect. In some instances, a change of values of a parameter in a patient itself provides evidence that treatment has or has not resulted in a beneficial effect. In other instances, the change of values, if any, in a patient, is compared with the change of values, if any, in a representative control population of patients not undergoing immunotherapy. A difference in response in a particular patient from the normal response in the control patient (e.g., mean plus variance of a standard deviation) can also provide evidence that an immunotherapy regime is or is not achieving a beneficial effect in a patient.

In some patients, monitoring indicates a detectable decline in tau protein deposits but that the level of tau protein deposits remains above normal. In such patients, if there are no unacceptable side effects, the treatment regime can be continued as is or even increased in frequency of administration and/or dose if not already at the maximum recommended dose.

If the monitoring indicates levels of tau protein deposits in a patient have already been reduced to normal, or near-normal, levels of tau protein deposits, the immunotherapy regime can be adjusted from one of induction (i.e., that reduces the level of tau protein deposits) to one of maintenance (i.e., that maintains tau protein deposits at an approximately constant level). Such a regime can be affected by reducing the dose and or frequency of administering immunotherapy.

In other patients, monitoring can indicate that immunotherapy is having some beneficial effect but a suboptimal effect. An optimal effect can be defined as a percentage reduction in the level of tau protein deposits within the top half or quartile of the change in tau protein deposits (measured or calculated over the whole brain or representative region(s) thereof in which tau protein deposits are known to form) experienced by a representative sample of tauopathy patients undergoing immunotherapy at a given time point after commencing therapy. A patient experiencing a smaller decline or a patient whose tau protein deposits remains constant or even increases, but to a lesser extent than expected in the absence of immunotherapy (e.g., as inferred from a control group of patients not administered immunotherapy) can be classified as experiencing a positive but suboptimal response. Such patients can optionally be subject to an adjustment of regime in which the dose and or frequency of administration of an agent is increased.

In some patients, tau protein deposits may increase in similar or greater fashion to tau deposits in patients not receiving immunotherapy. If such increases persist over a period of time, such as 18 months or 2 years, even after any increase in the frequency or dose of agents, immunotherapy can if desired be discontinued in favor of other treatments.

The foregoing description of diagnosing, monitoring, and adjusting treatment for tauopathies has been largely focused on using PET scans. However, any other technique for visualizing and/or measuring tau protein deposits that is amenable to the use of tau antibodies of the invention (e.g., a mouse, humanized, chimeric or veneered 16G7 antibody) can be used in place of PET scans to perform such methods.

Also provided are methods of detecting an immune response against tau in a patient suffering from or susceptible to diseases associated with tau. The methods can be used to monitor a course of therapeutic and prophylactic treatment with the agents provided herein. The antibody profile following passive immunization typically shows an immediate peak in antibody concentration followed by an exponential decay. Without a further dose, the decay approaches pretreatment levels within a period of days to months depending on the half-life of the antibody administered. For example, the half-life of some human antibodies is of the order of 20 days.

In some methods, a baseline measurement of antibody to tau in the subject is made before administration, a second measurement is made soon thereafter to determine the peak antibody level, and one or more further measurements are made at intervals to monitor decay of antibody levels. When the level of antibody has declined to baseline or a predetermined percentage of the peak less baseline (e.g., 50%, 25% or 10%), administration of a further dose of antibody is administered. In some methods, peak or subsequent measured levels less background are compared with reference levels previously determined to constitute a beneficial prophylactic or therapeutic treatment regime in other subjects. If the measured antibody level is significantly less than a reference level (e.g., less than the mean minus one or, preferably, two standard deviations of the reference value in a population of subjects benefiting from treatment) administration of an additional dose of antibody is indicated.

Also provided are methods of detecting tau in a subject, for example, by measuring tau in a sample from a subject or by in vivo imaging of tau in a subject. Such methods are useful to diagnose or confirm diagnosis of diseases associated with tau, or susceptibility thereto. The methods can also be used on asymptomatic subjects. The presence of tau indicates susceptibility to future symptomatic disease. The methods are also useful for monitoring disease progression and/or response to treatment in subjects who have been previously diagnosed with Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), or progressive supranuclear palsy (PSP).

Biological samples obtained from a subject having, suspected of having, or at risk of having Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), or progressive supranuclear palsy (PSP) can be contacted with the antibodies disclosed herein to assess the presence of tau. For example, levels of tau in such subjects may be compared to those present in healthy subjects. Alternatively, levels of tau in such subjects receiving treatment for the disease may be compared to those of subjects who have not been treated for Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), or progressive supranuclear palsy (PSP). Some such tests involve a biopsy of tissue obtained from such subjects. ELISA assays may also be useful methods, for example, for assessing tau in fluid samples.

IX. Kits

The invention further provides kits (e.g., containers) comprising an antibody disclosed herein and related materials, such as instructions for use (e.g., package insert). The instructions for use may contain, for example, instructions for administration of the antibody and optionally one or more additional agents. The containers of antibody may be unit doses, bulk packages (e.g., multi-dose packages), or sub-unit doses.

Package insert refers to instructions customarily included in commercial packages of therapeutic products that contain information about the indications, usage, dosage, administration, contraindications and/or warnings concerning the use of such therapeutic products.

Kits can also include a second container comprising a pharmaceutically-acceptable buffer, such as bacteriostatic water for injection (BWFI), phosphate-buffered saline, Ringer's solution and dextrose solution. It can also include other materials desirable from a commercial and user standpoint, including other buffers, diluents, filters, needles, and syringes.

X. Other Applications

The antibodies can be used for detecting tau or fragments thereof, in the context of clinical diagnosis or treatment or in research. For example, the antibodies can be used to detect the presence of tau in a biological sample as an indication that the biological sample comprises tau deposits. Binding of the antibodies to the biological sample can be compared to binding of the antibodies to a control sample. The control sample and the biological sample can comprise cells of the same tissue origin. Control samples and biological samples can be obtained from the same individual or different individuals and on the same occasion or on different occasions. If desired, multiple biological samples and multiple control samples are evaluated on multiple occasions to protect against random variation independent of the differences between the samples. A direct comparison can then be made between the biological sample(s) and the control sample(s) to determine whether antibody binding (i.e., the presence of tau) to the biological sample(s) is increased, decreased, or the same relative to antibody binding to the control sample(s). Increased binding of the antibody to the biological sample(s) relative to the control sample(s) indicates the presence of tau in the biological sample(s). In some instances, the increased antibody binding is statistically significant. Optionally, antibody binding to the biological sample is at least 1.5-fold, 2-fold, 3-fold, 4-fold, 5-fold, 10-fold, 20-fold, or 100-fold higher than antibody binding to the control sample.

In addition, the antibodies can be used to detect the presence of the tau in a biological sample to monitor and evaluate the efficacy of a therapeutic agent being used to treat a patient diagnosed with Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), or progressive supranuclear palsy (PSP). A biological sample from a patient diagnosed with Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), or progressive supranuclear palsy (PSP) is evaluated to establish a baseline for the binding of the antibodies to the sample (i.e., a baseline for the presence of the tau in the sample) before commencing therapy with the therapeutic agent. In some instances, multiple biological samples from the patient are evaluated on multiple occasions to establish both a baseline and measure of random variation independent of treatment. A therapeutic agent is then administered in a regime. The regime may include multiple administrations of the agent over a period of time. Optionally, binding of the antibodies (i.e., presence of tau) is evaluated on multiple occasions in multiple biological samples from the patient, both to establish a measure of random variation and to show a trend in response to immunotherapy. The various assessments of antibody binding to the biological samples are then compared. If only two assessments are made, a direct comparison can be made between the two assessments to determine whether antibody binding (i.e., presence of tau) has increased, decreased, or remained the same between the two assessments. If more than two measurements are made, the measurements can be analyzed as a time course starting before treatment with the therapeutic agent and proceeding through the course of therapy. In patients for whom antibody binding to biological samples has decreased (i.e., the presence of tau), it can be concluded that the therapeutic agent was effective in treating the Alzheimer's disease, Down's syndrome, mild cognitive impairment, primary age-related tauopathy, postencephalitic parkinsonism, posttraumatic dementia or dementia pugilistica, Pick's EFORMAT type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), or progressive supranuclear palsy (PSP) in the patient. The decrease in antibody binding can be statistically significant. Optionally, binding decreases by at least 1%, 2%, 3%, 4%, 5%, 10%, 15%, 20%, 30%, 40%, 50%, 60%, 70%, 80%, 90%, or 100%. Assessment of antibody binding can be made in conjunction with assessing other signs and symptoms of Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), or progressive supranuclear palsy (PSP).

The antibodies can also be used as research reagents for laboratory research in detecting tau, or fragments thereof. In such uses, antibodies can be labeled with fluorescent molecules, spin-labeled molecules, enzymes, or radioisotopes, and can be provided in the form of kit with all the necessary reagents to perform the detection assay. The antibodies can also be used to purify tau, or binding partners of tau, e.g., by affinity chromatography.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

Example 1. Identification of Tau Monoclonal Antibodies

Monoclonal antibody 16G7 was prepared according to a modification of the method of Kohler and Milstein (G. Kohler and C. Milstein (1975) Nature 256:495-497). Human tau containing all 4 microtubule binding repeats, and lacking the N-terminal splice variants (4R0N tau, 383 amino acids) was used in all injections and screening assays. Tau was purified from SF9 cells infected with a tau-containing baculovirus construct (J. Knops et al. (1991) J Cell Biol 115(5): 725-33). Six week old ALI mice were injected with 100 µg of purified tau at two week intervals. Tau was emulsified in complete Freund's adjuvant for the first immunization and in incomplete Freund's adjuvant for all subsequent immunizations. Serum samples were taken three days after the third injection to assess the titer of these animals. The highest titer mouse was injected intravenously with 100 µg of tau in 500 µL of PBS two weeks after receiving its third injection. The myeloma fusion occurred three days later using SP2/0 as the fusion partner. Supernatants from wells containing hybridoma cells were screened for their ability to precipitate $^{125}$I-labeled tau. Tau was radio-iodinated using immobilized glucose oxidase and lactoperoxidase according to the manufacturer's instructions (Bio-Rad). Briefly, 10 µg of purified recombinant tau was radiolabeled with 1 mCi of Na$^{125}$I to a specific activity of 20 µCi/µg, protein. 16G7 was identified as a high-affinity monoclonal antibody specific to tau and was cloned by limiting dilution. The isotypes of 16G7 was determined to be gamma 1 kappa.

Example 2. Epitope Mapping of Antibody 16G7

A range of overlapping biotinylated peptides spanning the entire 383aa 4R0N human tau protein were used for mapping the murine 16G7 antibody. Additional peptides were used to model potential post-translational modifications of the C- and N-terminal ends of the protein.

Biotinylated peptides were bound to separate wells of a streptavidin-coated ELISA plate. The plate was blocked and treated with murine 16G7, followed by incubation with a horseradish peroxidase-conjugated anti-mouse antibody. After thorough washing, OPD was applied to the plate and allowed to develop. The plate was read at 450 nm absorbance. Background subtraction was performed with absorbance values from wells containing no primary antibody, and a threshold for positive binding was set to 0.2 absorbance units.

Positive binding was detected for the peptide spanning amino acid residues 55-69 of SEQ ID NO:3, with lesser binding detected towards the peptide spanning amino acid residues 64-78 of SEQ ID NO:3 (FIG. 1). Using the numbering of the full-length 4R2N human tau protein (441 amino acids) (SEQ ID NO:1) these peptides correspond to amino acid residues 113-127 and 122-136, respectively, of SEQ ID NO:1.

Example 3. Design of Humanized 16G7 Antibodies

The starting point or donor antibody for humanization was the mouse antibody 16G7. The heavy chain variable amino acid sequence of mature m16G7 is provided as SEQ ID NO:7. The light chain variable amino acid sequence of mature m16G7 is provided as SEQ ID NO:11. The heavy chain Kabat/Chothia Composite CDR1, CDR2, and CDR3 amino acid sequences are provided as SEQ ID NOs:8-10, respectively. The light chain Kabat CDR1, CDR2, and CDR3 amino acid sequences are provided as SEQ ID NOs12-14 respectively. Kabat numbering is used throughout.

The variable kappa (Vk) of 16G7 belongs to mouse Kabat subgroup 1 which corresponds to human Kabat subgroup 4 and the variable heavy (Vh) to mouse Kabat subgroup 2b which corresponds to human Kabat subgroup 1 [Kabat E. A., et al., (1991), Sequences of Proteins of Immunological Interest, Fifth Edition. NIH Publication No. 91-3242]. 17 residue Chothia CDR-L1 belongs to canonical class 3, 7 residue Chothia CDR-L2 to class 1, 9 residue Chothia CDR-L3 to class 1 in Vk [Martin A. C, and Thornton J. M. (1996) J. Mol. Biol. 263:800-15.]. 10 residue Chothia CDR-H1 belongs to class 1, 17 residue Chothia CDR-H2 to class 2 [Martin & Thornton, 1996]. CDR-H3 has no canonical classes, but the 9 residue loop probably has a kinked base according to the rules of Shirai et al [Shirai H, et al., (1999) FEBS Lett. 455:188-97.]. A search was made over the protein sequences in the PDB database [Deshpande N, et al., (2005) Nucleic Acids Res. 33: D233-7.] to find structures which would provide a rough structural model of 16G7. The structure of the anti 0-antigen of *Francisella tularenis* FAB (pdb code 3UJT) [Rynkiewicz, M. J., et al., (2012) Biochemistry 51: 5684-5694] with a resolution of 2.1A was used to build up a Fv model of 16G7. It retained the same canonical structure for the loops as 16G7. For VLv1, VLv2, and VLv3, human VL acceptors AAB24404.1 and AEK69364.1 from a search of the non-redundant protein sequence database from NCBI were also applied (following the previous INN humanization rule). For VHv1, VHv2, VHv3, VHv4, VHv5V and VHv5VR, acceptors AAA18265.1 and ADW08092.1 from a search of the non-redundant protein sequence database from NCBI were also applied (following the previous INN humanization rule).

Following 2015 INN antibody humanization rule [Jones, T. D., et al, (2016), The INNs and outs of antibody nonproprietary names. mAbs (http://dx.doi.org/10.1080/19420862.2015.1114320)], a search of IMGT database allowed selection of suitable human germline frameworks into which to graft the murine CDRs. For Vk, a human kappa light chain with IMGT#IGKV4-1*01 was chosen. This has the same canonical classes for CDR-L1, CDR-L2 and L3, and belongs to human kappa subgroup 1. For Vh, human heavy chain with IMGT #IGHV1-2*02 was chosen, which belongs to human heavy chain subgroup 1. It shares the canonical form of 16G7 CDR-H1 and H2. VHv2a, VHv2b, VHv2aB7, VHv2bH7, VHv6a, VHv6b and VHv7 were designed using IMGT #IGHV1-2*02 as an acceptor.

Heavy and light chain variant sequences resulting from antibody humanization process were further aligned to human germ line sequences using IMGT Domain GapAlign tool to assess the humanness of the heavy and light chain as outlined by WHO INN committee guidelines. (WHO-INN: International nonproprietary names (INN) for biological and biotechnological substances (a review) (Internet) 2014. Available from: http://www.who.int/medicines/services/inn/BioRev2014.pdf) Residues were changed to align with corresponding human germ line sequence, where possible, to enhance humanness.

13 humanized heavy chain variable region variants and 3 humanized light chain variable region variants were constructed containing different permutations of substitutions (hu16G7VHv1, hu16G7VHv2, hu16G7VHv2a, 16G7VHv2aB7, hu16G7VHv2b, hu16G7VHv2bH7, hu16G7VHv3, hu16G7VHv4, hu16G7VHv5V, hu16G7VHv5VR, hu16G7VHv6a, hu16G7VHv6b, and hu16G7VHv7, (SEQ ID NOs: 15-27, respectively) and hu16G7VLv1. hu16G7VLv2, and hu16G7VLv3 (SEQ ID NOS:28-30, respectively) FIGS. 9A-E and FIGS. 8A-D). The exemplary humanized Vk and Vh designs, with backmutations and other mutations based on selected human frameworks, are shown in FIGS. 8A-D and FIGS. 9A-E, respectively. The bolded areas in FIGS. 8A-D and FIGS. 9A-E indicate the CDRs as defined by Kabat/Chothia Composite. SEQ ID NOs: 15-27 and SEQ ID NOs: 28-30 contain backmutations and other mutations as shown in Table 3. The amino acids at positions H1, H5, H7, H9, H10, H11, H12, H13, H20, H31, H37, H38, H40, H48, H60, H64, H66, H67, H69, H71, H73, H75, H80, H82s, H82b, H83, and H85 in hu16G7VHv1, hu16G7VHv2), hu16G7VHv2a, 16G7VHv2aB7, hu16G7VHv2b, hu16G7VHv2bH7, hu16G7VHv3, hu16G7VHv4, hu16G7VHv5V, hu16G7VHv5VR, hu16G7VHv6a, hu16G7VHv6b, and hu16G7VHv7 are listed in Table 4. The amino acids at positions in L4, L9, L15, L18, L19, L21, L22, L43, and L48 hu16G7VLv1. hu16G7VLv2, and hu16G7VLv3 at are listed in Table 5. The percentage humanness for humanized VH chains hu16G7VHv1, hu16G7VHv2, hu16G7VHv2a, 16G7VHv2aB7, hu16G7VHv2b, hu16G7VHv2bH7, hu16G7VHv3, hu16G7VHv4, hu16G7VHv5V, hu16G7VHv5VR, hu16G7VHv6a, hu16G7VHv6b, and hu16G7VHv7, (SEQ ID NOs: 15-27, respectively) and humanized VL chains hu16G7VLv1. hu16G7VLv2, and hu16G7VLv3 (SEQ ID NOS:28-30, respectively) is shown in Table 6.

TABLE 3

$V_H$, $V_L$ Backmutations and Other Mutations for Humanized 16G7

| $V_H$ or $V_L$ Variant | $V_H$ or $V_L$ Exon Acceptor Sequence | Changes from Acceptor Framework and CDR Residues (based on Kabat/Chothia Composite CDRs) |
|---|---|---|
| hu16G7VHv1 (SEQ ID NO: 15) | NCBI accession code IMGT# IGHV1-2*02 (SEQ (ID NO: 33) | H1, H5, H7, H9, H10, H11, H12, H13, H20, H37, H38, H40, H48, H66, H67, H69, H71, H73, H75, H80, H82A, H82B, H83, H85 |
| hu16G7VHv2 (SEQ ID NO: 16) | NCBI accession code IMGT# IGHV1-2*02 (SEQ (ID NO: 33) | H1, H5, H11, H12, H20, H48, H69, H71, H75, H82A, H82B, H83, H85 |
| hu16G7VHv2a (SEQ ID NO: 17) | NCBI accession code IMGT# IGHV1-2*02 (SEQ (ID NO: 33) | H1, H12, H40, H48, H66, H67, H69, H71, H73, H83 |
| 16G7VHv2aB7 (SEQ ID NO: 18) | NCBI accession code IMGT# IGHV1-2*02 (SEQ (ID NO: 33) | H1, H12, H31, H40, H48, H60, H66, H67, H69, H71, H73, H83 |
| hu16G7VHv2b (SEQ ID NO: 19) | NCBI accession code IMGT# IGHV1-2*02 (SEQ (ID NO: 33) | H1, H12, H40, H48, H69, H73, H83 |
| hu16G7VHv2bH7 (SEQ ID NO: 20) | NCBI accession code IMGT# IGHV1-2*02 (SEQ (ID NO: 33) | H1, H12, H31, H40, H48, H60, H64, H69, H73, H83 |
| hu16G7VHv3 (SEQ ID NO: 21) | NCBI accession code IMGT# IGHV1-2*02 (SEQ (ID NO: 33) | H1, H5, H7, H9, H10, H11, H12, H13, H20, H48, H69, H71, H75, H82A, H82B, H83, H85 |
| hu16G7VHv4 (SEQ ID NO: 22) | NCBI accession code IMGT# IGHV1-2*02 (SEQ (ID NO: 33) | H1, H5, H11, H12, H20, H48, H66, H67, H69, H71, H73, H75, H82A, H82B, H83, H85 |

TABLE 3-continued

V_H, V_L Backmutations and Other Mutations for Humanized 16G7

| V_H or V_L Variant | V_H or V_L Exon Acceptor Sequence | Changes from Acceptor Framework and CDR Residues (based on Kabat/Chothia Composite CDRs) |
|---|---|---|
| hu16G7VHv5V (SEQ ID NO: 23) | NCBI accession code IMGT# IGHV1-2*02 (SEQ (ID NO: 33) | H1, H5, H7, H9, H10, H11, H12, H13, H20, H38, H40, H48, H66, H67, H69, H71, H73, H75, H80, H82A, H82B, H83, H85 |
| hu16G7VHv5VR (SEQ ID NO: 24) | NCBI accession code IMGT# IGHV1-2*02 (SEQ (ID NO: 33) | H1, H5, H7, H9, H10, H11, H12, H13, H20, H40, H48, H66, H67, H69, H71, H73, H75, H80, H82A, H82B, H83, H85 |
| hu16G7VHv6a (SEQ ID NO: 25) | NCBI accession code IMGT# IGHV1-2*02 (SEQ (ID NO: 33) | H7, H71, H73 |
| hu16G7VHv6b (SEQ ID NO: 26) | NCBI accession code IMGT# IGHV1-2*02 (SEQ (ID NO: 33) | H71 |
| hu16G7VHv7 (SEQ ID NO: 27) | NCBI accession code IMGT# IGHV1-2*02 (SEQ (ID NO: 33) | H1, H7, H71, H73 |
| Hu16G7VLv1 (SEQ ID NO: 28) | NCBI accession code IMGT# IGKV4-1*01 (SEQ ID NO: 36) | L4, L9, L15, L18, L19, L21, L22, L43, L48 |
| Hu16G7VLv2 (SEQ ID NO: 29) | NCBI accession code IMGT# IGKV4-1*01 (SEQ ID NO: 36)) | L4, L9, L15, L22, L43 |
| Hu16G7VLv3 (SEQ ID NO: 30) | NCBI accession code IMGT# IGKV4-1*01 (SEQ ID NO: 36) | L4, L9, L15, L18, L19, L21, L22, L43 |

TABLE 4

Kabat Numbering of Framework (or CDR) Residues (based on Kabat/Chothia Composite CDRs) for Backmutations and Other Mutations in Heavy Chains of Humanized 16G7 Antibodies

| Residue | (Heavy Chain) Mouse 16G7 | hu16G7VHv1 | hu16G7VHv2 | hu16G7VHv2a | 16G7VHv2aB7 | hu16G7VHv2b | hu16G7VHv2bH7 | hu16G7VHv3 |
|---|---|---|---|---|---|---|---|---|
| H1 | Q | Q | E | E | E | E | E | E |
| H5 | V | Q | Q | Q | V | V | V | V | Q |
| H7 | S | P | P | S | S | S | S | S | P |
| H9 | A | S | S | A | A | A | A | A | S |
| H10 | E | V | V | E | E | E | E | E | V |
| H11 | V | L | L | L | V | V | V | V | L |
| H12 | K | V | V | V | V | V | V | V | V |
| H13 | K | R | R | K | K | K | K | K | R |
| H20 | V | L | L | L | V | V | V | V | L |
| H31 | G | S | S | S | S | G | S | G | S |
| H37 | V | A | A | V | V | V | V | V | V |
| H38 | R | K | K | R | R | R | R | R | R |
| H40 | A | R | R | A | R | R | R | R | A |
| H48 | M | I | I | I | I | I | I | I | I |
| H60 | A | N | N | N | N | A | N | A | N |
| H64 | Q | K | K | K | K | K | K | Q | K |
| H66 | R | K | K | R | K | K | R | R | R |
| H67 | V | A | A | V | A | A | V | V | V |
| H69 | M | L | L | L | L | L | L | L | L |
| H71 | R | V | V | V | V | V | R | R | V |
| H73 | T | I | I | T | I | I | I | I | T |
| H75 | I | S | S | A | I | I | I | I | A |
| H80 | M | V | V | M | M | M | M | M | M |
| H82A | S | T | T | T | S | S | S | S | T |
| H82B | R | S | S | S | R | R | R | R | S |
| H83 | R | T | T | T | T | T | T | T | T |
| H85 | D | E | E | E | D | D | D | D | E |

| Residue | hu16G7VHv4 | hu16G7VHv5V | hu16G7VHv5VR | hu16G7VHv6a | hu16G7VHv6b | hu16G7VHv7 |
|---|---|---|---|---|---|---|
| H1 | E | E | E | Q | Q | E |
| H5 | Q | Q | Q | V | V | V |
| H7 | S | P | P | p | S | P |
| H9 | A | S | S | A | A | A |
| H10 | E | V | V | E | E | E |
| H11 | L | L | L | V | V | V |
| H12 | V | V | V | K | K | K |
| H13 | K | R | R | K | K | K |
| H20 | L | L | L | V | V | V |
| H31 | S | S | S | S | S | S |

TABLE 4-continued

Kabat Numbering of Framework (or CDR) Residues (based on
Kabat/Chothia Composite CDRs) for Backmutations and Other Mutations in Heavy
Chains of Humanized 16G7 Antibodies

| | | | | | | |
|---|---|---|---|---|---|---|
| H37 | V | V | V | V | V | V |
| H38 | R | K | R | R | R | R |
| H40 | A | R | R | A | A | A |
| H48 | I | I | I | M | M | M |
| H60 | N | N | N | N | N | N |
| H64 | K | K | K | K | K | K |
| H66 | K | K | K | R | R | R |
| H67 | A | A | A | V | V | V |
| H69 | L | L | L | M | M | M |
| H71 | V | V | V | V | V | V |
| H73 | I | I | I | I | T | I |
| H75 | S | S | S | I | I | I |
| H80 | M | V | V | M | M | M |
| H82A | T | T | T | S | S | S |
| H82B | S | S | S | R | R | R |
| H83 | T | T | T | R | R | R |
| H85 | E | E | E | D | D | D |

TABLE 5

Kabat Numbering of Framework Residues (based on Kabat/Chothia Composite CDRs)
for Backmutations and Other Mutations in Light Chains of Humanized 16G7 Antibodies

| Residue | IMGT#IGKV4-1*01 (Light Chain) | Mouse 16G7 | Hu16G7VLv1 | Hu16G7VLv2 | Hu16G7VLv3 |
|---|---|---|---|---|---|
| L4 | M | L | L | L | L |
| L9 | D | S | S | S | S |
| L15 | L | V | V | V | V |
| L18 | R | K | K | R | K |
| L19 | A | V | V | A | V |
| L21 | I | M | M | I | M |
| L22 | N | S | S | S | S |
| L43 | P | S | S | S | S |
| L48 | I | M | M | I | I |

TABLE 6

Percentage Humanness of Heavy and Light
Chains of Humanized 16G7 Antibodies

| $V_H$ or $V_L$ Variant | % Humanness |
|---|---|
| hu16G7VHv1 (SEQ ID NO: 15) | 64.30% |
| hu16G7VHv2 (SEQ ID NO: 16) | 76.50% |
| hu16G7VHv2a (SEQ ID NO: 17) | 79.60% |
| 16G7VHv2aB7 (SEQ ID NO: 18) | 81.60% |
| hu16G7VHv2b (SEQ ID NO: 19) | 82.70% |
| hu16G7VHv2bH7 (SEQ ID NO: 20) | 85.70% |
| hu16G7VHv3 (SEQ ID NO: 21) | 72.40% |
| hu16G7VHv4 (SEQ ID NO: 22) | 73.50% |
| hu16G7VHv5V (SEQ ID NO: 23) | 66.30% |
| hu16G7VHv5VR (SEQ ID NO: 24) | 67.30% |
| hu16G7VHv6a (SEQ ID NO: 25) | 86.70% |
| hu16G7VHv6b (SEQ ID NO: 26) | 88.80% |
| hu16G7VHv7 (SEQ ID NO: 27) | 85.70% |
| hu16G7VLv1 (SEQ ID NO: 28) | 82.20% |
| hu16G7VLv2 (SEQ ID NO: 29) | 86.10% |
| hu16G7VLv3 (SEQ ID NO: 30) | 83.20% |

Positions at which canonical, vernier, or interface residues differ between mouse and human acceptor sequences are candidates for substitution. Examples of canonical/CDR interacting residues include Kabat residues H24, H26, H27, H29, H34, H52a, H55, H70, H71, H74, H94, L2, L4, L25, L27b, L33, L48, L64, L71, L90, and L95 in FIGS. 9A-E. Examples of interface/packing (VH+VL) residues include Kabat residues H35, H37, H39, H45, H47, H91, H93, H95, H100a, H103, L34, L36, L38, L44, L46, L87, L89, L91, L96, L98, in FIGS. 8A-D.

The rationales for selection of the positions indicated in FIGS. 8A-D in the light chain variable region as candidates for substitution are as follows.

M4L is a mutation of a residue that contacts LCDR1 and LCDR3 P43S is a mutation of a residue that contacts two interface residues in (Y91 and W103) in VH. I48M is a mutation of an interface residue. D9S, L15V, R18K, A19V, I21M, and N22S are frequency based back-mutations or frequency/germ-line aligning mutations.

The rationales for selection of the positions indicated in FIGS. 9A-E in the heavy chain variable region as candidates for substitution are as follows.

Q1E is a stability enhancing mutation to mitigate pyro-glutamate formation potential. (Liu, 2011, supra).

S7P is a mutation to proline to improve folding. R71V is a mutation of a residue that may contact HCDR2 via hydrogen bond. T73I is a mutation of a residue that may contact HCDR1 and HCDR2.

V5Q, E10V, V11L, K12V, K13R, V20L, S31G, V37A, R38K, A40R, M48I, N60A, K64Q, R66K, V67A, M69L, I75S, I75A, M80V, S82a-T, R83b-S, R83T, and D85E are frequency based back-mutations or germ-line aligning mutations.

Humanized sequences are generated using a two-stage PCR protocol that allows introduction of multiple mutations, deletions, and insertions using QuikChange site-directed mutagenesis [Wang, W. and Malcolm, B. A. (1999) Bio-Techniques 26:680-682).

The designs based on these human frameworks were:

VARIABLE KAPPA
hu16G7VLv1 (SEQ ID NO: 28):
DIVLTQSPSSLAVSVGEKVTMSCKSSQSLLDGNDQKNYLAWYQQKPGQ

SPKLLMYWASTRESGVPDRFSGSGSGTDFTLTISSLQAEDVAVYYCQQ

FYDYPWTFGGGTKLEIKR hu16G7VLv2 (SEQ ID NO: 29):
DIVLTQSPSSLAVSVGERATISCKSSQSLLDGNDQKNYLAWYQQKPGQ

SPKLLIYWASTRESGVPDRFSGSGSGTDFTLTISSLQAEDVAVYYCQQ

FYDYPWTFGGGTKLEIKR hu16G7VLv3 (SEQ ID NO: 30):
DIVLTQSPSSLAVSVGEKVTMSCKSSQSLLDGNDQKNYLAWYQQKPGQ

SPKLLIYWASTRESGVPDRFSGSGSGTDFTLTISSLQAEDVAVYYCQQ

FYDYPWTFGGGTKLEIKRVARIABLE HEAVY hu16G7VHv1 (SEQ ID NO: 15):
EVQLQQPGSVLVRPGASVKLSCKASGYTFTSSWIHWAKQRPGQGLEWI

GEIYPNSGNTNYNEKFKGKATLTVDISSSTAYVELTSLTSEDTAVYYC

ARLGWLIPLDYWGQGTTVTVSS hu16G7VHv2 (SEQ ID NO:16):
EVQLQQSGAELVKPGASVKLSCKASGYTFTSSWIHWVRQAPGQGLEWI

GEIYPNSGNTNYNEKFKGRVTLTVDTSASTAYMELTSLTSEDTAVYYC

ARLGWLIPLDYWGQGTTVTVSS hu16G7VHv2a (SEQ ID NO: 17):
EVQLVQSGAEVVKPGASVKVSCKASGYTFTSSWIHWVRQRPGQGLEWI

GEIYPNSGNTNYNEKFKGKATLTVDISISTAYMELSRLTSDDTAVYYC

ARLGWLIPLDYWGQGTTVTVSS hu16G7VH2aB7 (SEQ ID NO: 18)
EVQLVQSGAEVVKPGASVKVSCKASGYTFTGSWIHWVRQRPGQGLEWI

GEIYPNSGNTNYAEKFKGKATLTVDISISTAYMELSRLTSDDTAVYYC

ARLGWLIPLDYWGQGTTVTVSS hu16G7VHv2b (SEQ ID NO: 19):
EVQLVQSGAEVVKPGASVKVSCKASGYTFTSSWIHWVRQRPGQGLEWI

GEIYPNSGNTNYNEKFKGRVTLTRDISISTAYMELSRLTSDDTAVYYC

ARLGWLIPLDYWGQGTTVTVSS hu16G7VH2bH7 (SEQ ID NO: 20)
EVQLVQSGAEVVKPGASVKVSCKASGYTFTGSWIHWVRQRPGQGLEWI

GEIYPNSGNTNYAEKFQGRVTLTRDISISTAYMELSRLTSDDTAVYYC

ARLGWLIPLDYWGQGTTVTVSS hu16G7VHv3 (SEQ ID NO: 21):
EVQLQQPGSVLVRPGASVKLSCKASGYTFTSSWIHWVRQAPGQGLEWI

GEIYPNSGNTNYNEKFKGRVTLTVDTSASTAYMELTSLTSEDTAVYYC

ARLGWLIPLDYWGQGTTVTVSS hu16G7VHv4 (SEQ ID NO: 22):
EVQLQQSGAELVKPGASVKLSCKASGYTFTSSWIHWVRQAPGQGLEWI

GEIYPNSGNTNYNEKFKGKATLTVDISSSTAYVELTSLTSEDTAVYYC

ARLGWLIPLDYWGQGTTVTVSS hu16G7VHv5V (SEQ ID NO: 23):
EVQLQQPGSVLVRPGASVKLSCKASGYTFTSSWIHWVKQRPGQGLEWI

GEIYPNSGNTNYNEKFKGKATLTVDISSSTAYVELTSLTSEDTAVYYC

ARLGWLIPLDYWGQGTTVTVSS hu16G7VHv5VR (SEQ ID NO: 24):
EVQLQQPGSVLVRPGASVKLSCKASGYTFTSSWIHWVRQRPGQGLEWI

GEIYPNSGNTNYNEKFKGKATLTVDISSSTAYVELTSLTSEDTAVYYC

ARLGWLIPLDYWGQGTTVTVSS hu16G7VHv6a (SEQ ID NO: 25):
QVQLVQPGAEVKKPGASVKVSCKASGYTFTSSWIHWVRQAPGQGLEWM

GEIYPNSGNTNYNEKFKGRVTMTVDISISTAYMELSRLRSDDTAVYYC

ARLGWLIPLDYWGQGTTVTVSS hu16G7VHv6b (SEQ ID NO: 26):
QVQLVQSGAEVKKPGASVKVSCKASGYTFTSSWIHWVRQAPGQGLEWM

GEIYPNSGNTNYNEKFKGRVTMTVDTSISTAYMELSRLRSDDTAVYYC

ARLGWLIPLDYWGQGTTVTVSS hu16G7VHv7 (SEQ ID NO: 27):
EVQLVQPGAEVKKPGASVKVSCKASGYTFTSSWIHWVRQAPGQGLEWM

GEIYPNSGNTNYNEKFKGRVTMTVDISISTAYMELSRLRSDDTAVYYC

ARLGWLIPLDYWGQGTTVTVSS

Example 4. 16G7 Immunocaptures Tau from Human Alzheimer's Disease Tissue

Figures 4A, 4B:
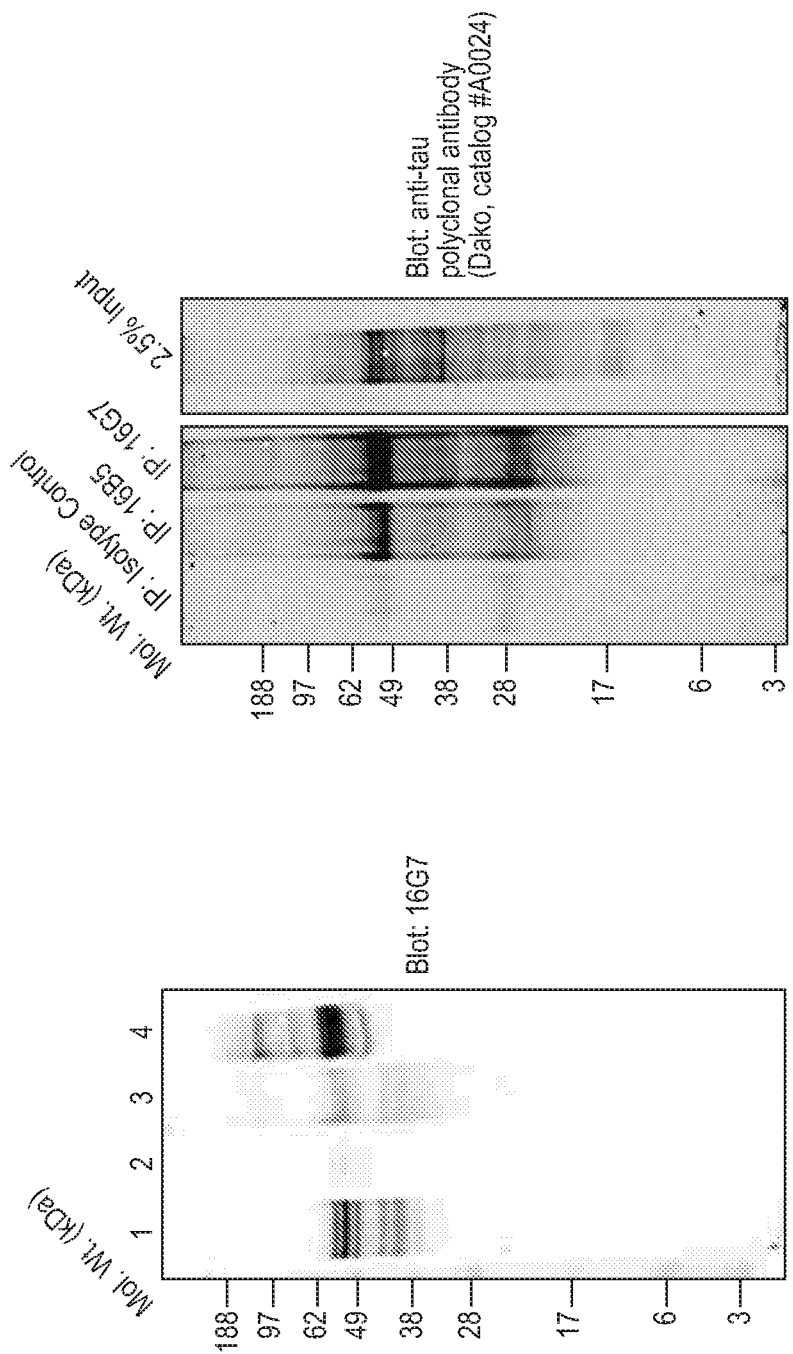
FIGS. 4A and 4B depict results of experiments showing that 16G7 immunocaptures tau from human Alzheimer's disease tissue.

Methods:

FIG. 4A: Temporal cortical tissue from an Alzheimer's disease brain was used to extract protein fractions of varying solubility. Frozen tissue was homogenized in 5 volumes of reassembly (RAB) buffer (100 mM MES, 1 mM EGTA, 0.5 mM $MgSO_4$, 750 mM NaCl, pH 6.8), and centrifuged to generate the RAB-soluble fraction. The pellet was then homogenized in 5 volumes of radioimmunoprecipitation assay (RIPA) buffer (25 mM Tris, 150 mM NaCl, 1% NP-40, 1% sodium deoxycholate, 0.1% SDS, pH 7.5) and centrifuged to generate the RIPA-soluble fraction. This pellet was homogenized in 5 volumes of sarkosyl buffer (25 mM Tris, 1 mM EGTA, 1% sarkosyl, 10% sucrose, 1 mM DTT, 500 mM NaCl, pH 7.5), and centrifuged to generated the sarkosyl-soluble fraction. This final sarkosyl-insoluble pellet was homogenized in 2% SDS. Samples were prepared in reducing/denaturing sample buffer, and resolved by SDS-PAGE. Western blotting was performed using murine 16G7.

FIG. 4B: RAB-soluble protein fractions were prepared to 1 mg/ml. For each immunoprecipitation, 300 μg of sample was used. 10 μg of the indicated antibody (either an isotype control, 16G7, or anti-tau antibody 16B5) was added to the RAB sample preparations, and incubated for 2 hr. Protein G magnetic beads were then added to the mixtures, and incubated for a further hour to capture antibody/antigen complexes. Samples were thoroughly washed with 1×PBS, and beads were boiled in reducing/denaturing sample buffer to release captured proteins. Resulting samples were resolved by SDS-PAGE and Western blotting was performed using a polyclonal anti-tau antibody (Dako, #A0024).

Results:

FIG. 4A: 16G7 recognizes soluble and sarkosyl-insoluble tau from human Alzheimer disease tissue. Protein fractions of varying solubility were resolved by SDS-PAGE and blotted with 16G7. Multiple tau isoforms are seen in soluble and insoluble fractions, and an electrophoretic mobility shift is detected in insoluble fractions, consistent with a pathological form of tau. There is a noted accumulation of tau in the sarkosyl insoluble fraction. Left: Molecular weight markers. Lane designations: 1—RAB soluble, 2—RIPA soluble, 3—Sarkosyl Soluble, 4—Sarkosyl Insoluble.

FIG. 4B: 16G7 immunoprecipitates tau from Alzheimer's disease tissue. RAB-soluble fractions were immunoprecipitated with the indicated antibody, and detected with a polyclonal anti-tau antibody directed towards a separate region of the tau molecule from the binding sites for 16G7 and anti-tau antibody 16B5. 16G7 robustly captures tau from this fraction. The input (RAB-soluble sample) is shown at right.

Example 5. Reactivity Tow Towards Human Alzheimer's Disease Tissue (Immunohistochemistry)

Frontotemporal cortices were obtained from patients without neurodegenerative disease or with Alzheimer's disease, which was confirmed upon post-mortem assessment. Immunohistochemistry was performed on lightly acetone-fixed, 10 µm slide-mounted cryosections. All staining steps were performed using a Leica BOND Rx autostainer, using Leica consumables. Either murine or human forms of 16G7 were incubated with tissue sections followed by addition of species-appropriate secondary antibodies conjugated to an HRP polymer. To prevent non-specific binding of endogenous immunoglobulin when using humanized antibodies on human tissue, the antibodies were non-covalently labeled with a biotin-conjugated anti-human monovalent Fab fragment in vitro before incubation on tissue. Tissue labeled with the primary antibody-biotin Fab fragment complex was further amplified using an avidin-biotin amplification system (Vector Laboratories, Burlingame, Calif.). The staining was visualized with a DAB chromogen, which produced a brown deposit. Negative control consisted of performing the entire immunohistochemical procedure on adjacent sections with an IgG isotype control antibody.

Antibodies tested were murine 16G7, chimeric 16G7 (which contained VH and VL from the murine antibody with human constant regions, heavy chain SEQ ID NO:54 and light chain SEQ ID NO:55), and humanized 16G7 variants hu16G7VHv7/hu16G7VLv2 and hu16G7VHv2bH7/hu16G7VLv2.

Staining performed with murine 16G7, chimeric 16G7, and humanized forms of 16G7 (hu16G7VHv7/hu16G7VLv2 and hu16G7VHv2bH7/hu16G7VLv2) were qualitatively compared and assessed for the strength and intensity of staining, as well as localization of immuoreactivity. Intensity of staining was similar for chimeric and humanized forms of 16G7, and displayed similar localization patterns compared with the murine form of the antibody. Tau was detected in neurofibrillary tangles, fibrils, neuropil threads, and in degenerating axons. There was also notable somal staining detected.

Example 6. Disaggregation Activity

Methods:

Aggregation of recombinant tau—Purified recombinant tau with an N-terminal 6×His tag was combined with equimolar amounts of low-molecular weight heparin in 1×PBS (pH 7.4), and incubated at 37° C. for 96 hr on a nutator. Aggregation of the sample was confirmed by binding to Thioflavin T.

Incubation with antibodies—antibodies were incubated with aggregated, recombinant tau at the indicated molar ratios incubated at 37° C. for 96 hr without rotation or nutation. At the end of the experiment, aggregation was measured by incubating samples with 25 mM Thioflavin T, and measuring emitted fluorescence (450 nm/482 nm excitation/emission). Signals were background subtracted to buffer samples.

Figures 5, 6, 7:
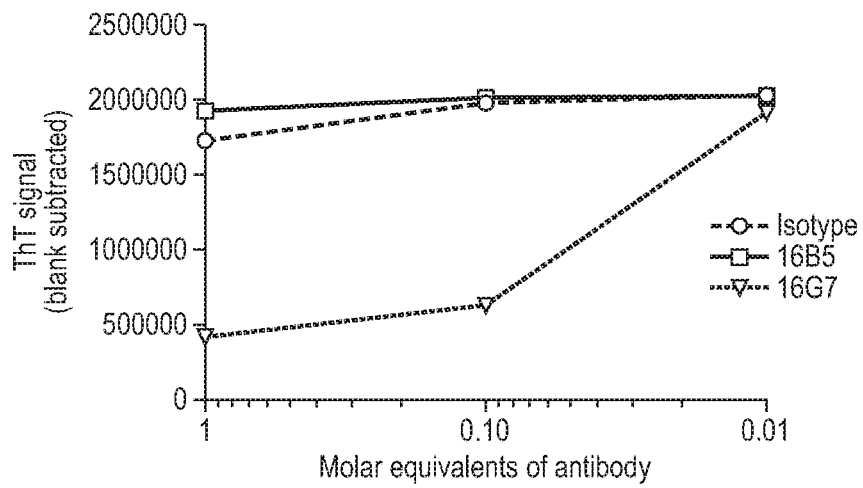
FIG. 5 depicts results of disaggregation assays for selected mouse monoclonal anti-tau antibodies.
FIG. 6 depicts affinity of mouse 16G7 antibody to tau.
FIG. 7 depicts binding kinetics for chimeric 16G7 antibody and humanized 16G7 antibodies VHV2a, VHV2b, and VHV6a H7L2 towards tau.

Results:

As shown in FIG. 5, 16G7 preferentially disassembles intact tau fibrils. Varying molar ratios of 16G7 (triangles), isotype control (circles) and anti-tau antibody 16B5 (squares) were incubated with amyloid-containing tau fibrils for 96 hours. At the end of this period, the extent of aggregation was assessed by binding to thioflavin T. 16G7 preferentially decreases the Thioflavin T signal present in the sample, compared to both an isotype control antibody as well as an anti-tau antibody 16B5 that binds to a different region of tau.

Example 7. Affinity of Murine 16G7 Antibody to Tau

SPR analysis was performed using a Biacore T200 to determine the binding kinetics of 16G7 to recombinant human tau. To prepare a sensor surface, anti-mouse antibody (GE Life Sciences) was immobilized on sensor chip CM5 via amine coupling, and 16G7 was captured at a level to ensure maximum binding of 50 RU. Various concentrations of recombinant tau ranging from 10-0.14 nM were passed over the captured ligand at a flow rate of 50 µL/min in running buffer (HBS+0.05% P-20, 1 mg/mL BSA), for 180 sec association and 900 sec dissociation. Data were double-referenced to both an irrelevant sensor not containing antibody ligand, and 0 nM analyte concentration to account for the dissociation of ligand from the capture moiety. Data was then analyzed using a global 1:1 fit. Binding kinetics are shown in FIG. 6.

Example 8. Affinity of Chimeric 16G7 Antibody and Humanized Variants Towards Tau SPR analysis was performed using a Biacore T200 to determine the binding kinetics of 16G7 to recombinant human tau. To prepare a sensor surface, anti-human antibody (GE Life Sciences) was immobilized on sensor chip CM5 via amine coupling, and chimeric or humanized antibodies were captured at a level to ensure maximum binding of 50 RU. Various concentrations of recombinant tau ranging from 10-0.14 nM were passed over the captured ligands in parallel at a flow rate of 50 µL/min in running buffer (HBS+0.05% P-20, 1 mg/mL BSA), for 180 sec association and 900 sec dissociation. Data were double-referenced to both an irrelevant sensor not containing antibody ligand, and 0 nM analyte concentration to account for the dissociation of ligand from the capture moiety. Data was then analyzed using a global 1:1 fit.

Antibodies tested were chimeric 16G7 ((which contained VH and VL from the murine antibody with human constant regions, heavy chain SEQ ID NO:54 and light chain SEQ ID NO:55), and humanized variants (hu16G7VHv2a/hu16G7VLv2, hu16G7VHv2b/hu16G7VLv2, and hu16G7VHv7/hu16G7VLv2), FIG. 7: Affinity of the tested antibodies was determined by SPR analysis. Varying concentrations of recombinant tau were flowed over immobilized antibody, and resulting sensorgrams were analyzed using a global 1:1 fit. The kinetic affinity, association, and dissociation rates are shown in FIG. 7.

Example 9. Avidity Towards Aggregated Tau

Methods:

Generation of Fab fragments Fab fragments of 16G7 were generated using the Fab Micro Preparation kit following manufacturer's directions (Pierce). Removal of liberated Fc and verification of intact final product were monitored by SDS-PAGE, and concentration was determined using the bicinchoninic acid assay (Pierce).

Aggregation of recombinant tau Purified recombinant tau with an N-terminal 6×His tag was combined with equimolar amounts of low-molecular weight heparin in 1×PBS (pH 7.4), and incubated at 37° C. for 96 hr on a nutator. Aggregation of the sample was confirmed by binding to Thioflavin T.

SPR analysis of Fab fragments and intact antibody Comparative binding studies of Fab fragments and intact antibodies were performed with a Biacore T200. To prepare a sensor surface, anti-his antibodies (GE Life Sciences) were immobilized on sensor chip CM3 via amine coupling, and aggregated recombinant tau (prepared above) was passed over a test channel and acted as the assay ligand. 16G7 (either intact antibody or Fab fragments) were passed over the captured aggregated tau at a flow rate of 50 µL/min in running buffer (HBS+0.05% P-20, 1 mg/mL BSA) in single cycle mode, at concentrations ranging from 10-0.016 nM for 180 sec association phases and a final dissociation phase of 900 sec. Association/dissociation traces were double-reference subtracted to both an irrelevant sensor not containing antibody ligand, and 0 nM analyte concentration to account for the dissociation of ligand from the capture moiety.

Results:

Avidity is the measure of multiple affinities of an antibody-antigen interaction, and more closely represents the functional affinity of an antibody towards an immobilized antigen such as aggregates or neurofibrillary tangles composed of tau. In SPR measurements, the difference between affinity (single interaction) and avidity (multiple interactions) is made by comparing the kinetics of binding of a Fab fragment containing a single binding domain, and an intact antibody with two binding domains.

Figure 8:
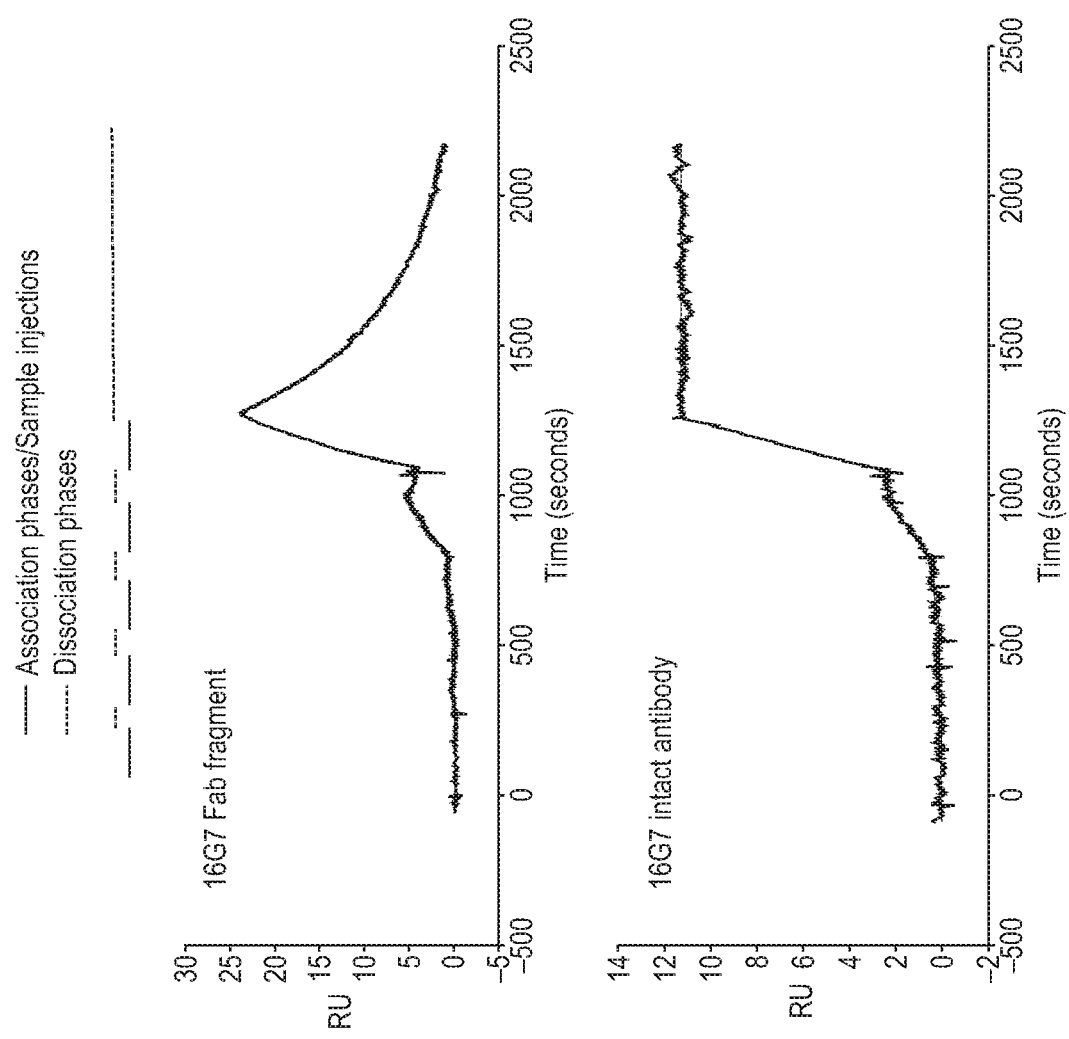
FIG. 8 depicts avidity of mouse 16G7 Fab fragment and mouse 16G7 intact antibody towards aggregated tau.

In FIG. 8, the binding measurements of 16G7 Fab fragments are compared with intact antibody. The association (solid horizontal lines) and dissociation (dashed horizontal lines) phases are diagrammed. The difference between single binding-site affinity and dual binding-site avidity is most apparent in the terminal dissociation phase, starting at 1300 sec. There is no apparent dissociation of antibody/antigen complex for intact antibody, whereas Fab fragments clearly dissociate from aggregated tau.

```
Listing of Sequences
P10636-8 (SEQ ID NO: 1)
MAEPRQEFEVMEDHAGTYGLGDRKDQGGYTMHQDQEGDTDAGLKESPLQTPTEDGSE

EPGSETSDAKSTPTAEDVTAPLVDEGAPGKQAAAQPHTEIPEGTTAEEAGIGDTPSLEDE

AAGHVTQARMVSKSKDGTGSDDKKAKGADGKTKIATPRGAAPPGQKGQANATRIPAK

TPPAPKTPPSSGEPPKSGDRSGYSSPGSPGTPGSRSRTPSLPTPPTREPKKVAVVRTPPKSP

SSAKSRLQTAPVPMPDLKNVKSKIGSTENLKHQPGGGKVQIINKKLDLSNVQSKCGSKD

NIKHVPGGGSVQIVYKPVDLSKVTSKCGSLGNIHHKPGGGQVEVKSEKLDFKDRVQSKI

GSLDNITHVPGGGNKKIETHKLTFRENAKAKTDHGAEIVYKSPVVSGDTSPRHLSNVSST

GSIDMVDSPQLATLADEVSASLAKQGL

P10636-7 (SEQ ID NO: 2)
MAEPRQEFEVMEDHAGTYGLGDRKDQGGYTMHQDQEGDTDAGLKESPLQTPTEDGSE

EPGSETSDAKSTPTAEAEEEAGIGDTPSLEDEAAGHVTQARMVSKSKDGTGSDDKKAKG

ADGKTKIATPRGAAPPGQKGQANATRIPAKTPPAPKTPPSSGEPPKSGDRSGYSSPGSPG

TPGSRSRTPSLPTPPTREPKKVAVVRTPPKSPSSAKSRLQTAPVPMPDLKNVKSKIGSTEN

LKHQPGGGKVQIINKKLDLSNVQSKCGSKDNIKHVPGGGSVQIVYKPVDLSKVTSKCGS

LGNIHHKPGGGQVEVKSEKLDFKDRVQSKIGSLDNITHVPGGGNKKIETHKLTFRENAK

AKTDHGAEIVYKSPVVSGDTSPRHLSNVSSTGSIDMVDSPQLATLADEVSASLAKQGL

P10636-6 (4R0N human tau) (SEQ ID NO: 3)
MAEPRQEFEVMEDHAGTYGLGDRKDQGGYTMHQDQEGDTDAGLKAEEAGIGDTPSLE

DEAAGHVTQARMVSKSKDGTGSDDKKAKGADGKTKIATPRGAAPPGQKGQANATRIP

AKTPPAPKTPPSSGEPPKSGDRSGYSSPGSPGTPGSRSRTPSLPTPPTREPKKVAVVRTPPK

SPSSAKSRLQTAPVPMPDLKNVKSKIGSTENLKHQPGGGKVQIINKKLDLSNVQSKCGS

KDNIKHVPGGGSVQIVYKPVDLSKVTSKCGSLGNIHHKPGGGQVEVKSEKLDFKDRVQ
```

-continued

SKIGSLDNITHVPGGGNKKIETHKLTFRENAKAKTDHGAEIVYKSPVVSGDTSPRHLSNV

SSTGSIDMVDSPQLATLADEVSASLAKQGL

P10636-5 (SEQ ID NO: 4)
MAEPRQEFEVMEDHAGTYGLGDRKDQGGYTMHQDQEGDTDAGLKESPLQTPTEDGSE

EPGSETSDAKSTPTAEDVTAPLVDEGAPGKQAAAQPHTEIPEGTTAEEAGIGDTPSLEDE

AAGHVTQARMVSKSKDGTGSDDKKAKGADGKTKIATPRGAAPPGQKGQANATRIPAK

TPPAPKTPPSSGEPPKSGDRSGYSSPGSPGTPGSRSRTPSLPTPPTREPKKVAVVRTPPKSP

SSAKSRLQTAPVPMPDLKNVKSKIGSTENLKHQPGGGKVQIVYKPVDLSKVTSKCGSLG

NIHHKPGGGQVEVKSEKLDFKDRVQSKIGSLDNITHVPGGGNKKIETHKLTFRENAKAK

TDHGAEIVYKSPVVSGDTSPRHLSNVSSTGSIDMVDSPQLATLADEVSASLAKQGL

P10636-4 (SEQ ID NO: 5)
MAEPRQEFEVMEDHAGTYGLGDRKDQGGYTMHQDQEGDTDAGLKESPLQTPTEDGSE

EPGSETSDAKSTPTAEAEEAGIGDTPSLEDEAAGHVTQARMVSKSKDGTGSDDKKAKG

ADGKTKIATPRGAAPPGQKGQANATRIPAKTPPAPKTPPSSGEPPKSGDRSGYSSPGSPG

TPGSRSRTPSLPTPPTREPKKVAVVRTPPKSPSSAKSRLQTAPVPMPDLKNVKSKIGSTEN

LKHQPGGGKVQIVYKPVDLSKVTSKCGSLGNIHHKPGGGQVEVKSEKLDFKDRVQSKI

GSLDNITHVPGGGNKKIETHKLTFRENAKAKTDHGAEIVYKSPVVSGDTSPRHLSNVSST

GSIDMVDSPQLATLADEVSASLAKQGL

P10636-2 (SEQ ID NO: 6)
MAEPRQEFEVMEDHAGTYGLGDRKDQGGYTMHQDQEGDTDAGLKAEEAGIGDTPSLE

DEAAGHVTQARMVSKSKDGTGSDDKKAKGADGKTKIATPRGAAPPGQKGQANATRIP

AKTPPAPKTPPSSGEPPKSGDRSGYSSPGSPGTPGSRSRTPSLPTPPTREPKKVAVVRTPPK

SPSSAKSRLQTAPVPMPDLKNVKSKIGSTENLKHQPGGGKVQIVYKPVDLSKVTSKCGS

LGNIHHKPGGGQVEVKSEKLDFKDRVQSKIGSLDNITHVPGGGNKKIETHKLTFRENAK

AKTDHGAEIVYKSPVVSGDTSPRHLSNVSSTGSIDMVDSPQLATLADEVSASLAKQGL

SEQ ID NO: 7; VH protein sequence:
QVQLQQPGSVLVRPGASVKLSCKASGYTFTSSWIHWAKQRPGQGLEWIGEIYPNSGNTN

YNEKFKGKATLTVDISSSTAYVDLTSLTSEDSAVYYCARLGWLIPLDYWGQGTTLIVSS

SEQ ID NO: 8; Murine HCDR1:
GYTFTSSWIH

SEQ ID NO: 9; Murine HCDR2:
EIYPNSGNTNYNEKFKG

SEQ ID NO: 10; Murine HCDR3:
LGWLIPLDY

SEQ ID NO: 11; Murine VL protein sequence:
DIVLSQSPSSLAVSVGEKVTMSCKSSQSLLDGNDQKNYLAWYQQKPGQSPKLLMYWAS

TRESGVPDRFTGSGSGTDFTLTISSLKAEDLAVYYCQQFYDYPWTFGGGTKLEIKR

SEQ ID NO: 12; Murine LCDR1:
KSSQSLLDGNDQKNYLA

SEQ ID NO: 13; Murine LCDR2:
WASTRES

SEQ ID NO: 14; Murine LCDR3:
QQFYDYPWT

SEQ ID NO:15; >hu16G7VHv1
EVQLQQPGSVLVRPGASVKLSCKASGYTFTSSWIHWAKQRPGQGLEWIGEIYPNSGNTN

YNEKFKGKATLTVDISSSTAYVELTSLTSEDTAVYYCARLGWLIPLDYWGQGTTVTVSS

-continued

SEQ ID NO: 16; >hu16G7VHv2
EVQLQQSGAELVKPGASVKLSCKASGYTFTSSWIHWVRQAPGQGLEWIGEIYPNSGNTN

YNEKFKGRVTLTVDTSASTAYMELTSLTSEDTAVYYCARLGWLIPLDYWGQGTTVTVSS

SEQ ID NO: 17; >hu16G7VHv2a
EVQLVQSGAEVVKPGASVKVSCKASGYTFTSSWIHWVRQRPGQGLEWIGEIYPNSGNT

NYNEKFKGKATLTVDISISTAYMELSRLTSDDTAVYYCARLGWLIPLDYWGQGTTVTVSS

SEQ ID NO: 18; >hu16G7VHv2aB7
EVQLVQSGAEVVKPGASVKVSCKASGYTFTGSWIHWVRQRPGQGLEWIGEIYPNSGNT

NYAEKFKGKATLTVDISISTAYMELSRLTSDDTAVYYCARLGWLIPLDYWGQGTTVTVSS

SEQ ID NO: 19; >hu16G7VHv2b
EVQLVQSGAEVVKPGASVKVSCKASGYTFTSSWIHWVRQRPGQGLEWIGEIYPNSGNT

NYNEKFKGRVTLTRDISISTAYMELSRLTSDDTAVYYCARLGWLIPLDYWGQGTTVTVSS

SEQ ID NO: 20; >hu16G7VHv2bH7
EVQLVQSGAEVVKPGASVKVSCKASGYTFTGSWIHWVRQRPGQGLEWIGEIYPNSGNT

NYAEKFQGRVTLTRDISISTAYMELSRLTSDDTAVYYCARLGWLIPLDYWGQGTTVTVSS

SEQ ID NO: 21; >hu16G7VHv3
EVQLQQPGSVLVRPGASVKLSCKASGYTFTSSWIHWVRQAPGQGLEWIGEIYPNSGNTN

YNEKFKGRVTLTVDTSASTAYMELTSLTSEDTAVYYCARLGWLIPLDYWGQGTTVTVSS

SEQ ID NO: 22; >hu16G7VHv4
EVQLQQSGAELVKPGASVKLSCKASGYTFTSSWIHWVRQAPGQGLEWIGEIYPNSGNTN

YNEKFKGKATLTVDISSSTAYMELTSLTSEDTAVYYCARLGWLIPLDYWGQGTTVTVSS

SEQ ID NO: 23; >hu16G7VHv5V
EVQLQQPGSVLVRPGASVKLSCKASGYTFTSSWIHWVKQRPGQGLEWIGEIYPNSGNTN

YNEKFKGKATLTVDISSSTAYVELTSLTSEDTAVYYCARLGWLIPLDYWGQGTTVTVSS

SEQ ID NO: 24; >hu16G7VHv5VR
EVQLQQPGSVLVRPGASVKLSCKASGYTFTSSWIHWVRQRPGQGLEWIGEIYPNSGNTN

YNEKFKGKATLTVDISSSTAYVELTSLTSEDTAVYYCARLGWLIPLDYWGQGTTVTVSS

SEQ ID NO: 25; >hu16G7VHv6a
QVQLVQPGAEVKKPGASVKVSCKASGYTFTSSWIHWVRQAPGQGLEWMGEIYPNSGN

TNYNEKFKGRVTMTVDISISTAYMELSRLRSDDTAVYYCARLGWLIPLDYWGQGTTVT

VSS

SEQ ID NO: 26; >hu16G7VHv6b
QVQLVQSGAEVKKPGASVKVSCKASGYTFTSSWIHWVRQAPGQGLEWMGEIYPNSGN

TNYNEKFKGRVTMTVDTSISTAYMELSRLRSDDTAVYYCARLGWLIPLDYWGQGTTVT

VSS

SEQ ID NO: 27; >hu16G7VHv7
EVQLVQPGAEVKKPGASVKVSCKASGYTFTSSWIHWVRQAPGQGLEWMGEIYPNSGN

TNYNEKFKGRVTMTVDISISTAYMELSRLRSDDTAVYYCARLGWLIPLDYWGQGTTVT

VSS

SEQ ID NO: 28; >hu16G7VLv1
DIVLTQSPSSLAVSVGEKVTMSCKSSQSLLDGNDQKNYLAWYQQKPGQSPKLLMYWAS

TRESGVPDRFSGSGSGTDFTLTISSLQAEDVAVYYCQQFYDYPWTFGGGTKLEIKR

SEQ ID NO: 29; >hu16G7VLv2
DIVLTQSPSSLAVSVGERATISCKSSQSLLDGNDQKNYLAWYQQKPGQSPKLLIYWAST

RESGVPDRFSGSGSGTDFTLTISSLQAEDVAVYYCQQFYDYPWTFGGGTKLEIKR

SEQ ID NO: 30; >hu16G7VLv3
DIVLTQSPSSLAVSVGEKVTMSCKSSQSLLDGNDQKNYLAWYQQKPGQSPKLLIYWAS

TRESGVPDRFSGSGSGTDFTLTISSLQAEDVAVYYCQQFYDYPWTFGGGTKLEIKR

-continued

SEQ ID NO: 31; VH Human acceptor AAA18265.1
QVQLVQSGAEVKKPGASVKVSCKASGYTFTDYYMHWVRQAPGRGLEWMGRINPNSG

GTNYAQKFQGRVTMTRDTSIRTAYVELSRLTSDDTAVYYCASLADDDPEDFWGQGTLV

TVSS

SEQ ID NO: 32; VH Human acceptor ADW08092.1
QVQLVESGAEVKKPGASVKLSCKASGYTFSSYWMHWVRQAPGQRLEWMGEINPDNG

HTNYNEKFKSRVTITVDKSASTAYMELSSLRSEDTAVYYCAREADYSYGAFDIWGPGTT

VTVSS

SEQ ID NO: 33; VH human acceptor IMGT# IGHV1-2*02
QVQLVQSGAEVKKPGASVKVSCKASGYTFTGYYMHWVRQAPGQGLEWMGWINPNSG

GTNYAQKFQGRVTMTRDTSISTAYMELSRLRSDDTAVYYC

SEQ ID NO: 34; VL human acceptor AAB24404.1
DIVMTQSPDSLAVSLGERATINCKSSQSLLYSSNNKNYLAWYQQKPGQPPKLLIYWAST

RESGVPDRFSGSGSGTDFTLTISSLQAEDVAVYYCQQYYSTPPMFGQGTKVEIKR

SEQ ID NO: 35; VL Human acceptor AEK69364.1
DIVLTQSPDSLAVSLGERATIKCKSSQSVLYGSDSKNYLAWYQQKPGQPPKLLIYWAST

RESGVPDRFSGSGSGTEFTLTISSLQAADVAVYYCQEYYSSLCTFGQGTKLEIKR

SEQ ID NO: 36; VL Human acceptor IMGT#IGKV4-1*01
DIVMTQSPDSLAVSLGERATINCKSSQSVLYSSNNKNYLAWYQQKPGQPPKLLIYWAST

RESGVPDRFSGSGSGTDFTLTISSLQAEDVAVYYCQQYYSTP

SEQ ID NO: 37; Murine VH nucleotide sequence:
CAGGTCCAACTGCAGCAGCCTGGGTCTGTGCTGGTGAGGCCTGGAGCTTCAGTGAA

GCTGTCCTGCAAGGCTTCTGGCTACACCTTCACCAGCTCCTGGATACACTGGGCGAA

GCAGAGGCCTGGACAAGGCCTTGAGTGGATTGGAGAGATTTATCCTAATAGTGGTA

ATACTAACTACAATGAGAAGTTCAAGGGCAAGGCCACACTGACTGTAGACATATCC

TCCAGCACAGCCTACGTGGATCTCACCAGCCTGACATCTGAGGACTCTGCGGTCTAT

TATTGTGCAAGATTGGGATGGTTAATACCCCTTGACTACTGGGGCCAAGGCACCACT

CTCATAGTCTCCTCA

SEQ ID NO: 38; Murine VL nucleotide sequence:
GACATTGTGCTGTCACAGTCTCCATCCTCCCTAGCTGTGTCAGTTGGAGAGAAGGTT

ACTATGAGCTGCAAGTCCAGTCAGAGCCTTTTAGATGGTAATGATCAAAAGAACTAC

TTGGCCTGGTACCAGCAGAAACCAGGGCAGTCTCCTAAACTGCTGATGTACTGGGCA

TCCACTAGGGAATCTGGGGTCCCTGATCGCTTCACAGGCAGTGGATCTGGGACAGAT

TTCACTCTCACCATCAGCAGTTTGAAGGCTGAAGACCTGGCAGTTTATTACTGTCAG

CAGTTTTATGACTATCCGTGGACGTTCGGTGGAGGCACCAAGCTGGAAATCAAACGT

SEQ ID NO: 39; Kabat CDR-H1
SSWIH

SEQ ID NO: 40; Chothia CDR-H1
GYTFTSS

SEQ ID NO: 41; Chothia CDR-H2
YPNSGN

SEQ ID NO: 42; AbM CDR-H2
EIYPNSGNTN

SEQ ID NO: 43; Contact CDR-L1
KNYLAWY

SEQ ID NO: 44; Contact CDR-L2
LLMYWASTRE

-continued

SEQ ID NO: 45; Contact CDR-L3
QQFYDYPW

SEQ ID NO: 46; Contact CDR-H1
TSSWIH

SEQ ID NO: 47; Contact CDR-H2
WIGEIYPNSGNTN

SEQ ID NO: 48; Contact CDR-H3
ARLGWLIPLD

SEQ ID NO: 49; Alternate CDR-H1
GYTFTGSWIH

SEQ ID NO: 50; Alternate CDR-H2
EIYPNSGNTNYAEKFKG

SEQ ID: 51; Alternate CDR-H2
EIYPNSGNTNYAEKFQG

SEQ ID NO: 52; consensus amino acid sequence among the heavy chain variable regions of the mouse 16G7 and humanized 16G7 antibodies (labeled "Majority' in FIG. 2).
EVQLXQXGAEXVKPGASVKXSCKASGYTFTSSWIHWVRQRPGQGLEWIGEIYPNSGNT

NYNEKFKGXXTLTVDISISTAYMELXXLTSXDTAVYYCARLGWLIPLDYWGQGTTVTV

SS

SEQ ID NO: 53; consensus amino acid sequence among the light chain variable regions of the mouse 16G7 and humanized 16G7 antibodies (labeled "Majority' in FIG. 3).
DIVLTQSPSSLAVSVGEKVTMSCKSSQSLLDGNDQKNYLAWYQQKPGQSPKLLXYWAS

TRESGVPDRFSGSGSGTDFTLTISSLQAEDVAVYYCQQFYDYPWTFGGGTKLEIKR

SEQ ID NO: 54; heavy chain of chimeric 16G7 antibody
QVQLQQPGSVLVRPGASVKLSCKASGYTFTSSWIHWAKQRPGQGLEWIGEIYPNSGNTN

YNEKFKGKATLTVDISSSTAYVDLTSLTSEDSAVYYCARLGWLIPLDYWGQGTTLIVSS

ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPSR

EEMTKNQVSLTCLVKGFYPSDIAVEWESNGQPENNYKTTPPVLDSDGSFFLYSKLTVDK

SRWQQGNVFSCSVMHEALHNHYTQKSLSLSPGK

SEQ ID NO: 55; light chain of chimeric 16G7 antibody
DIVLSQSPSSLAVSVGEKVTMSCKSSQSLLDGNDQKNYLAWYQQKPGQSPKLLMYWAS

TRESGVPDRFTGSGSGTDFTLTISSLKAEDLAVYYCQQFYDYPWTFGGGTKLEIKRKTV

AAPSVFIFPPSDEQLKSGTASVVCLLNNFYPREAKVQWKVDNALQSGNSQESVTEQDSK

DSTYSLSSTLTLSKADYEKHKVYACEVTHQGLSSPVTKSFNRGEC

What is claimed is:

1. An isolated monoclonal antibody, wherein the three heavy chain CDRs are as defined by Kabat/Chothia Composite (SEQ ID NOs: 8, 9, and 10) and the three light chain CDRs are as defined by Kabat/Chothia Composite (SEQ ID NOs: 12, 13, and 14); provided that position H31 is occupied by S or G, position H60 is occupied by N or A and position H64 is occupied by K or Q.

2. The antibody of claim 1, wherein CDR-H1 has an amino acid sequence comprising SEQ ID NO: 49.

3. The antibody of claim 1, wherein CDR-H2 has an amino acid sequence comprising SEQ ID NO: 50.

4. The antibody of claim 1, wherein CDR-H2 has an amino acid sequence comprising SEQ ID NO: 51.

5. The antibody of claim 1, having a mature heavy chain variable region comprising an amino sequence SEQ ID NO: 18 or SEQ ID NO: 20.

6. A method of humanizing a mouse antibody, the method comprising:
   (a) selecting one or more acceptor antibodies;
   (b) identifying the amino acid residues of the mouse antibody to be retained;
   (c) synthesizing a nucleic acid encoding a humanized heavy chain comprising CDRs of the mouse antibody heavy chain and a nucleic acid encoding a humanized light chain comprising CDRs of the mouse antibody light chain; and
   (d) expressing the nucleic acids in a host cell to produce a humanized antibody;
   wherein the mouse antibody is characterized by a mature heavy chain variable region of SEQ ID NO: 7 and a mature light chain variable region of SEQ ID NO:11.

7. An isolated monoclonal antibody, comprising three heavy chain CDRs of SEQ ID NO:7 and three light chain CDRs of SEQ ID NO:11.

8. The antibody of claim 7, wherein the three heavy chain CDRs are as defined by Kabat/Chothia Composite (SEQ ID NOs: 8, 9, and 10) and the three light chain CDRs are as defined by Kabat/Chothia Composite (SEQ ID NOs: 12, 13, and 14).

9. The antibody of claim 7 that is chimeric, veneered, or humanized.

10. A method of producing the humanized, chimeric, or veneered antibody of claim 9, the method comprising:
    (a) culturing cells transformed with nucleic acids encoding the heavy and light chains of the antibody, so that the cells secrete the antibody; and
    (b) purifying the antibody from cell culture media.

11. A method of producing a cell line producing the humanized, chimeric, or veneered antibody of claim 9, the method comprising:
    (a) introducing a vector encoding heavy and light chains of the antibody and a selectable marker into cells;
    (b) propagating the cells under conditions to select for cells having increased copy number of the vector;
    (c) isolating single cells from the selected cells; and
    (d) banking cells cloned from a single cell selected based on yield of antibody.

12. The antibody of claim 7, wherein the antibody is a humanized antibody.

13. The antibody of claim 7 that is an intact antibody.

14. The antibody of claim 7 that is a binding fragment.

15. The antibody of claim 14, wherein the binding fragment is a single-chain antibody, Fab, or Fab'2 fragment.

16. The antibody of claim 7, wherein the isotype is human IgG1.

17. The antibody of claim 7, wherein the isotype is of human IgG2 or IgG4 isotype.

18. The antibody of claim 7, wherein the antibody is conjugated to a therapeutic, cytotoxic, cytostatic, neurotrophic, or neuroprotective agent.

19. A pharmaceutical composition comprising the antibody of claim 7 and a pharmaceutically-acceptable carrier.

20. A nucleic acid encoding the heavy chain and/or light chain of the antibody of claim 7, or a recombinant expression vector comprising the nucleic acid or a host cell transformed with the expression vector.

21. A method of inhibiting or reducing aggregation of tau in a subject having or at risk of developing a tau-mediated amyloidosis, comprising administering to the subject an effective regime of the antibody of claim 7, thereby inhibiting or reducing aggregation of tau in the subject.

22. A method of treating or effecting prophylaxis of a tau-related disease in a subject, comprising administering an effective regime of the antibody of claim 7 and thereby treating or effecting prophylaxis of the disease.

23. A method of reducing aberrant transmission of tau, inducing phagocytosis of tau, inhibiting tau aggregation or deposition, or inhibiting formation of tau tangles, comprising administering an effective regime of the antibody of claim 7 and thereby reducing transmission of tau, inducing phagocytosis of tau, inhibiting tau aggregation or deposition, or inhibiting formation of tau tangles.

24. A method of detecting tau protein deposits in a subject having or at risk of a disease associated with tau aggregation or deposition, comprising administering to a subject the antibody of claim 7, and detecting the antibody bound to tau in the subject.

25. A method of measuring efficacy of treatment in a subject being treated for a disease associated with tau aggregation or deposition, comprising
    (a) measuring a first level of tau protein deposits in the subject prior to treatment by administering to a subject the antibody of claim 7, and detecting a first amount of the antibody bound to tau in the subject,
    (b) administering the treatment to the subject, (c) measuring a second level of tau protein deposits in the subject after treatment by administering to a subject the antibody, and detecting the antibody bound to tau in the subject, wherein a decrease between the first level and the second level of tau protein deposits is detected indicating a positive response to treatment.

26. A method of measuring efficacy of treatment in a subject being treated for a disease associated with tau aggregation or deposition, comprising
(a) measuring a first level of tau protein deposits in the subject prior to treatment by administering to a subject the antibody of claim 7, and detecting a first amount of antibody bound to tau in the subject,
(b) administering the treatment to the subject,
(c) measuring a second level of tau protein deposits in the subject after treatment by administering to a subject the antibody, and detecting a second amount of antibody bound to tau in the subject,
wherein no change between the first and second level of tau protein deposits is detected indicating a positive response to treatment.

27. The humanized antibody of claim 1, wherein the CDRs are of a definition selected from the group of Kabat, Chothia, Kabat/Chothia Composite, AbM and Contact.

28. The humanized antibody of claim 27, wherein the mature light chain variable region is fused to a light chain constant region and the mature heavy chain variable region is fused to a heavy chain constant region.

29. The antibody of claim 28 having at least one mutation in the constant region.

30. The antibody of claim 29, wherein the mutation reduces complement fixation or activation by the constant region or binding to an Fcγ receptor relative to the natural human heavy chain constant region.

31. The antibody of claim 30 having a mutation at one or more of positions 241, 264, 265, 270, 296, 297, 318, 320, 322, 329 and 331 by EU numbering or having an alanine at positions 318, 320 and 322.

32. The humanized antibody of claim 27 wherein the humanized mature heavy chain variable region comprises the three Kabat heavy chain CDRs of SEQ ID NO:39, SEQ ID NO:9, and SEQ ID NO:10 and the humanized mature light chain variable region comprises the three Kabat light chain CDRs of SEQ ID NOs: 12-14.

33. The humanized antibody of claim 27, comprising a humanized mature heavy chain variable region having an amino acid sequence at least 90% identical to any one of SEQ ID NO:15-17, 19, and 21-27 and a humanized mature light chain variable region having an amino acid sequence at least 90% identical to any one of SEQ ID NO: 28-30.

34. The humanized antibody of claim 33, provided positions L4, L9, L15, L22, and L43 in the VL region are occupied by L, S, V, S, and S, respectively.

35. The humanized antibody of claim 33, wherein at least one of the following positions is occupied by the amino acid as specified: L4 is occupied by L, L9 is occupied by S, L15 is occupied by V, L18 is occupied by K, L19 is occupied by V, L21 is occupied by M, L22 is occupied by S, and L43 is occupied by S.

36. The humanized antibody of claim 35, provided positions L4, L9, L15, L18, L19, L21, L22, and L43 in the VL region are occupied by L, S, V, K, V, M, S, and S, respectively.

37. The humanized antibody of claim 33, comprising a mature heavy chain variable region having an amino acid sequence at least 98% identical to any one of SEQ ID NO: 15-17, 19, and 21-27 and a mature light chain variable region having an amino acid sequence at least 98% identical to any one of SEQ ID NO: 28-30.

38. The humanized antibody of claim 37 wherein the mature heavy chain variable region has an amino acid sequence of any of SEQ ID NO: 15-17, 19, and 21-27 and the mature light chain variable region has an amino acid sequence of any one of SEQ ID NO:28-30.

39. The humanized antibody of claim 38, wherein the mature heavy chain variable region has an amino acid sequence of SEQ ID NO:27 and the mature light chain variable region has an amino acid sequence of SEQ ID NO:29.

40. The humanized antibody of claim 33, wherein at least one of the following positions is occupied by the amino acid as specified: H1 is occupied by E, H5 is occupied by Q, H7 is occupied by P, H9 is occupied by S, H10 is occupied by V, H11 is occupied L, H12 is occupied by V, H13 is occupied by R, H20 is occupied by L, H40 is occupied by R, H48 is occupied by I, H66 is occupied by K, H67 is occupied by A, H69 is occupied by L, H71 is occupied by V, H73 is occupied by I, H75 is occupied by S, H80 is occupied by V, H82a is occupied by T, H82b is occupied by S, H83 is occupied by T, and H85 is occupied by E.

41. The humanized antibody of claim 40, provided positions H1, H5, H7, H9, H10, H11, H12, H13, H20, H40, H48, H66, H67, H69, H71, H73, H75, H80, H82a, H82b, H83, and H85 in the VH region are occupied by, E, Q, P, S, V, L, V, R, L, R, I, K, A, L, V, I, S, V, T, S, T, and E, respectively.

42. The humanized antibody of claim 40, provided positions H1, H5, H7, H9, H10, H11, H12, H13, H20, H48, H69, H71, H82a, H82b, H83, and H85 in the VH region are occupied by E, Q, P, S, V, L, V, R, L, I, L, V, T, S, T, and E, respectively.

43. The humanized antibody of claim 40, provided positions H1, H5, H11, H12, H20, H48, H69, H71, H82a, H82b, H83, and H85 in the VH region are occupied by E, Q, L, V, L, I, L, V, T, S, T, and E, respectively.

44. The humanized antibody of claim 40, provided positions H1, H12, H40, H48, H60, H69, H73, and H83 in the VH region are occupied by are occupied by E, V, R, I, A, L, I, and T, respectively.

45. The humanized antibody of claim 40, provided positions H1, H12, H40, H48, H69, H73, and H83 in the VH region are occupied by are occupied by E, V, R, I, L, I, and T, respectively.

46. The humanized antibody of claim 40, provided positions H1, H12, H40, H48, H66, H67, H69, H71, H73, and H83 in the VH region are occupied by are occupied by E, V, R, I, K, A, L, V, I, and T, respectively.

47. The humanized antibody of claim 40, provided positions H1, H12, H40, H48, H69, H73, and H83 in the VH region are occupied by are occupied by E, V, R, I, L, I, and T, respectively.

48. The humanized antibody of claim 40, provided positions H7, H71, and H73 in the VH region are occupied by are occupied by P, V, and I, respectively.

49. The humanized antibody of claim 40, provided position H60 in the VH region is occupied by A.

50. The humanized antibody of claim 33 wherein at least one of the following positions is occupied by the amino acid as specified: H1 is occupied by Q or E, H5 is occupied by V or Q, H7 is occupied by S or P, H9 is occupied by A or S, H10 is occupied by E or V, H11 is occupied V or L, H12 is occupied by K or V, H13 is occupied by K or R, H20 is occupied by V or L, H37 is occupied by V or A, H 38 is occupied by R or K, H40 is occupied by A or R, H48 is occupied by M or I, H60 is occupied by A or N, H64 is occupied by Q or K, H66 is occupied by R or K, H67 is occupied by V or A, H69 is occupied by M or L, H71 is occupied by R or V, H73 is occupied by T or I, H75 is occupied by I, S, or A, H80 is occupied by M or V, H82a is occupied by S or T, H82b is occupied by R or S, H83 is occupied by R or T, and H85 is occupied by D or E.

51. The humanized antibody of claim 50, provided positions H1, H5, H7, H9, H10, H11, H12, H13, H20, H37, H38, H40, H48, H66, H67, H69, H71, H73, H75, H80, H82a, H82b, H83, and H85 in the VH region are occupied by E, Q, P, S, V, L, V, R, L, A, K, R, I, K, A, L, V, I, S, V, T, S, T, and E, respectively.

52. The humanized antibody of claim 50, provided positions H1, H5, H11, H12, H20, H48, H69, I-171, H75, H82a, H82b, H83, and H85 in the VH region are occupied by E, Q, L, V, L, I, L, V, A, T, S, T, and E, respectively.

53. The humanized antibody of claim 50, provided positions H1, H12, H40, H48, H66, H67, H69, H71, H73, and H83 in the VH region are occupied by E, V, R, I, K, A, L, V, I, and T, respectively.

54. The humanized antibody of claim 50, provided positions H1, H12, H40, H48, H60, H66, H67, H69, H71, H73, and H83 in the VH region are occupied by E, V, R, I, A, K, A, L, V, I, and T, respectively.

55. The humanized antibody of claim 50, provided positions H1, H12, H40, H48, H69, H73, and H83 in the VH region are occupied by E, V, R, I, L, I, and T, respectively.

56. The humanized antibody of claim 50, provided positions H1, H12, H40, H48, H60, H66, H67, H69, H71, H73, and H83 in the VH region are occupied by Q, V, R, I, A, K, A, L, V, I, and T, respectively.

57. The humanized antibody of claim 50, provided positions H1, H7, H71, and H73 in the VH region are occupied by Q, P, V and I, respectively.

58. The humanized antibody of claim 50, provided positions H1, H12, H40, H48, H60, H64, H69, H73, and H83 in the VH region are occupied by, E, V, R, I, A, Q, L, I, and T, respectively.

59. The humanized antibody of claim 50, provided positions H1, H5, H7, H9, H10, H11, H12, H13, H20, H48, H69, H71, H75, H82a, H82b, H83, and H85 in the VH region are occupied by E, Q, P, S, V, L, V, R, L, I, L, V, A, T, S, T, and E.

60. The humanized antibody of claim 50, provided positions H1, H5, H11, H12, H20, H48, H66, H67, H69, H71, H73, H75, H82a, H82b, H83, and H85 in the VH region are occupied by, E, Q, L, V, L, I, K, A, L, V, I, S, T, S, T, and E.

61. The humanized antibody of claim 50, provided positions H1, H5, H7, H9, H10, H11, H12, H13, H20, H38, H40, H48, H66, H67, H69, H71, H73I, H75, H80, H82a, H82b, H83, and H85 in the VH region are occupied by E, Q, P, S, V, L, V, R, L, K, R, I, K, A, L, V, I, S, V, T, S, T, and E, respectively.

62. The humanized antibody of claim 50, provided positions H1, H5, H7, H9, H10, H11, H12, H13, H20, H40, H48, H66, H67, H69, H71, H73, H75, H80, H82a, H82b, H83, and H85 in the VH region are occupied by Q, P, S, V, L, V, R, L, R, I, K, A, L, V, I, S, V, T, S, T, and E, respectively.

63. The humanized antibody of claim 50, provided positions H7, H71, and H73 in the VH region are occupied by P, V, and I, respectively.

64. The humanized antibody of claim 50, provided position H71 in the VH region is occupied by V.

65. The humanized antibody of claim 50, provided positions H1, H7, H71, and H73 in the VH region are occupied by E, P, V, and I.

* * * * *

UNITED STATES PATENT AND TRADEMARK OFFICE
CERTIFICATE OF CORRECTION

PATENT NO. : 10,906,964 B2
APPLICATION NO. : 16/097445
DATED : February 2, 2021
INVENTOR(S) : Robin Barbour et al.

Page 1 of 1

It is certified that error appears in the above-identified patent and that said Letters Patent is hereby corrected as shown below:

In the Claims

Column 127, Claim 27, Line 23, delete "1" and insert --7--

Column 129, Claim 52, Line 15, delete "I-171" and insert --H71--

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*